(12) United States Patent
Anand et al.

(10) Patent No.: US 9,126,976 B2
(45) Date of Patent: Sep. 8, 2015

(54) SUBSTITUTED BENZOPIPERAZINES AS CETP INHIBITORS

(75) Inventors: Rajan Anand, Westfield, NJ (US); Vincent J. Colandrea, North Brunswick, NJ (US); Maud Reiter, Geneva (CH); Petr Vachal, Summit, NJ (US); Aaron Zwicker, New Haven, CT (US); Jonathan E. Wilson, Summit, NJ (US); Fengqi Zhang, Edison, NJ (US); Kake Zhao, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/239,452

(22) PCT Filed: Aug. 13, 2012

(86) PCT No.: PCT/US2012/050520
§ 371 (c)(1),
(2), (4) Date: Aug. 20, 2014

(87) PCT Pub. No.: WO2013/028382
PCT Pub. Date: Feb. 28, 2013

(65) Prior Publication Data
US 2014/0357632 A1 Dec. 4, 2014

Related U.S. Application Data

(60) Provisional application No. 61/525,473, filed on Aug. 19, 2011.

(51) Int. Cl.
| | |
|---|---|
| A61K 31/498 | (2006.01) |
| C07D 241/42 | (2006.01) |
| C07D 409/06 | (2006.01) |
| C07D 401/04 | (2006.01) |
| C07D 401/06 | (2006.01) |
| C07D 403/04 | (2006.01) |
| C07D 405/04 | (2006.01) |
| C07D 405/06 | (2006.01) |
| A61K 31/506 | (2006.01) |
| A61K 31/5377 | (2006.01) |
| A61K 45/06 | (2006.01) |

(52) U.S. Cl.
CPC ............ C07D 409/06 (2013.01); A61K 31/498 (2013.01); A61K 31/506 (2013.01); A61K 31/5377 (2013.01); A61K 45/06 (2013.01); C07D 241/42 (2013.01); C07D 401/04 (2013.01); C07D 401/06 (2013.01); C07D 403/04 (2013.01); C07D 405/04 (2013.01); C07D 405/06 (2013.01)

(58) Field of Classification Search
CPC ........................... A61K 31/498; C07D 241/42
USPC ........ 514/249; 544/116, 333, 353; 546/268.1; 548/373.1; 549/59, 356, 362
See application file for complete search history.

(56) References Cited

U.S. PATENT DOCUMENTS

| | | |
|---|---|---|
| 2002/0177708 A1 | 11/2002 | Sikorski et al. |
| 2004/0204450 A1 | 10/2004 | Bechle et al. |

FOREIGN PATENT DOCUMENTS

WO    WO2007081569 A2    7/2007

OTHER PUBLICATIONS

Abu Khalaf, R., Discovery of new cholesteryl ester transfer protein inhibitors via ligand-based pharmacophore modeling and QSAR analysis followed by synthetic exploration, European Journal of Medicinal Chemistry, 2010, 1598-1617, 45.
International Search Report for PCT/US2012/50520, mailed Oct. 11, 2012, pp. 9.
Sikorski, JA, Oral cholesteryl ester transfer protein (CETP) inhibitors: A potential new approach for treating coronary artery disease, Journal of Medicinal Chemistry, 2006, 1-22, 49(1).
European Search Report for EP Application No. 12825316.8, corresponding to PCT/US2012/050520, mailed Mar. 17, 2015, 5 pages.

*Primary Examiner* — Douglas M Willis
(74) *Attorney, Agent, or Firm* — James L. McGinnis; Eric A. Meade; Catherine D. Fitch

(57) ABSTRACT

Compounds having the structure of Formula Ia, including pharmaceutically acceptable salts of the compounds, are CETP inhibitors and may be useful for raising HDL-cholesterol, reducing LDL-cholesterol, and for treating or preventing atherosclerosis.

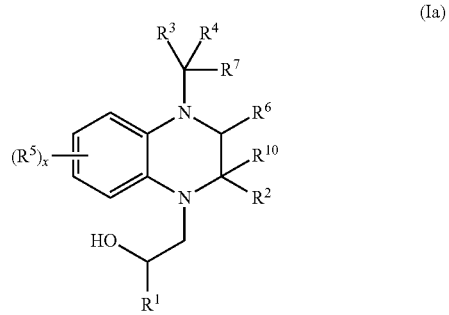

(Ia)

17 Claims, No Drawings

SUBSTITUTED BENZOPIPERAZINES AS CETP INHIBITORS

CROSS REFERENCE TO RELATED APPLICATIONS

This application is a U.S. National Phase application under 35 U.S.C. §371 of PCT Application No. PCT/US2012/50520 filed Aug. 13, 2012, which claims priority from U.S. Provisional Application Ser. No. 61/525,473, filed Aug. 19, 2011.

FIELD OF THE INVENTION

This invention relates to chemical compounds that inhibit cholesterol ester transfer protein (CETP) and are expected to have utility in raising HDL-C, lowering LDL-C, and in the treatment and prevention of atherosclerosis.

BACKGROUND OF THE INVENTION

Atherosclerosis and its clinical consequences, including coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA reductase inhibitors, especially the statins, in reducing coronary events is based on the reduction of circulating low density lipoprotein cholesterol (LDL-C), levels of which correlate directly with an increased risk for atherosclerosis. More recently, epidemiologic studies have demonstrated an inverse relationship between high density lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoprotein and transports cholesterol ester from HDL to the apoB lipoprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120(3), 517-525). Numerous epidemiologic studies correlating the effects of natural variation in CETP activity with respect to coronary heart disease risk have been performed, including studies on a small number of known human null mutations (see Hirano, K.-I., Yamashita, S. and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering LDL-C.

Despite the significant therapeutic advance that statins such as simvastatin and atorvastatin represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin provides an effective therapy for raising HDL-C but suffers from patient compliance issues, due in part to side effects such as flushing. Drugs that inhibit CETP (CETP inhibitors) have been under development with the expectation that they will effectively raise HDL cholesterol levels and also reduce the incidence of atherosclerosis in patients. Torcetrapib was the first drug that was tested in a long-term outcomes clinical trial. The clinical trial of torcetrapib was terminated early due to a higher incidence of mortality in patients to whom torcetrapib and atorvastatin were administered concomitantly compared with patients who were treated with atorvastatin alone. The cause of the increased mortality is not completely understood, but it is not believed to be associated with the CETP inhibiting effects of the drug.

Two other drug candidates, dalcetrapib and anacetrapib, are currently being tested in Phase III clinical trials, including large scale outcomes trials. Data from the recently completed DEFINE Phase III trial of anacetrapib are promising. Patients who were being treated with anacetrapib along with baseline statin therapy showed an increase of HDL-C of 138% and a decrease of LDL-C of 40% compared with patients who were treated with just a statin. See: *N. Engl. J. Med.* 2010: 363: 2406-15. The data in the DEFINE trial were sufficient to indicate that an increase in mortality for patients treated with anacetrapib is unlikely. Additional drug candidates are still being sought that may have properties that are advantageous compared with the CETP inhibitors that have so far been studied or are currently being studied. Such properties may include, for example, higher potency, reduced off-target activity, better pharmacodynamics, higher bioavailability, or a reduced food effect compared with many of the highly lipophilic compounds that have so far been studied. "Food effect" refers to the variability in exposure to the active drug that occurs depending on when the patient had last eaten, whether or not the drug is administered with food, and the fat content of the food.

SUMMARY OF THE INVENTION

The compound having Formula Ia, including pharmaceutically acceptable salts of the compound, is a potent CETP inhibitor, having the utilities described hereinafter:

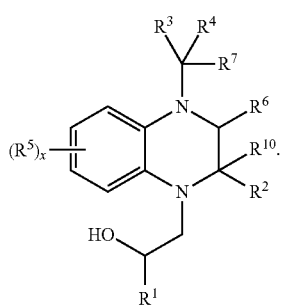

In Formula Ia, $R^1$ is —$C_1$-$C_3$ alkyl which is optionally substituted with 1-5 F or Cl;

$R^2$ is (a) phenyl; (b) naphthyl; (c) phenyl to which is fused a 5-7 membered cycloalkyl ring or a 5-7 membered heterocyclic ring having 1-2 heteroatoms independently selected from O, S, N, and —($NR^8$)— and optionally having 1-3 double bonds; or (d) a 5-6 membered heteroaromatic ring having 1-2 heteroatoms independently selected from O, S, N, and —($NR^8$)—, wherein $R^2$ is optionally substituted with 1-4 substituent groups independently selected from $C_1$-$C_6$ alkyl, —$C_2$-$C_6$ alkenyl, —$C_2$-$C_6$ alkynyl, —$C_3$-$C_8$cycloalkyl optionally having 1-2 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-2 double bonds, —C(=O)$C_1$-$C_6$alkyl, —C(=O)$C_3$-$C_8$cycloalkyl, —C(=O)H, —$CO_2C_1$-$C_6$alkyl, —C(=O)$SC_1$-$C_6$alkyl, —OH, —$NR^8R^9$, —C(=O)$NR^8R^9$, —$NR^8$C(=O)$OC_1$-$C_6$ alkyl, —$NR^8$C(=O)$NR^8R^9$, —S(O)$_2C_1$-$C_6$ alkyl, —S(O)$_2NR^8R^9$, —$NR^8$S(O)$_2NR^8R^9$, halogen, —CN, $NO_2$, and phenyl, wherein $C_1$-$C_6$ alkyl, —$C_2$-$C_6$ alkenyl, and —$C_2$-$C_6$ alkynyl in all instances is optionally substituted with one group —OH and optionally 1-13 halogens, —$C_3$-$C_8$cycloalkyl in all instances is optionally substituted with 1-4 $CF_3$, $CH_3$, —$OCF_3$, —$OCH_3$, Br, Cl, and F substituents, and phenyl is optionally substituted with 1-3 substituent groups independently selected from $C_1$-$C_3$alkyl, —$OC_1$-$C_3$alkyl, and halogen, wherein $C_1$-$C_3$alkyl and —$OC_1$-$C_3$alkyl are optionally substituted with 1-5 halogens;

$R^6$ and each $R^5$ are independently H, $C_1$-$C_4$ alkyl, —$C_2$-$C_4$ alkenyl, —$C_2$-$C_4$ alkynyl, —$OC_1$-$C_4$alkyl, halogen, —CN, —C(=O)$NR^8$, —$NO_2$, or —OH, wherein $C_1$-$C_4$ alkyl, —$C_2$-$C_4$ alkenyl, —$C_2$-$C_4$ alkynyl, and —$OC_1$-$C_4$alkyl are optionally substituted with 1-9 halogens;

$R^8$ and $R^9$ are each independently H or $C_1$-$C_3$ alkyl;

$R^{10}$ is H, $C_1$-$C_3$ alkyl, —$OC_1$-$C_3$alkyl, halogen, —CN, or —OH, wherein $C_1$-$C_3$ alkyl and —$OC_1$-$C_3$alkyl are optionally substituted with 1-7 halogens;

$R^3$ is (a) phenyl, (b) naphthyl, (c) a 5-6 membered heteroaromatic ring having 1-2 heteroatoms independently selected from O, S, N, and —($NR^8$)—, (d) $C_3$-$C_8$cycloalkyl optionally having one double bond, or (e) a 5-6-membered saturated heterocycle having 1-2 heteroatoms independently selected from O, S, N, and $NR^8$, wherein when $R^3$ is phenyl, naphthyl, a 5-6 membered heteroaromatic ring having 1-2 heteroatoms independently selected from O, S, N, and —($NR^8$)—, or a 5-6-membered saturated heterocycle having 1-2 heteroatoms independently selected from O, S, N, and $NR^8$, $R^3$ is optionally substituted with 1-4 substituent groups independently selected from $C_1$-$C_6$ alkyl, —$C_2$-$C_6$ alkenyl, —$C_2$-$C_6$ alkynyl, —$C_3$-$C_8$cycloalkyl optionally having 1-2 double bonds, a 5-6-membered saturated heterocycle having 1-2 heteroatoms independently selected from O, S, N, and $NR^8$, —$OC_1$-$C_6$alkyl, —$OC_2$-$C_6$ alkenyl, —$OC_2$-$C_6$ alkynyl, —$OC_3$-$C_8$ cycloalkyl optionally having 1-2 double bonds, —C(=O)$C_1$-$C_6$alkyl, —C(=O)$C_3$-$C_8$cycloalkyl, —C(=O)H, —$CO_2$H, —$CO_2C_1$-$C_6$alkyl, —C(=O)$SC_1$-$C_6$alkyl, —OH, —$NR^8R^9$, —C(=O)$NR^8R^9$, —$NR^8$C(=O)$OC_1$-$C_6$ alkyl, —$NR^8$C(=O)$NR^8R^9$, —S(O)$_2C_1$-$C_6$ alkyl, —S(O)$_2NR^8R^9$, —$NR^8$S(O)$_2NR^8R^9$, halogen, —CN, and —$NO_2$, wherein $C_1$-$C_6$ alkyl, —$C_2$-$C_6$ alkenyl, and —$C_2$-$C_6$ alkynyl in all instances are optionally substituted with 1-13 halogens independently selected from F, Cl, and Br, and —$C_3$-$C_8$cycloalkyl and the 5-6-membered saturated heterocycle in all instances are optionally substituted with 1-4 groups independently selected from $CF_3$, $CH_3$, —$OCF_3$, —$OCH_3$, Br, Cl, and F;

$R^4$ is H, F, Cl, or $C_1$-$C_3$ alkyl optionally substituted with 1-5 halogens independently selected from F and Cl;

$R^7$ is H, $CF_3$, $CH_3$, or F;

or $R^4$ and $R^7$ are optionally each —$CH_2$— and are joined to form a cyclopropyl group;

or alternatively, $R^3$ is phenyl and $R^4$ has the formula (—$CH_2$—)$_y$, wherein y is an integer from 1-4 and (—$CH_2$—)$_y$ optionally comprises one double bond when y is 2-4, wherein $R^4$ is connected to the phenyl group $R^3$ at the position ortho to the carbon atom which is connected to the carbon atom to which $R^3$, $R^4$, and $R^7$ are connected, thereby yielding a 4-7 membered cycloalkyl or a 5-7-membered cycloalkenyl ring fused to the phenyl ring $R^3$, wherein the phenyl ring $R^3$ and the fused cycloalkyl or cycloalkenyl ring together are optionally substituted with 1-4 groups independently selected from $CF_3$, $CH_3$, —$OCF_3$, —$OCH_3$, and halogen; and x is an integer from 1-4.

In the compounds of Formula Ia, and in subgroups and other embodiments of the compounds, such as those defined by Formula Ib-Ie, the alkyl, alkenyl, and alkynyl groups may be either linear or branched, unless otherwise stated. In general, references to the compounds of Formula Ia herein are meant to also include the compounds of Formula Ib-Ie and other subsets of compounds as may be defined herein.

DETAILED DESCRIPTION OF THE INVENTION

In further embodiments of the invention, the substituent groups defined above may have alternative values independently of one another, as written below. Such embodiments include pharmaceutically acceptable salts when such salts are possible.

In some embodiments, $R^2$ is (a) phenyl; (b) naphthyl; (c) phenyl to which is fused a 5-7 membered cycloalkyl ring or a 5-7 membered heterocyclic ring having 1-2 heteroatoms independently selected from O, S, N, and —($NR^8$)— and optionally having 1-3 double bonds, wherein the fused phenyl ring is connected to the benzopiperazine ring; or (d) a 5-6 membered heteroaromatic ring having 1-2 heteroatoms independently selected from O, S, N, and —($NR^8$)—, wherein $R^2$ is optionally substituted with 1-4 substituent groups independently selected from $C_1$-$C_6$ alkyl, —$C_2$-$C_6$ alkenyl, —$C_2$-$C_6$ alkynyl, —$C_3$-$C_8$cycloalkyl optionally having 1-2 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-2 double bonds, —C(=O)$C_1$-$C_6$alkyl, —C(=O)$C_3$-$C_8$cycloalkyl, —C(=O)H, —$CO_2C_1$-$C_6$alkyl, —C(=O)$SC_1$-$C_6$alkyl, —OH, —$NR^8R^9$, —C(=O)$NR^8R^9$, —$NR^8$C(=O)$OC_1$-$C_6$ alkyl, —$NR^8$C(=O)$NR^8R^9$, —S(O)$_2C_1$-$C_6$ alkyl, —S(O)$_2NR^8R^9$, —$NR^8$S(O)$_2NR^8R^9$, halogen, —CN, and —$NO_2$, wherein $C_1$-$C_6$ alkyl, —$C_2$-$C_6$ alkenyl, and —$C_2$-$C_6$ alkynyl in each instance is optionally substituted with 1-13 halogens, and —$C_3$-$C_8$cycloalkyl optionally having 1-2 double bonds in all instances is optionally substituted with 1-4 groups independently selected from $CF_3$, $CH_3$, —$OCF_3$, —$OCH_3$, Br, Cl, and F.

In some embodiments, $R^3$ is (a) phenyl, (b) naphthyl, (c) a 5-6 membered heteroaromatic ring having 1-2 heteroatoms independently selected from O, S, N, and —($NR^8$)—, or (d) $C_3$-$C_8$cycloalkyl, wherein when $R^3$ is phenyl, naphthyl, or a 5-6 membered heteroaromatic ring having 1-2 heteroatoms independently selected from O, S, N, and —($NR^8$)—, $R^3$ is optionally substituted with 1-4 substituent groups independently selected from $C_1$-$C_6$ alkyl, —$C_2$-$C_6$ alkenyl, —$C_2$-$C_6$ alkynyl, —$C_3$-$C_8$cycloalkyl optionally having 1-2 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-2 double bonds, —C(=O)$C_1$-$C_6$alkyl, —C(=O)$C_3$-$C_8$cycloalkyl, —C(=O)H, —$CO_2$H, —$CO_2C_1$-$C_6$alkyl, —C(=O)S$C_1$-$C_6$alkyl, —OH, —$NR^8R^9$, —C(=O)$NR^8R^9$, —$NR^8$C(=O)$OC_1$-$C_6$ alkyl, —$NR^8$C(=O)$NR^8R^9$, —S(O)$_2C_1$-$C_6$ alkyl, —S(O)$_2NR^8R^9$, —$NR^8$S(O)$_2NR^8R^9$, halogen, —CN, and —$NO_2$, wherein $C_1$-$C_6$ alkyl, —$C_2$-$C_6$ alkenyl, and —$C_2$-$C_6$ alkynyl in each instance is optionally substituted with 1-13 halogens independently selected from F, Cl, and Br, and —$C_3$-$C_8$cycloalkyl in all instances is optionally substituted with 1-4 groups independently selected from $CF_3$, $CH_3$, —$OCF_3$, —$OCH_3$, Br, Cl, and F.

In some embodiments, $R^1$ is $CF_3$ or $CH_3$.

In some embodiments, $R^2$ is phenyl, naphthyl, a 5-6 membered heteroaromatic ring having 1-2 heteroatoms independently selected from N and —($NR^8$)—, or phenyl to which is fused a 5-6-membered heterocyclic ring having 1-2 heteroatoms independently selected from O, S, and —($NR^8$)—, wherein $R^2$ is optionally substituted with 1-2 substituent groups independently selected from $C_1$-$C_3$alkyl, —$OC_1$-$C_3$alkyl, —$NR^8R^9$, —C(=O)$NR^8R^9$, —C(=O)$OC_1$-$C_3$alkyl, —S(O)$_2C_1$-$C_3$ alkyl, Cl, F, —CN, and phenyl, wherein phenyl is optionally substituted with 1-3 substituents independently selected from $CF_3$, $CH_3$, —$OCF_3$, —$OCH_3$, and halogen, wherein $C_1$-$C_3$ alkyl in all instances is optionally substituted with one group —OH and optionally 1-5 F.

In some embodiments, $R^8$ and $R^9$ are each independently selected from H and $C_1$-$C_2$ alkyl.

In some embodiments, $R^3$ is selected from phenyl, naphthyl, a 6-membered heteroaromatic ring having 1-2 heteroatoms independently selected from N and —($NR^8$)—, thienyl, $C_5$-$C_6$cycloalkyl optionally having one double bond, and a 6-membered saturated heterocycle having 1-2 heteroatoms independently selected from O, S, N, and $NR^8$, wherein $R^3$ is optionally substituted with $C_1$-$C_3$alkyl, —$OC_1$-$C_3$alkyl, F, Cl, and a 6-membered saturated heterocycle having 1-2 heteroatoms independently selected from O, S, N, and $NR^8$, wherein $C_1$-$C_3$ alkyl and $OC_1$-$C_3$ alkyl are optionally substituted with 1-5 F, and the 6-membered saturated heterocycle having 1-2 heteroatoms independently selected from O, S, N, and $NR^8$ is optionally substituted with 1-3 substituents independently selected from $CF_3$, $CH_3$, —$OCF_3$, —$OCH_3$, Br, Cl, and F.

In some embodiments, $R^2$ is phenyl, naphthyl, pyrazolyl, pyridinyl, pyrimidinyl, or 2,3-dihydrobenzodioxinyl, wherein $R^2$ is optionally substituted with 1-2 substituents independently selected from $CH_3$, —$OCH_3$, $CF_3$, —$OCF_3$, —$OC_2H_5$, —$OCF_2$H, —$OCF_2CF_2$H, —C($CH_3$)$_2$OH, —C(=O)NH$CH_3$, —C(=O)O$CH_3$, —$SO_2CH_3$, —N($CH_3$)$_2$, F, Cl, —CN, and phenyl;

In some embodiments, $R^3$ is phenyl, pyridinyl, thienyl, cyclohexyl, cyclohexenyl, or tetrahydropyranyl optionally substituted with 1-2 substituent groups independently selected from $CH_3$, —$OCH_3$, $CF_3$, —$OCF_2$H, —$OCF_3$, $C_2H_5$, —$OC_2H_5$, —OCH($CH_3$)$_2$, —$OCF_2CF_2$H, F, Cl, and morpholinyl;

In some embodiments, $R^4$ is H or $C_1$-$C_2$ alkyl.

In some embodiments, $R^3$ is phenyl and $R^4$ has the formula (—$CH_2$—)$_y$, wherein y is an integer from 2-4 and (—$CH_2$—)$_y$ optionally comprises one double bond, wherein $R^4$ is connected to the phenyl group $R^3$ at the position ortho to the carbon atom which is connected to the carbon atom to which $R^3$, $R^4$, and $R^7$ are connected, thereby yielding a 5-7 membered cycloalkyl or cycloalkenyl ring fused to the phenyl ring $R^3$, wherein the phenyl group $R^3$ and the fused cycloalkyl or cycloalkenyl ring together are optionally substituted with 1-4 groups independently selected from $CF_3$, $CH_3$, —$OCF_3$, —$OCH_3$, and halogen.

In some embodiments, $R^5$ and $R^6$ are each independently selected from H, $CF_3$, $CH_3$, and halogen.

In some embodiments, $R^7$ and $R^{10}$ are H.

In some embodiments, x is 1 or 2.

In some embodiments, $R^2$ is phenyl, naphthyl, a 5-6 membered heteroaromatic ring having 1-2 heteroatoms independently selected from N and —($NR^8$)—, or a phenyl to which is fused a 6-membered heterocyclic ring having 1-2 heteroatoms independently selected from O, S, and —($NR^8$)—, wherein $R^2$ is optionally substituted with 1-2 substituent groups independently selected from $C_1$-$C_2$alkyl, —$OC_1$-$C_2$alkyl, —$NR^8R^9$, —C(=O)$NR^8R^9$, —C(=O)$OC_1$-$C_2$alkyl, —S(O)$_2C_1$-$C_2$ alkyl, Cl, F, and —CN, wherein $C_1$-$C_2$ alkyl in all instances is optionally substituted with 1-5 F.

In some embodiments, $R^2$ is phenyl, naphthyl, a 5-6 membered heteroaromatic ring having 1-2 heteroatoms independently selected from N and —($NR^8$)—, or phenyl to which is fused a 5-6-membered heterocyclic ring having 1-2 heteroatoms independently selected from O, S, and —($NR^8$)—, wherein $R^2$ is optionally substituted with 1-2 substituent groups independently selected from $C_1$-$C_3$alkyl, —$OC_1$-$C_3$alkyl, —$NR^8R^9$, —C(=O)$NR^8R^9$, —C(=O)$OC_1$-$C_3$alkyl, —S(O)$_2C_1$-$C_3$ alkyl, Cl, F, —CN, and phenyl, wherein phenyl is optionally substituted with 1-3 substituents independently selected from $CF_3$, $CH_3$, —$OCF_3$, —$OCH_3$, and halogen, wherein $C_1$-$C_3$ alkyl in all instances is optionally substituted with one group —OH and optionally 1-5 F.

In some embodiments, $R^3$ is selected from phenyl, naphthyl, a 6-membered heteroaromatic ring having 1-2 heteroatoms independently selected from N and —($NR^8$)—, thienyl, $C_5$-$C_6$cycloalkyl optionally having one double bond, and a 6-membered saturated heterocycle having 1-2 heteroatoms independently selected from O, S, N, and $NR^8$, wherein $R^3$ is optionally substituted with $C_1$-$C_3$alkyl, —$OC_1$-$C_3$alkyl, F, Cl, and a 6-membered saturated heterocycle having 1-2 heteroatoms independently selected from O, S, N, and $NR^8$, wherein $C_1$-$C_3$ alkyl and $OC_1$-$C_3$ alkyl are optionally substituted with 1-5 F, and the 6-membered saturated heterocycle having 1-2 heteroatoms independently selected from O, S, N, and $NR^8$ is optionally substituted with 1-3 substituents independently selected from $CF_3$, $CH_3$, —$OCF_3$, —$OCH_3$, Br, Cl, and F.

In some embodiments, $R^3$ is selected from phenyl, naphthyl, a 6-membered heteroaromatic ring having 1-2 heteroatoms independently selected from N and —($NR^8$)—, thienyl, and $C_5$-$C_6$cycloalkyl, wherein $R^3$ is optionally substituted with $C_1$-$C_3$alkyl, —$OC_1$-$C_3$alkyl, F, and Cl, where $C_1$-$C_3$ alkyl and $OC_1$-$C_3$ alkyl are optionally substituted with 1-5 F.

In other embodiments, $R^3$ is selected from phenyl, pyridinyl, thienyl, or cyclohexyl, and $R^3$ is optionally substituted with 1-2 substituent groups independently selected from CH$_3$, —OCH$_3$, CF$_3$, —OCF$_3$, C$_2$H$_5$, —OC$_2$H$_5$, —OCH(CH$_3$)$_2$, —OCF$_2$CF$_2$H, F, and Cl.

In other embodiments, R$^2$ is phenyl, naphthyl, pyrazolyl, pyridinyl, pyrimidinyl, or 2,3-dihydrobenzodioxinyl, wherein R$^2$ is optionally substituted with 1-2 substituents independently selected from CH$_3$, —OCH$_3$, CF$_3$, —OCF$_3$, —OC$_2$H$_5$, —OCF$_2$CF$_2$H, —C(=O)NHCH$_3$, —C(=O)OCH$_3$, —SO$_2$CH$_3$, —N(CH$_3$)$_2$, F, Cl, and —CN.

In some embodiments, R$^8$ and R$^9$ are each independently selected from H and C$_1$-C$_2$ alkyl. In other embodiments, R$^8$ and R$^9$ are each independently selected from H and CH$_3$. In other embodiments, R$^8$ and R$^9$ are each CH$_3$. In other embodiments, R$^8$ and R$^9$ are H.

In some embodiments, R$^4$ is H or C$_1$-C$_2$ alkyl. In other embodiments, R$^4$ is H or CH$_3$. In other embodiments, R$^4$ is H.

In alternative embodiments, R$^3$ is phenyl and R$^4$ has the formula (—CH$_2$—)$_y$, where y is an integer from 2-4, and (—CH$_2$—)$_y$ optionally contains one double bond, wherein R$^4$ is connected to the phenyl group R$^3$ at the position ortho to the carbon atom which is connected to the carbon atom to which R$^3$, R$^4$, and R$^7$ are connected, thereby yielding a 5-7 membered cycloalkyl or cycloalkenyl ring fused to the phenyl ring R$^3$, wherein the phenyl group R$^3$ and the fused cycloalkyl or cycloalkenyl ring together are optionally substituted with 1-4 groups independently selected from CF$_3$, CH$_3$, —OCF$_3$, —OCH$_3$, and halogen.

In another alternative embodiment, R$^3$ is phenyl, and R$^4$ optionally is (—CH$_2$—)$_3$ or —HC=CH—, wherein R$^4$ is attached to the phenyl group R$^3$ at the position that is ortho to the carbon atom that is attached to the carbon atom to which R$^3$, R$^4$, and R$^7$ are attached, thereby yielding a tetrahydronaphthalenyl or indenyl ring connected to the N of the benzopiperazine.

In some embodiments, R$^5$ and R$^6$ are each independently selected from H, CF$_3$, CH$_3$, and halogen.

In some embodiments, R$^5$ and R$^6$ are each independently selected from H, CF$_3$ and CH$_3$.

In some embodiments, R$^5$ is CF$_3$ or CH$_3$.

In some embodiments R$^7$ and R$^{10}$ are H.

In some embodiments R$^5$, R$^6$, R$^7$ and R$^{10}$ are all H.

In some embodiments, x is 1.

In some embodiments, x is 0 or 1.

In some embodiments, x is 1 or 2.

In some embodiments, x is 0 or 1.

In some embodiments, x is an integer from 1-4.

The various embodiments described above are also independently applicable for compounds having Formula Ib:

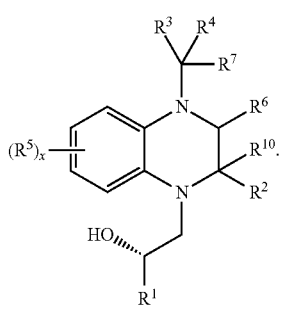

Ib

The various embodiments described above are also independently applicable for compounds having Formula Ic:

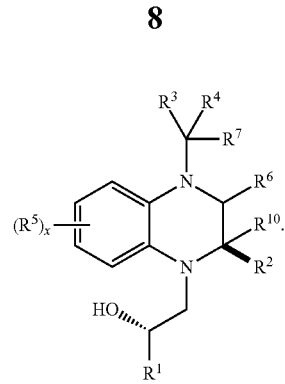

Ic

The embodiments described above are also independently applicable for compounds having Formula Id. In these embodiments, R$^5$, R$^6$, R$^7$ and R$^{10}$ are H. R$^1$, R$^2$, R$^3$ and R$^4$ can have the values provided previously independently of one another.

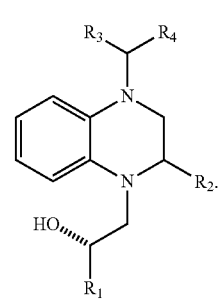

Id

The embodiments described above are also independently applicable for compounds having Formula Ie. In these embodiments, R$^5$, R$^6$, R$^7$ and R$^{10}$ are H. R$^1$, R$^2$, R$^3$ and R$^4$ can have the values provided previously independently of one another.

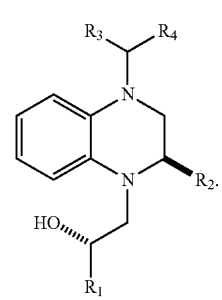

Ie

Definitions and Abbreviations

"Ac" is acetyl, which is CH$_3$C(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, n-butyl, sec-butyl, tert-butyl, pentyl, hexyl, heptyl, octyl, nonyl, and the like.

"Alkylene" groups are alkyl groups that are difunctional rather than monofunctional. For example, methyl is an alkyl group and methylene (—CH$_2$—) is the corresponding alkylene group.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated. The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double binds.

"Aryl" when used to describe a substituent or group in a structure means a monocyclic or bicyclic compound in which the rings are aromatic and which contain only carbon ring atoms. The term "aryl" can also refer to an aryl group that is fused to a cycloalkyl or heterocycle. Preferred "aryls" are phenyl and naphthyl. Phenyl is generally the most preferred aryl group.

"Heterocyclyl," "heterocycle," and "heterocyclic" means a fully or partially saturated or aromatic 5-7 membered ring containing 1-2 heteroatoms independently selected from N, S O, and ($NR^8$) and optionally having 1-3 double bonds, unless otherwise stated.

"Benzoheterocycle" represents a phenyl ring fused to a 5-7-membered heterocyclic ring having 1-2 heteroatoms, each of which is O, N, S, or ($NR^8$) wherein the heterocyclic ring optionally has 1-3 double bonds. Examples include indole, benzofuran, 2,3-dihydrobenzofuran and quinoline.

"chiral OD" is Daicel CHIRALCEL® OD
"chiral IA" is Daicel CHIRALCEL® IA
"chiral IB" is Daicel CHIRALCEL® IB
"chiral OJ" is Daicel CHIRALCEL® OJ
"DIPEA" is diisopropylethylamine.
"DCM" is dichloromethane.
"DEA" is diethylamine.
"DMF" is N,N-dimethylformamide.
"ETOAc" is ethyl acetate.
"Halogen" includes fluorine, chlorine, bromine and iodine.
"HOBT" is 1-Hydroxybenzotriazole.
"Hunig's base" is N,N-diisopropylethylamine.
"IPAC" is isopropyl acetate.
"LCMS" is liquid chromatography mass spectrometry.
"Me" represents methyl.
"MeOH" is methanol.
"r.t." is room temperature.
"SFC" is supercritical fluid chromatography.
"S-Phos" is 2-Dicyclohexylphosphino-2',6'-dimethoxybiphenyl (CAS#657408-07-6).
"TFA" is trifluoroacetic acid.
"THF" is tetrahydrofuran.
"TLC" is thin layer chromatography.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof Optical Isomers-Diastereomers-Geometric Isomers-Tautomers The compounds disclosed herein have at least two asymmetric centers, and can thus occur as pure stereoisomers and as mixtures of stereoisomers, including racemates, racemic mixtures, single enantiomers, mixtures of enantiomers, diastereomeric mixtures and individual diastereomers. Different stereoisomers having the same 2-dimensional chemical structure may have different levels of activity with respect to CETP inhibition, so that some stereoiomers may have high activity and others may have little activity. The compounds that are potent inhibitors of CETP may have utility in patients for raising HDL-C, lowering LDL-C, treating dyslipidemia, and for preventing, treating or delaying the onset of conditions that are related to atherosclerosis. Stereoisomers that have little or no activity may have utility as research tools for better understanding CETP inhibition. All stereoisomers of the claimed compounds thus have utility.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, triethanolamine, trimethylamine, tripropylamine, tromethamine, and the like.

When the compound of the present invention is basic, salts may be prepared from pharmaceutically acceptable non-toxic acids, including inorganic and organic acids. Such acids include acetic, adipic, ascorbic, benzenesulfonic, benzoic, camphorsulfonic, citric, diethylacetic, ethanesulfonic, formic, fumaric, gluconic, glutamic, hydrobromic, hydrochloric, isethionic, isonicotinic, lactic, maleic, malic, malonic, mandelic, methanesulfonic, mucic, naphthalendisulfonic, nitric, oxalic, pamoic, pantothenic, phenylpropionic, phosphoric, pimelic, pivalic, propionic, salicylic, succinic, sulfuric, sulfaminic, tartaric, p-toluenesulfonic acid, trifluoroacetic and the like. Particularly preferred are citric, hydrobromic, hydrochloric, maleic, phosphoric, sulfuric, and tartaric acids.

It will be understood that, as used herein, references to the compounds of the invention are also meant to be references to the compounds of Formula Ia-Ie and to the examples, and are meant to also include the pharmaceutically acceptable salts, where such salts are possible.

Prodrugs

Prodrugs, which are compounds that are converted to the compound of Formula Ia-Ie as they are being administered to a patient or after they have been administered to a patient, are also compounds of this invention in the sense that they provide the claimed pharmaceutically active drug moiety to the patient.

Utilities

The compounds disclosed herein, including pharmaceutically acceptable salts thereof, are potent inhibitors of CETP. The compounds are therefore useful in treating mammalian patients, preferably human patients, having diseases and conditions that are treated by inhibition of CETP.

One aspect of the present invention provides a method for treating or reducing the risk of developing a disease or condition that may be treated or prevented by inhibition of CETP by administering a therapeutically effective amount of the compounds of Formula Ia-Ie to a patient in need of treatment. The patient is a human or mammal, but is most often a human. A "therapeutically effective amount" is the amount of compound that is effective in obtaining a desired clinical outcome in the treatment of a specific disease.

Diseases or conditions that may be treated with the compounds of this invention, or which the patient may have a reduced risk of developing as a result of being treated with the compounds of this invention, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome.

The compounds disclosed herein are expected to be effective in raising HDL-C and/or increasing the ratio of HDL-C to LDL-C. The compounds may also be effective in reducing LDL-C, and may be effective in treating dyslipidemia. These changes in HDL-C and LDL-C may be beneficial in treating atherosclerosis, reducing or reversing the development of atherosclerosis, reducing the risk of developing atherosclerosis, or preventing atherosclerosis. The compounds disclosed herein thus may be beneficial in treating atherosclerosis, reducing or reversing the development of atherosclerosis, reducing the risk of developing atherosclerosis, and preventing atherosclerosis.

Administration and Dose Ranges

Any suitable route of administration may be employed for providing a mammal, especially a human, with an effective dose of the compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably the compound of Formula Ia-Ie is administered orally.

When treating the diseases for which the compound of Formula Ia-Ie is indicated, generally satisfactory results are expected when the compound of the present invention is administered at a daily dosage of from about 0.1 milligram to about 1000 milligram in one dose daily or divided into more than one dose per day.

Oral administration will usually be carried out using tablets. Examples of doses in tablets include 0.1 mg, 0.5 mg, 1 mg, 2 mg, 5 mg, 10 mg, 25 mg, 50 mg, 100 mg, 250 mg, 500 mg, and 1000 mg. Other oral forms can also have the same dosages (e.g. capsules).

Pharmaceutical Compositions

Another aspect of the present invention provides pharmaceutical compositions which comprise the compound of Formula Ia-Ie and a pharmaceutically acceptable carrier. The pharmaceutical compositions of the present invention comprise the compounds of Formula Ia-Ie or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. A pharmaceutical composition may also consist essentially of the compound of Formula Ia-Ie, or a pharmaceutically acceptable salt of the compound, and a pharmaceutically acceptable carrier, without other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compound of Formula Ia-Ie can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compound can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The Compound of Formula Ia-Ie may also be administered parenterally. Solutions or suspensions of the compound can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

The compounds of Formula Ia-Ie, including pharmaceutically acceptable salts, may be used in combination with other drugs that may also be useful in the treatment or amelioration of the diseases or conditions for which the compounds of Formula Ia-Ie are useful. Such other drugs may be administered, by a route and in an amount commonly used therefor, contemporaneously or sequentially with the compound of Formula Ia-Ie. When the compound of Formula Ia-Ie is used contemporaneously with one or more other drugs, a pharmaceutical composition in unit dosage form containing such other drugs and the compound of Formula Ia-Ie is preferred. However, the combination therapy also includes therapies in which the compound of Formula Ia-Ie and one or more other drugs are administered concomitantly, on the same or different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula Ia-Ie.

Examples of other active ingredients that may be administered in combination with a compound of this invention (e.g. Formula Ia-Ie), and either administered separately or in the same pharmaceutical composition, include, but are not limited to, other compounds which improve a patient's lipid profile, such as (i) HMG-CoA reductase inhibitors, (which are generally statins, including simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); rivastatin, pitavastatin, and other statins), (ii) bile acid sequestrants (cholestyramine, colestipol, dialkylaminoalkyl derivatives of a cross-linked dextran, Colestid®, LoCholest®, (iii) niacin and related compounds, such as nicotinyl alcohol, nicotinamide, and nicotinic acid or a salt thereof, (iv) PPARγ agonists, such as gemfibrozil and fenofibric acid derivatives (fibrates), including clofibrate, fenofibrate, bezafibrate, ciprofibrate, and etofibrate, (v) cholesterol absorption inhibitors, such as stanol esters, beta-sitosterol, sterol glycosides such as tiqueside; and azetidinones, such as ezetimibe, (vi) acyl CoA:cholesterol acyltransferase (ACAT) inhibitors, such as avasimibe and melinamide, and including selective ACAT-1 and ACAT-2 inhibitors and dual inhibitors, (vii) phenolic anti-oxidants, such as probucol, (viii) microsomal triglyceride transfer protein (MTP)/ApoB secretion inhibitors, (ix) anti-oxidant vitamins, such as vitamins C and E and beta carotene, (x) thyromimetics, (xi) LDL (low density lipoprotein) receptor inducers, (xii) platelet aggregation inhibitors, for example glycoprotein IIb/IIIa fibrinogen receptor antagonists and aspirin, (xiii) vitamin B12 (also known as cyanocobalamin), (xiv) folic acid or a pharmaceutically acceptable salt or ester thereof, such as the sodium salt and the methylglucamine salt, (xv) FXR and LXR ligands, including both inhibitors and agonists, (xvi) agents that enhance ABCA1 gene expression, and (xvii) ileal bile acid transporters.

Preferred classes of therapeutic compounds that can be used with the compounds of this invention for uses described above, such as improving a patient's lipid profile (i.e. raising HDL-C and lowering LDL-C) and for treating, preventing, or reducing the risk of developing atherosclerosis, include one or both of statins and cholesterol absorption inhibitors. Particularly preferred are combinations of the compounds of this invention with a statin, with ezetimibe, or with both a statin and ezetimibe. Statins that may be used in these combinations include simvastatin, lovastatin, rosuvastatin, pravastatin, fluvastatin, atorvastatin, rivastatin, and pitavastatin. Preferred statins for use in combination therapy include simvastatin, atorvastatin, and rosuvastatin. Preferred combinations include combinations of a CETP inhibitor as disclosed herein and one or more cholesterol reducing agents, such as (a) atorvastatin; (b) simvastatin; (c) rosuvastatin; (d) ezetimibe; (e) atorvastatin and ezetimibe; (f) simvastastin and ezetimibe; or (g) rosuvastatin and ezetimibe.

Finally the compound of this invention can be used with compounds that are useful for treating other diseases, such as diabetes, hypertension and obesity, as well as other anti-atherosclerotic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these diseases, allowing for the possibility of administering reduced doses of active ingredients, such as doses that otherwise might be sub-therapeutic.

Examples of other active ingredients that may be administered in combination with a compound of this invention include, but are not limited to, compounds that are primarily anti-diabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818;

(b) biguanides such as metformin and phenformin;

(c) protein tyrosine phosphatase-1B (PTP-1B) inhibitors;

(d) dipeptidyl peptidase IV (DP-IV) inhibitors, including sitagliptin, vildagliptin, saxagliptin, and alogliptin;

(e) insulin or insulin mimetics, such as for example insulin lispro, insulin glargine, insulin zinc suspension, and inhaled insulin formulations;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 analogs, such as exendins, such as for example exenatide (Byetta); and non-peptidyl GLP-1 receptor agonists;

(l) GIP-1; and (m) Non-sulfonylurea insulin secretagogues, such as the meglitinides (e.g. nateglinide and rapeglinide).

Preferred combinations with antidiabetic compounds include combinations of the compounds disclosed herein with DP-IV inhibitors (sitagliptin, alogliptin, vildagliptin, saxagliptin, linagliptin, dutogliptin, or gemigliptin), combinations with biguanides, and combinations with both a DP-IV inhibitor and a biguanide. The preferred DP-IV inhibitor is sitagliptin, and the preferred biguanide is metformin.

These other active ingredients that may be used in combination with the current invention also include antiobesity compounds, including 5-HT(serotonin) inhibitors, neuropeptide Y5 (NPY5) inhibitors, melanocortin 4 receptor (Mc4r) agonists, cannabinoid receptor 1 (CB-1) antagonists/inverse agonists, and ß3 adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compounds of this invention. Examples of antihypertensive compounds that may be used with the compounds of this invention include (1) angiotensin II antagonists, such as candesartan, eprosartan, irbesartan, losartan, olmesartan, telmisartan, and valsartan; (2) angiotensin converting enzyme inhibitors (ACE inhibitors), such as alacepril, benazepril, captopril, ceronapril, cilazapril, delapril, enalapril, enalaprilat, fosinopril, imidapril, lisinopril, moexepril, moveltipril, perindopril, quinapril, ramipril, spirapril, temocapril, or trandolapril; (3) calcium channel blockers such as nifedipine and diltiazam; and (4) endothelin antagonists.

Preferred antihypertensives that may be used in combination with the CETP inhibitors disclosed herein include one or more of an angiotensin II antagonist (losartan), an ACE inhibitor (enalapril or captopril), and hydrochlorothiazide.

Anti-obesity compounds may be administered in combination with the compounds of this invention, including: (1) growth hormone secretagogues and growth hormone secretagogue receptor agonists/antagonists, such as NN703 and hexarelin; (2) protein tyrosine phosphatase-1B (PTP-1B) inhibitors; (3) cannabinoid receptor ligands, such as cannabinoid CB1 receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystokinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, amrinone, milrinone, cilostamide, rolipram, and cilomilast; (26) phosphodiesterase-3B (PDE3B) inhibitors; (27) NE (norepinephrine) transport inhibitors, such as GW 320659, despiramine, talsupram, and nomifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6,beta-Ala11,Phe13,Nle14]Bn(6-14) and [D-Phe6, Phe13]Bn(6-13)propylamide; (32) CNTF (Ciliary neurotrophic factors), such as GI-181771 (Glaxo-SmithKline), SR146131 (Sanofi Synthelabo), butabindide, PD170,292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone β agonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40) ACC2 (acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM-43004C, (45) Neuropeptide Y2 (NPY2) receptor agonists such NPY3-36, N acetyl [Leu(28,31)] NPY 24-36, TASP-V, and cyclo-(28/32)-Ac-

[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) aminorex; (81) amphechloral; (82) amphetamine; (83) benzphetamine; and (84) chlorphentermine.

The combination therapies described above which use the compounds of this invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

ASSAYS

Protocol: Scintillation Proximity Assay (SPA) for CETP Activity

First, low density lipoprotein (LDL) (Meridian) was biotinylated by incubating LDL with biotin for 1 hour on ice, after which it was dialyzed to remove free biotin. Then compounds at varying concentrations were incubated with 15 nM CETP (reagent production group, In Vitro Pharmacology, MRL Rahway) and 50 ug/ml of the biotinylated LDL in 50 mM HEPES, 150 mM NaCl, pH 7.4, for 1 hour at 37° C. The reaction was started by adding 3H-cholesterol ester high density lipoprotein (HDL) (American Radiochemicals Corp) at a concentration of ~0.6 nM. The reaction proceeded for 2 hours at 37° C., after which time it was quenched by the addition of 12% acetic acid. PVT streptavadin-coated scintillation proximity beads, which had been brought to room temperature, were then added at a concentration of 4 mg/ml. The assay was then mixed and counted after one half hour in a Microbeta plate reader.

In Vitro Radioactive Assays of CETP-Catalyzed CE and TG Transfer (RTA Assay)

Reagents and sources are: [3H] cholesteryl oleate (GE #TRK.886), [3H] Triolein (Perkin-Elmer NET-431), Butylated hydroxyl toluene (Aldrich, #D4740-4), DOPC (Sigma, # P6354), Sodium Bromide (Fisher scientific #S255-500), PEG 8000 (Fisher, #BP233-1), and human HDL (Intracel Corp #RP-036).

An in vitro assay for determining $IC_{50}$'s to identify compounds that inhibit CETP transfer activity is performed based on a modification of a published method (Morton and Zilversmit, (1981) A plasma inhibitor of triglyceride and cholesteryl ester transfer activities, J. Biol. Chem. 256(23), 11992-11995). The ability of inhibitors to alter CETP activity is performed using two different assays: one using recombinant CETP and one using an endogenous plasma source of CETP. Both assays measure the transfer of [3H] cholesteryl oleate or [3H] triolein from exogenous LDL to HDL.

Radiolabeled donor particles are generated by first combining 100 µl of 200 µM butylated hydroxyl toluene in $CHCl_3$, 216 µL of 21.57 mM DOPC in EtOH, and either 500 µCi [3H]-triolein (Perkin Elmer #NET-431) or 500 µCi [3H]-cholesteryl oleate (GE #TRK886) in a glass tube. Reagents are mixed, dried under nitrogen, and then resuspended in 2 mL of 50 mM Tris, 27 µM EDTA at pH 7.4. After a brief vortex, the solution is sonicated until clear and mixed with 20 mL of fresh human serum. The mixture is incubated overnight at 37° C. The [3H] labeled LDL substrate is separated at 1.063 g/ml density by sequential ultracentrifugal flotation in NaBr according to the method by (Havel, Eder et al. 1955; Chapman, Goldstein et al. 1981). Once isolated the particles are dialyzed 3x in CETP buffer (50 mM Tris, pH 7.4, 100 mM NaCl, 1 mM EDTA). Human HDL is purchased from Intracel and used as the acceptor particles.

Transfer assays are performed in a 96-well v-bottom polypropylene plate. For the RTA using recombinant CETP (2% RTA), an assay cocktail is prepared with the final concentrations 128 µg/mL HDL, 20 nM rCETP, 2% human serum, and 1×CETP buffer. 1 µL of each test compound diluted in DMSO is added to 47 µL of assay cocktail per well and incubated at 37° C. for 1 hour. To initiate the transfer reaction, 2 µL radiolabeled LDL is added. After an additional 60 min of incubation at 37° C., the transfer action is terminated by precipitation of LDL with an equal volume of 20% W/V PEG 8000. The plates are centrifuged at 2000 rpm for 30 minutes at 4° C. A 40 µL aliquot of the HDL-containing supernatant is transferred to a Packard Optiplate™ with 200 µL of MicroScint™ 20. After mixing, plates are counted by liquid scintillation. Counts present in the supernatant for blanks (wells containing only HDL acceptor, CETP buffer and DMSO) are subtracted from those containing test compounds and used to correct for non-specific transfer.

For the transfer assay using endogenous CETP from serum (95% RTA), the same procedure is used except that human serum is added such that a final concentration of serum of 95% of the total assay volume is achieved, yielding a concentration of approximately 15 nM endogenous CETP in the assay. This is then combined with HDL and CETP buffer and the reaction proceeds as above and is terminated as described.

Comparison of the counts of samples with inhibitors to an uninhibited (DMSO only) positive control yield a percent inhibition. A plot of percent inhibition vs. log of inhibitor concentration, fit to a Sigmoidal 4 parameter equation is used to calculate IC50.

EXAMPLES

The following schemes and examples are provided so that the invention will be more fully appreciated and understood. These examples are illustrative and are not to be construed as limiting the invention in any way. Starting materials are commercially available or are made using known procedures or as shown below. The examples may be synthesized using the general schemes provided below. The compounds listed as examples all have IC50 values that were measured using the RTA (2% human serum) or SPA assay between about 4 nM and 2760 nM. Examples 58-61 were assayed using the RTA in 95% human serum.

General Synthetic Scheme 1

In accordance with General Scheme 1, the cross-coupling reaction between a 2-chloroquinoxaline derivative and the corresponding boronic acid agent provides a substituted quinoxaline derivative, which is then reduced to a 1,2,3,4-tetrahydroquinoxaline derivative. Regioselective reductive amination reactions of 1,2,3,4-tetrahydroquinoxalines give alkylated 1,2,3,4-tetrahydroquinoxaline derivatives. Ring opening reactions with epoxides lead to compounds of formula (I).

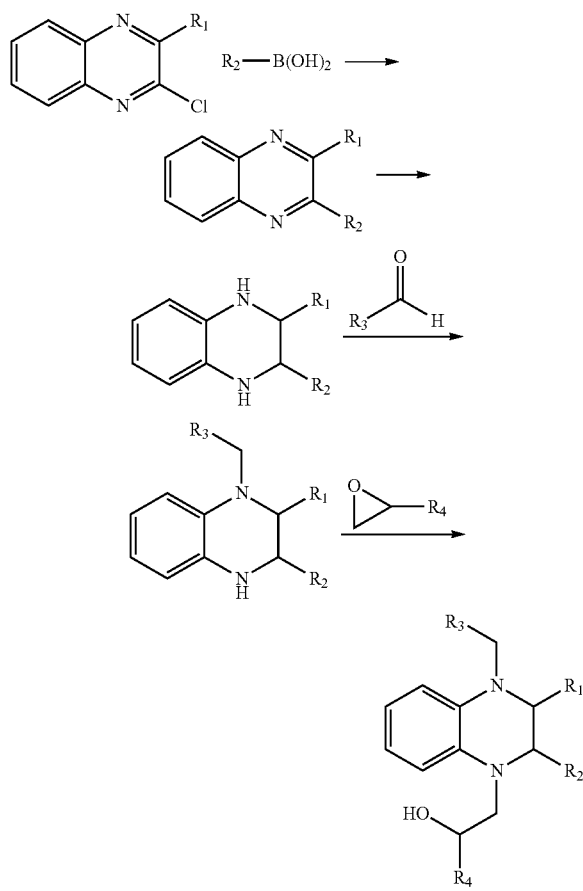

Examples

Example 1

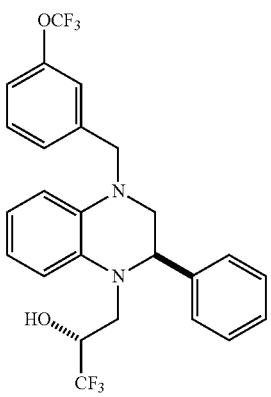 [SMILES: O[C@H](CN1c2ccccc2N(Cc2cccc(OC(F)(F)F)c2)C[C@H]1c1ccccc1)C(F)(F)F]

(R)-3-((R)-4-(3-trifluoromethoxy)-2-phenyl-3,4-dihydroquinoxalin-1(2H)-yl)-1,1,1-trifluoropropan-2-ol RTA: 19 nM Scheme A1

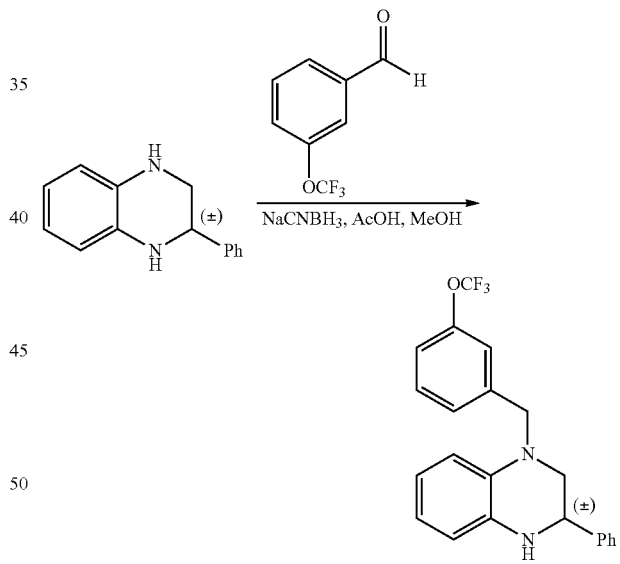

Acetic acid (0.817 mL, 14.27 mmol) was added to a solution of commercially available racemic 2-phenyl-1,2,3,4-tetrahydroquinoxaline (1 g, 4.76 mmol) and 3-trifluoromethoxy-benzaldehyde (0.884 ml, 6.18 mmol) in methanol (20 mL), followed by addition of NaCNBH$_3$ (0.389 g, 6.18 mmol). The reaction mixture was heated to 70° C. and reaction progress was followed by thin layer chromatography. The reaction was judged complete within 5 h. The reaction was quenched via the addition of saturated NH$_4$Cl. The two layers were separated and the aqueous layer was extracted with ethyl acetate. The combined organic layers were dried over magnesium sulphate and the solvent was removed in vacuo. Purification of the crude material was carried out on a normal phase Isco CombiFlash (10-50% EtOAc in hexanes, 50 g silica gel column) to give racemic 1-(3-trifluoromethoxy)benzyl-3-phenyl-1,2,3,4-tetrahydroquinoxaline. $^1$H NMR (400 MHz, CDCl$_3$) 83.40 (d, J=6.4 Hz, 2H), 4.06 (bs, 1H), 4.49 (d, J=6.0 Hz, 2H), 4.58 (t, J=4.4 Hz, 1H), 6.60 (m, 1H), 6.70 (m, 3H), 7.12 (d, J=6.4 Hz, 1H), 7.16 (s, 1H), 7.23 (d, J=6.4 Hz, 1H), 7.38 (m, 6H); MS m/z=385.21.

Scheme A2

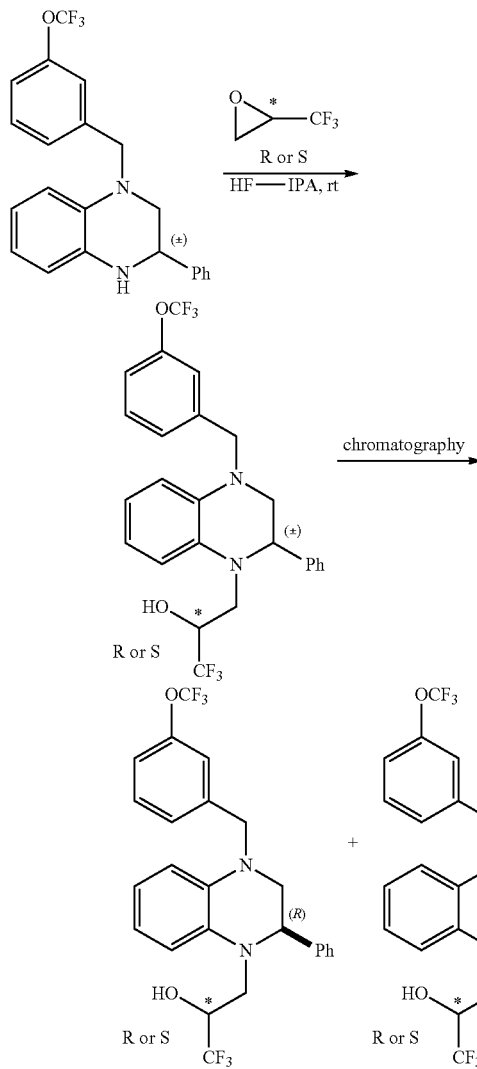

(R)-(+)-3,3,3-Trifluoro-1,2-epoxypropane (86 μL, 0.999 mmol) was added to racemic 1-(3-trifluoromethoxy)benzyl-3-phenyl-1,2,3,4-tetrahydroquinoxaline (128 mg, 0.333 mmol) in 1,1,1,3,3,3-hexafluoro-2-propanol (350 μL, 3.33 mmol), and the reaction was stirred at room temperature. After three hours, LCMS showed complete conversion. The solvent was removed in vacuo and the obtained crude mixture purified by normal phase Isco CombiFlash (10-30% EtOAc in hexanes, 25 g silica gel column), and diastereomers were separated using SFC chromatography (chiral OD column, 40% MeOH) to give faster eluting (R)-3-((S)-4-(3-trifluoromethoxy)-2-phenyl-3,4-dihydroquinoxalin-1(2H)-yl)-1,1,1-trifluoro-propan-2-ol and slower eluting (R)-3-((R)-4-(3-trifluoromethoxy)-2-phenyl-3,4-dihydroquinoxalin-1(2H)-yl)-1,1,1-trifluoro-propan-2-ol. Spectra for (R)-3-((R)-4-(3-trifluoromethoxy)-2-phenyl-3,4-dihydroquinoxalin-1(2H)-yl)-1,1,1-trifluoro-propan-2-ol correspond to: $^1$H NMR (400 MHz, CDCl$_3$) δ 3.28 (dd, J=9.2, 2.8 Hz, 1H), 3.39 (dd, J=12.4, 8.0 Hz, 1H), 3.63 (dd, J=8.8, 2.8 Hz, 1H), 3.83 (d, J=12.4 Hz, 1H), 4.24 (d, J=8.8 Hz, 1H), 4.37 (d, J=8.8 Hz, 1H), 4.42 (m, 1H), 4.87 (s, 1H), 6.56 (d, J=6.4 Hz, 1H), 6.70 (m, 2H), 6.82 (m, 2H), 6.93 (d, J=6 Hz, 1H), 7.04 (d, J=6.4 Hz, 2H), 7.22 (m, 3H), 7.33 (m, 3H), MS m/z=497.28.

Example 2

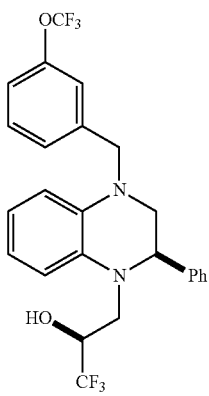 [SMILES: O[C@@H](CN1c2ccccc2N(Cc2cccc(OC(F)(F)F)c2)C[C@H]1c1ccccc1)C(F)(F)F]

RTA: 1353 nM

Scheme A3

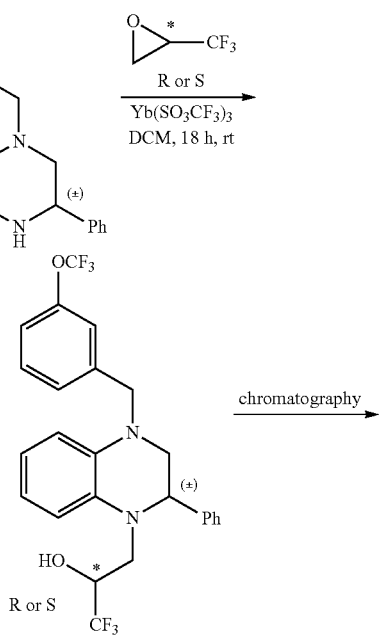

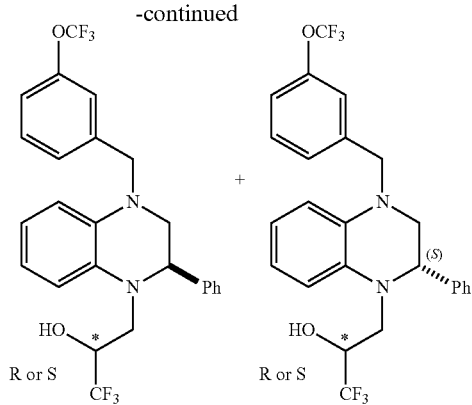

Ytterbium(III)trifluoromethanesulfonate (32.3 mg, 0.052 mmol) was added to a solution of racemic 1-(3-trifluoromethoxy)benzyl-3-phenyl-1,2,3,4-tetrahydroquinoxaline (100 mg, 0.260 mmol) and (S)-(−)-3,3,3-trifluoro 1,2-epoxypropane (112 µL, 1.3 mmol) in DCM (2 ml) and the reaction mixture was stirred at room temperature overnight. The solvent was removed in vacuo and the obtained crude mixture purified by normal phase Isco CombiFlash (10-30% EtOAc in hexanes, 25 g silica gel column) and diastereomers were separated using SFC chromatography (chiral OD column, 25% MeOH) to give faster eluting (S)-3-((S)-4-(3-trifluoromethoxy)-2-phenyl-3,4-dihydroquinoxalin-1 (2H)-yl)-1,1,1-trifluoro-propan-2-ol and slower eluting Example 2: (S)-3-((R)-4-(3-trifluoromethoxy)-2-phenyl-3,4-dihydroquinoxalin-1(2H)-yl)-1,1,1-trifluoro-propan-2-ol. $^1$H NMR (400 MHz, CDCl$_3$) δ 3.28 (dd, J=8.8, 2.0 Hz, 1H), 3.61 (dd, J=8.8, 2.4 Hz, 1H), 3.64 (d, J=8.4 Hz, 2H), 4.22 (d, J=8.8 Hz, 1H), 4.33 (q, J=2.8 Hz, 1H), 4.39 (d, J=8.8 Hz, 1H), 4.64 (s, 1H), 6.56 (d, J=6.4 Hz, 1H), 6.70 (t, J=6.0 Hz, 1H), 6.82 (m, 3H), 6.92 (d, J=6 Hz, 1H), 7.04 (d, J=6.4 Hz, 2H), 7.20 (m, 3H), 7.33 (m, 3H). MS m/z=497.29.

Example 3

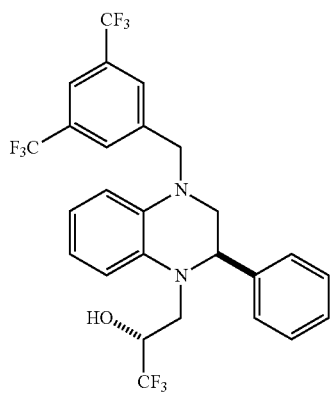

(R)-3-(R)-4-(3,5-bis(trifluoromethyl)benzyl)-2-phenyl-3,4-dihydroquinoxalin-1(2H)-yl)-1,1,1-trifluoropropan-2-ol RTA: 74 nM Example 3 was prepared in two steps from 2-phenyl-1,2,3,4-tetrahydroquinoxaline and (R)-trifluoromethylepoxide using procedures outlined in general Schemes A1 and A2 by replacing 3-trifluoromethoxybenzaldehyde with 3,5-bis(trifluoromethyl)benzaldehyde. The resulting diastereomeric mixture was purified and separated using an Isco CombiFlash (10-30% EtOAc in hexanes, 25 g silica gel column) to give faster eluting (R)-3-(S)-4-(3,5-bis(trifluoromethyl)benzyl)-2-phenyl-3,4-dihydroquinoxalin-1(2H)-yl)-1,1,1-trifluoropropan-2-ol and (R)-3-(R)-4-(3,5-bis(trifluoromethyl)benzyl)-2-phenyl-3,4-dihydroquinoxalin-1(2H)-yl)-1,1,1-trifluoropropan-2-ol. Spectra of (R)-3-(R)-4-(3,5-bis(trifluoromethyl)benzyl)-2-phenyl-3,4-dihydroquinoxalin-1(2H)-yl)-1,1,1-trifluoropropan-2-ol are as follows: $^1$H NMR (400 MHz, CDCl$_3$) δ 3.31 (dd, J=8.8, 3.2 Hz, 1H), 3.40 (dd, J=12.4, 7.6 Hz, 1H), 3.72 (dd, J=7.6, 3.2 Hz, 1H), 3.86 (d, J=12.4 Hz, 1H), 4.26 (d, J=8.8 Hz, 1H), 4.45 (m, 1H), 4.48 (d, J=8.8 Hz, 1H), 4.90 (s, 1H), 6.45 (d, J=4.4 Hz, 1H), 6.70 (m, 2H), 6.81 (t, J=5.6 Hz, 1H), 7.22 (d, J=5.6 Hz, 2H), 7.35 (m, 3H), 7.50 (s, 2H), 7.71 (s, 1H); MS m/z=549.21.

Example 4

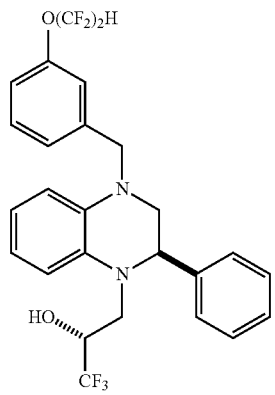

(R)-1,1,1-trifluoro-3-((R)-2-phenyl-4-(3-(1,1,2,2-tetrafluoroethoxy)benzyl)-3,4-dihydroquinoxalin-1(2H)-yl)-propan-2-ol RTA: 112 nM Example 4 was prepared in two steps from 2-phenyl-1,2,3,4-tetrahydroquinoxaline and (R)-trifluoromethylepoxide using procedures outlined in general Schemes A1 and A3 by replacing 3-trifluoromethoxybenzaldehyde with 3-(1,1,2,2-tetrafluoroethoxy)benzaldehyde. The resulting diastereomeric mixture was purified using an Isco CombiFlash (10-30% EtOAc in hexanes, 25 g silica gel column) and separated using SFC (OJ column, 15% MeOH) to give faster eluting (R)-1,1,1-trifluoro-3-((S)-2-phenyl-4-(3-(1,1,2,2-tetrafluoroethoxy)benzyl)-3,4-dihydroquinoxalin-1(2H)-yl)-propan-2-ol and the slower eluting diastereomer (R)-1,1,1-trifluoro-3-((R)-2-phenyl-4-(3-(1,1,2,2-tetrafluoroethoxy)benzyl)-3,4-dihydroquinoxalin-1(2H)-yl)-propan-2-ol. Spectra for (R)-1,1,1-trifluoro-3-((R)-2-phenyl-4-(3-(1,1,2,2-tetrafluoroethoxy)benzyl)-3,4-dihydroquinoxalin-1(2H)-yl)-propan-2-ol are as follows: $^1$H NMR (400 MHz, CDCl$_3$) 83.28 (dd, J=7.2, 2.8 Hz, 1H), 3.38 (dd, J=12.4, 7.6 Hz, 1H), 3.62 (dd, J=8.8, 2.4 Hz, 1H), 3.83 (d, J=12.4 Hz, 1H), 4.24 (d, J=12.4 Hz, 1H), 4.36 (d, J=12.4 Hz, 1H), 4.40 (m, 1H), 4.89 (s, 1H), 5.90 (t, J=40 Hz, 1H), 6.69 (d, J=6.4 Hz, 1H), 6.70 (m, 2H), 6.82 (t, J=5.6 Hz, 1H), 6.90 (m, 2H), 7.06 (d, J=6.4 Hz, 1H), 7.22 (m, 3H), 7.33 (m, 3H); MS m/z=529.23.

Example 5

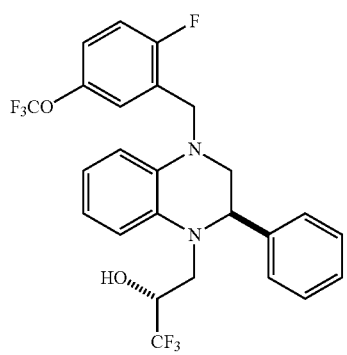 [SMILES: O[C@H](CN1c2ccccc2N(Cc2cc(OC(F)(F)F)ccc2F)C[C@H]1c1ccccc1)C(F)(F)F]

(R)-1,1,1-trifluoro-3-((R)-4-(2-fluoro-5-(trifluoromethoxy)benzyl)-2-phenyl-3,4-dihydroquinoxalin-1(2H)-yl)-propan-2-ol RTA: 11 nM Example 5 was prepared in two steps from racemic 2-phenyl-1,2,3,4-tetrahydroquinoxaline and (R)-trifluoromethyl-epoxide, using procedures outlined in general Schemes A1 and A2 by replacing 3-trifluoromethoxybenzaldehyde with 2-fluoro-5-(trifluoromethoxy)benzaldehyde. The resulting diastereomeric mixture was purified using an Isco CombiFlash (10-30% EtOAc in hexanes, 25 g silica gel column) and diastereomers were separated using SFC chromatography (chiral IA column, 15% MeOH) to give faster eluting (R)-3-((R)-4-(2-fluoro-5-(trifluoromethoxy)benzyl)-2-phenyl-3,4-dihydro quinoxalin-1 (2H)-yl)-1,1,1-trifluoropropan-2-ol and slower eluting (R)-3-((S)-4-(2-fluoro-5-(trifluoromethoxy)benzyl)-2-phenyl-3,4-dihydroquinoxalin-1 (2H)-yl)-1,1,1-trifluoropropan-2-ol. Spectra for (R)-3-((R)-4-(2-fluoro-5-(trifluoromethoxy)benzyl)-2-phenyl-3,4-dihydroquinoxalin-1 (2H)-yl)-1,1,1-trifluoropropan-2-ol are as follows: $^1$H NMR (400 MHz, CDCl$_3$) δ3.32 (dd, J=8.8, 2.8 Hz, 1H), 3.39 (dd, J=12.4, 7.6 Hz, 1H), 3.73 (dd, J=8.8, 2.4 Hz, 1H), 3.84 (d, J=12.4 Hz, 1H), 4.24 (d, J=12.4 Hz, 1H), 4.42 (m, 1H), 4.44 (d, J=12.4 Hz, 1H), 4.88 (s, 1H), 6.49 (d, J=6.4 Hz, 1H), 6.70 (m, 3H), 6.82 (t, J=5.6 Hz, 1H), 7.02 (d, J=6.4 Hz, 1H), 7.22 (d, J=5.6 Hz, 1H), 7.33 (m, 3H); MS m/z=515.22

Example 6

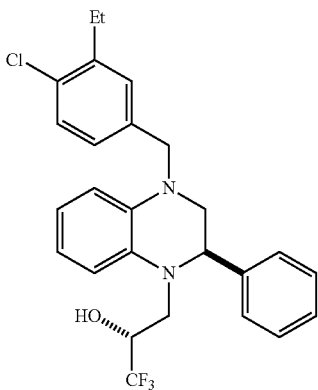 [SMILES: CCc1cc(CN2C[C@@H](c3ccccc3)N(C[C@@H](O)C(F)(F)F)c3ccccc32)ccc1Cl]

(R)-3-((R)-4-(4-chloro-3-ethylbenzyl)-2-phenyl-3,4-dihydroquinoxalin-1(2H)-yl)-1,1,1-trifluoropropan-2-ol RTA: 30 nM Example 6 was prepared in two steps from racemic 2-phenyl-1,2,3,4-tetrahydroquinoxaline and (R)-trifluoromethyl-epoxide, using procedures outlined in general Schemes A1 and A2 by replacing 3-trifluoromethoxybenzaldehyde with 4-chloro-3-ethylbenzaldehyde. The resulting diastereomeric mixture was purified using an Isco CombiFlash (10-30% EtOAc in hexanes, 25 g silica gel column) and separated using SFC chromatography (chiral IB-H column, 20% MeOH) to give faster eluting (R)-3-((R)-4-(4-chloro-3-ethylbenzyl)-2-phenyl-3,4-dihydroquinoxalin-1(2H)-yl)-1,1,1-trifluoro-propan-2-ol and (R)-3-((S)-4-(4-chloro-3-ethylbenzyl)-2-phenyl-3,4-dihydro-quinoxalin-1 (2H)-yl)-1,1,1-trifluoropropan-2-ol. Spectra of (R)-3-((R)-4-(4-chloro-3-ethylbenzyl)-2-phenyl-3,4-dihydroquinoxalin-1(2H)-yl)-1,1,1-trifluoropropan-2-ol are as follows: $^1$H NMR (400 MHz, CDCl$_3$) δ1.13 (t, J=5.6 Hz, 3H), 2.61 (q, J=5.6 Hz, 2H), 3.28 (dd, J=8.8, 3.2 Hz, 1H), 3.38 (dd, J=12.4, 7.6 Hz, 1H), 3.60 (dd, J=8.8, 3.2 Hz, 1H), 3.81 (d, J=12.4 Hz, 1H), 4.16 (d, J=12.4 Hz, 1H), 4.32 (d, J=12.4 Hz, 1H), 4.39 (m, 1H), 4.85 (s, 1H), 6.60 (d, J=6 Hz, 1H), 6.80 (m, 3H), 6.83 (m, 2H), 7.13 (d, J=6.4 Hz, 1H), 7.22 (d, J=4.8 Hz, 2H), 7.33 (m, 3H); MS m/z=475.20.

Example 7

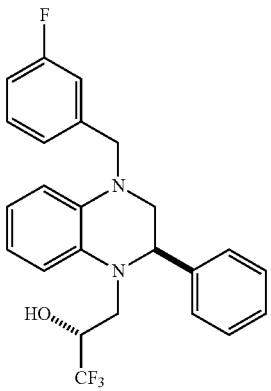

(R)-3-((R)-4-(3-fluorobenzyl)-2-phenyl-3,4-dihydroquinoxalin-1(2H)-yl)-1,1,1-trifluoropropan-2-ol RTA: 110 nM Example 7 was prepared in two steps from racemic 2-phenyl-1,2,3,4-tetrahydroquinoxaline and (R)-trifluoromethyl-epoxide, using procedures outlined in general Schemes A1 and A3 by replacing 3-trifluoromethoxybenzaldehyde with 3-fluorobenzaldehyde. The resulting diastereomeric mixture was purified using an Isco CombiFlash (10-30% EtOAc in hexanes, 25 g silica gel column) and diastereomers were separated using SFC (OD-H column, 30% EtOH) to give faster eluting (R)-3-((S)-4-(3-fluorobenzyl)-2-phenyl-3,4-dihydroquinoxalin-1(2H)-yl)-1,1,1-trifluoropropan-2-ol in 12% yield and (R)-3-((R)-4-(3q-fluorobenzyl)-2-phenyl-3,4-dihydroquinoxalin-1(2H)-yl)-1,1,1-trifluoropropan-2-ol.

Spectra of (R)-3-((R)-4-(3-fluorobenzyl)-2-phenyl-3,4-dihydroquinoxalin-1(2H)-yl)-1,1,1-trifluoropropan-2-ol are as follows: $^1$H NMR (400 MHz, CDCl$_3$) δ 3.27 (dd, J=6.0, 3.2 Hz, 1H), 3.36 (dd, J=12.8, 8 Hz, 1H), 3.61 (dd, J=9.2, 2.8 Hz, 1H), 3.83 (d, J=12.4 Hz, 1H), 4.22 (d, J=12.8 Hz, 1H), 4.35 (d, J=8.8 Hz, 1H), 4.42 (m, 1H), 4.91 (s, 1H), 6.58 (d, J=6 Hz, 1H), 6.67 (d, J=9.2 Hz, 1H), 6.71 (d, J=6.4 Hz, 2H), 6.85 (m, 3H), 7.20 (q, J=4.8 Hz, 2H), 7.23 (d, J=6.0 Hz, 2H), 7.34 (s, 3H); MS m/z=430.31.

Example 8

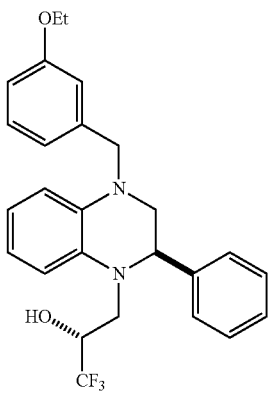 [SMILES: CCOc1cccc(CN2C[C@@H](c3ccccc3)N(C[C@@H](O)C(F)(F)F)c3ccccc32)c1]

(R)-3-((R)-4-(3-ethoxybenzyl)-2-phenyl-3,4-dihydroquinoxalin-1(2H)-yl)-1,1,1-trifluoropropan-2-ol RTA: 301 nM Example 8 was prepared in two steps from racemic 2-phenyl-1,2,3,4-tetrahydroquinoxaline and (R)-trifluoromethylepoxide, using procedures outlined in general Schemes A1 and A3 by replacing 3-trifluoromethoxybenzaldehyde with 3-ethoxybenzaldehyde. The resulting diastereomeric mixture was purified using a normal phase Isco CombiFlash (10-30% EtOAc in hexanes, 25 g silica gel column) and separated using SFC chromatography (chiral OJ column, 15% MeOH) to give faster eluting (R)-3-((R)-4-(3-ethoxybenzyl)-2-phenyl-3,4-dihydroquinoxalin-1(2H)-yl)-1,1,1-trifluoro-propan-2-ol and slower eluting (R)-3-((S)-4-(3-ethoxybenzyl)-2-phenyl-3,4-dihydroquinoxalin-1(2H)-yl)-1,1,1-trifluoro-propan-2-ol. Spectra of (R)-3-((R)-4-(3-ethoxybenzyl)-2-phenyl-3,4-dihydroquinoxalin-1(2H)-yl)-1,1,1-trifluoropropan-2-ol are as follows: $^1$H NMR (400 MHz, CDCl$_3$) δ1.38 (t, J=5.6 Hz, 3H), 3.30 (dd, J=9.2, 3.2 Hz, 1H), 3.36 (dd, J=12.4, 7.6 Hz, 1H), 3.60 (dd, J=9.2, 3.2 Hz, 1H), 3.84 (m, 3H), 4.24 (d, J=12.4 Hz, 1H), 4.32 (d, J=12.4 Hz, 1H), 4.38 (m, 1H), 4.82 (s, 1H), 6.70 (m, 6H), 6.80 (t, J=6.0 Hz, 1H), 7.11 (t, J=6.0 Hz, 1H), 7.22 (d, J=5.4 Hz, 1H), 7.33 (m, 3H); MS m/z=457.30.

Example 9

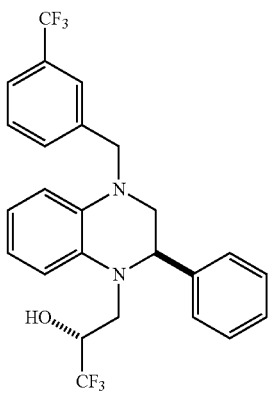

(R)-3-((R)-4-(3-ethoxybenzyl)-2-phenyl-3,4-dihydroquinoxalin-1(2H)-yl)-1,1,1-trifluoropropan-2-ol RTA: 47 nM Example 9 was prepared in two steps from racemic 2-phenyl 1,2,3,4-tetrahydroquinoxaline and (R)-trifluoromethylepoxide, using procedures outlined in general Schemes A1 and A3 by replacing 3-trifluoromethoxy benzaldehyde with 3-trifluoromethylbenzaldehyde. The resulting diastereomeric mixture was purified using a normal phase Isco CombiFlash (10-30% EtOAc in hexanes, 25 g silica gel column), and diastereomers were separated using SFC (OD-H column, 30% EtOH) to give faster eluting (R)-3-((S)-4-(3-trifluoromethylbenzyl)-2-phenyl-3,4-dihydroquinoxalin-1 (2H)-yl)-1,1,1-trifluoro-propan-2-ol and slower eluting (R)-3-((R)-4-(3-trifluoromethylbenzyl)-2-phenyl-3,4-dihydroquinoxalin-1(2H)-yl)-1,1,1-trifluoropropan-2-ol. Spectra of (R)-3-((R)-4-(3-trifluoromethylbenzyl)-2-phenyl-3,4-dihydroquinoxalin-1(2H)-yl)-1,1,1-trifluoropropan-2-ol are as follows: $^1$H NMR (400 MHz, CDCl$_3$) δ3.27 (dd, J=9.1, 2.8 Hz, 1H), 3.36 (dd, J=12.0, 8 Hz, 1H), 3.63 (dd, J=9.2, 2.8 Hz, 1H), 3.83 (d, J=12.8 Hz, 1H), 4.24 (d, J=12.8 Hz, 1H), 4.44 (d, J=12.8 Hz, 2H), 4.88 (s, 1H), 6.56 (d, J=6.4 Hz, 1H), 6.70 (m, 2H), 6.83 (t, J=5.6 Hz, 1H), 7.12 (d, J=6 Hz, 1H), 7.33 (m, 8H), 7.44 (d, J=6 Hz, 1H); MS m/z=481.29.

Scheme A4

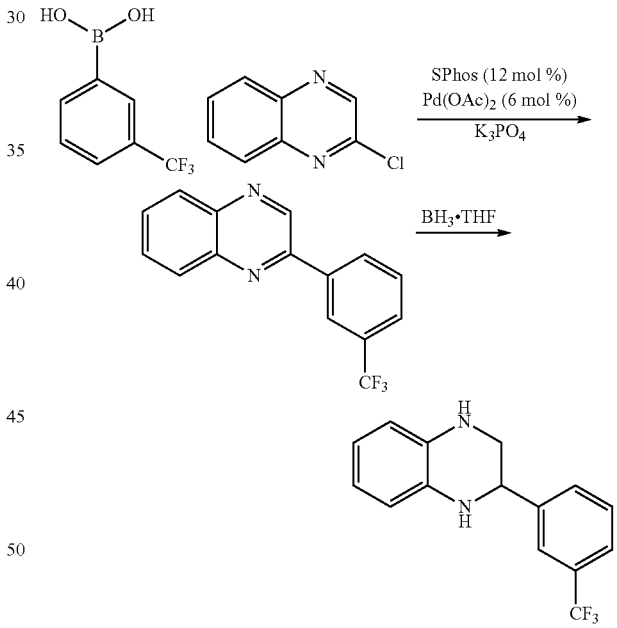

A vial was charged with potassium phosphate (3.87 g, 18.23 mmol), palladium acetate (0.123 g, 0.547 mmol), 2-chloroquinoxaline (1.5 g, 9.11 mmol), 3-trifluromethylphenyl boronic acid (2.250 g, 11.85 mmol) and S-Phos (0.449 g, 1.094 mmol) and the whole system was placed under vacuum and backfilled with nitrogen three times. The solvents THF (10 mL) and water (3 mL) were degassed with nitrogen and added to the reaction system. The reaction mixture was sparged for ten minutes and then heated to 75° C. overnight. The reaction was quenched by the addition of saturated NH$_4$Cl. The two layers were separated and the aqueous layer extracted with ethyl acetate. The combined organic layers were dried over magnesium sulphate and the solvent was removed in vacuo. Purification of the obtained crude material was carried out on an Isco CombiFlash (10-30% EtOAc in hexanes, 100 g silica gel column) to give 2-(3-trifluoromethylphenyl)-1,2,3,4-tetrahydroquinoxaline (1.9 g, 6.93 mmol) as an off-white solid. $^1$H NMR (400 MHz, CDCl$_3$) 87.73 (t, J=6.0 Hz, 1H), 7.85 (m, 3H), 8.18 (d, J=6.4 Hz, 1H), 8.21 (d, J=6.4 Hz, 1H), 8.41 (d, J=6.4 Hz, 1H), 8.54 (s, 1H), 9.30 (s, 1H).

Borane-THF complex (12.84 mL, 12.84 mmol) was added dropwise to a solution of 2-(3-trifluoromethylphenyl)-1,2,3,4-tetrahydroquinoxaline (1.6 g, 5.83 mmol) in THF (20 mL) at room temperature. The reaction was followed by thin layer chromatography. After 4 hours the reaction was judged complete and the reaction was quenched by the addition of saturated NH$_4$Cl and partitioned between EtOAc and 1N K$_2$CO$_3$. The two layers were separated and the aqueous layer further extracted with ethyl acetate. The combined organic layers were dried over magnesium sulphate and solvent was removed in vacuo. Purification of the obtained crude material was carried out on a normal phase Isco CombiFlash (10-30% EtOAc in hexanes, 50 g silica gel column) to give 2-(3-trifluoromethyl-phenyl)-1,2,3,4-tetrahydroquinoxaline. $^1$H NMR (400 MHz, CDCl$_3$) δ 3.35 (dd, J=8.8, 6.8 Hz, 1H), 3.50 (dd, J=8.8, 2.4 Hz, 1H), 3.95 (brs, 1H), 4.58 (dd, J=6.4, 2.4 Hz, 1H), 6.64 (m, 2H), 6.69 (m, 2H), 7.51 (t, J=6.4 Hz, 1H), 7.61 (d, J=6.4 Hz, 2H), 7.69 (s, 1H); MS m/z=279.3.

Example 10

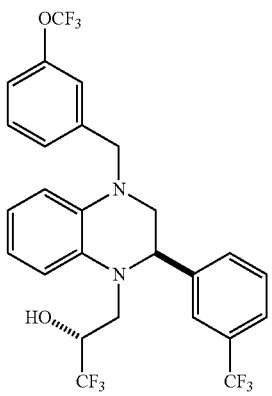 [SMILES: O[C@H](CN1c2ccccc2N(Cc2cccc(OC(F)(F)F)c2)C[C@H]1c1cccc(C(F)(F)F)c1)C(F)(F)F]

(R)-1,1,1-trifluoro-3-((R)-4-(3-trifluoromethoxy)benzyl)-2-(3-(trifluoromethyl)phenyl)-3,4-dihydro-quinoxalin-1(2H)-yl)propan-2-ol SPA: 9 nM Example 10 was prepared in two steps from 2-(3-trifluoromethyl-phenyl)-1,2,3,4-tetrahydroquinoxaline, prepared according to scheme A4, using procedures outlined in general Schemes A1 and A2. The resulting diastereomeric mixture was purified using an Isco CombiFlash (10-30% EtOAc in hexanes, 25 g silica gel column) and diastereomers were separated using reverse phase Gilson chromatography to give the faster eluting diastereomer (R)-1,1,1-trifluoro-3-((S)-4-(3-trifluoromethoxy)benzyl)-2-(3-(trifluoromethyl)phenyl)-3,4-dihydroquinoxalin-1(2H)-yl)propan-2-ol and the slower eluting desired diastereomer (R)-1,1,1-trifluoro-3-((R)-4-(3-trifluoromethoxy)benzyl)-2-(3-(trifluoromethyl)phenyl)-3,4-dihydro-quinoxalin-1(2H)-yl)propan-2-ol. Spectra of (R)-1,1,1-trifluoro-3-((R)-4-(3-trifluoromethoxy)benzyl)-2-(3-(trifluoromethyl)phenyl)-3,4-dihydroquinoxalin-1(2H)-yl)propan-2-ol are as follows: $^1$H NMR (400 MHz, CDCl$_3$) 83.22 (dd, J=9.2, 2.8 Hz, 1H), 3.33 (dd, J=12.4, 8.4 Hz, 1H), 3.59 (dd, J=9.2, 2.8 Hz, 1H), 3.88 (d, J=12.8 Hz, 1H), 4.18 (d, J=12.8 Hz, 1H), 4.42 (d, J=12.8 Hz, 2H), 4.50 (m, 1H), 5.00 (s, 1H), 6.62 (d, J=6.4 Hz, 1H), 6.70 (m, 2H), 6.80 (s, 1H), 6.86 (t, J=5.6 Hz, 1H), 6.90 (d, J=6.0 Hz, 1H), 7.05 (d, J=6.4 Hz, 1H), 7.20 (t, J=6.4 Hz, 1H), 7.42 (d, J=6.4 Hz, 1H), 7.47 (m, 2H), 7.60 (d, J=6.0 Hz, 1H); MS m/z=565.13.

Example 11

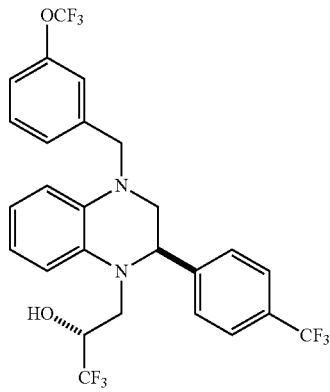 [SMILES: O[C@H](CN1c2ccccc2N(Cc2cccc(OC(F)(F)F)c2)C[C@H]1c1ccc(C(F)(F)F)cc1)C(F)(F)F]

(R)-1,1,1-trifluoro-3-((R)-4-(3-trifluoromethoxy)benzyl)-2-(4-(trifluoromethyl)phenyl)-3,4-dihydro-quinoxalin-1(2H)-yl)propan-2-ol SPA: 4 nM The precursor 2-(4-trifluoromethyl-phenyl)-1,2,3,4-tetrahydroquinoxaline was prepared according to general scheme A4 by replacing 3-(trifluoromethyl)phenylboronic acid with 4-(trifluoromethyl)phenylboronic acid. Example 11 was prepared in two steps using procedures outlined in general Schemes A1 and A2. The resulting diastereomeric mixture was purified using a normal phase Isco CombiFlash (10-30% EtOAc in hexanes, 25 g silica gel column) and diastereomers were separated using reverse phase Gilson chromatography to give the faster eluting diastereomer (R)-1,1,1-trifluoro-3-((S)-4-(4-trifluoromethoxy)benzyl)-2-(3-(trifluoro-methyl)phenyl)-3,4-dihydroquinoxalin-1(2H)-yl)propan-2-ol and the slower eluting diastereomer (R)-1,1,1-trifluoro-3-((R)-4-(4-trifluoromethoxy)benzyl)-2-(3-(trifluoro-methyl)phenyl)-3,4-dihydro-quinoxalin-1(2H)-yl)propan-2-ol. Spectra of (R)-1,1,1-trifluoro-3-((R)-4-(4-trifluoromethoxy)benzyl)-2-(3-(trifluoromethyl)phenyl)-3,4-di-hydro-quinoxalin-1(2H)-yl)propan-2-ol are as follows: $^1$H NMR (400 MHz, CDCl$_3$) δ 3.24 (dd, J=9.2, 2.8 Hz, 1H), 3.32 (dd, J=12.4, 8.4 Hz, 1H), 3.61 (dd, J=9.2, 2.8 Hz, 1H), 3.87 (d, J=12.8 Hz, 1H), 4.17 (d, J=12.8 Hz, 1H), 4.42 (d, J=12.8 Hz, 2H), 4.49 (m, 1H), 4.97 (s, 1H), 6.61 (d, J=6.4 Hz, 1H), 6.70 (d, J=6.4 Hz, 2H), 6.83 (m, 3H), 6.05 (t, J=6.4 Hz, 1H), 7.17 (t, J=6.4 Hz, 1H), 7.30 (m, 2H), 7.60 (d, J=6.4 Hz, 2H); MS m/z=565.11.

Examples 12/13

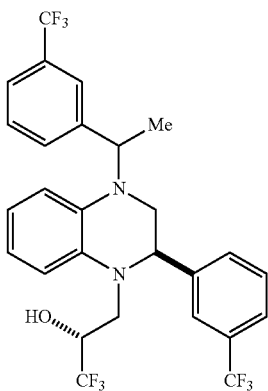 [SMILES: CC(c1cccc(C(F)(F)F)c1)N1C[C@@H](c2cccc(C(F)(F)F)c2)N(C[C@@H](O)C(F)(F)F)c2ccccc21]

(R)-1,1,1-trifluoro-3-((R)-2-(3-(trifluoromethyl)phenyl-4-(1-(3-trifluoromethyl)phenyl)ethyl)-3,4-dihydroquinoxalin-1(2H)-yl)propan-2-ol Scheme A5

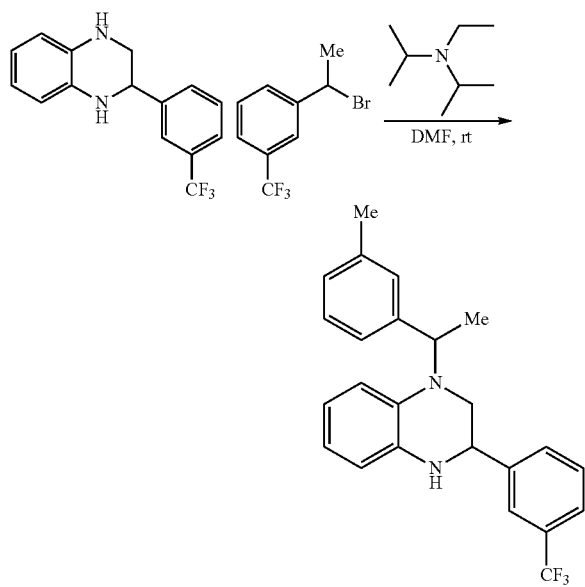

Hunig's Base (0.138 mL, 0.791 mmol) was added to racemic 2-(3-trifluoromethylphenyl)-1,2,3,4-tetrahydroquinoxaline (200 mg, 0.791 mmol) in DMF (5 mL) and left to stir at room temperature for 10 min. Then 1-bromo-1-(3-trifluoromethyl)phenyl)ethane (0.11 mL, 0.65 mmol) was added. The reaction was stirred at room temperature overnight. The reaction was then quenched via the addition of NH$_4$Cl. The two layers were separated and the aqueous layer was extracted with ethyl acetate. The combined organic layers were dried over magnesium sulphate, and the solvent was removed in vacuo. Purification of the obtained crude material was carried out on a normal phase Isco CombiFlash (10-50% EtOAc in hexanes, 25 g silica gel column) to give the faster eluting diastereomer 3-(3-(trifluoromethyl)phenyl-1-(1-(3-trifluoromethyl)phenyl)ethyl-1,2,3,4-tetrahydroquinoxaline and the slower eluting diastereomer. Spectral data of the faster eluting diastereomer are as follows: $^1$H NMR (400 MHz, CDCl$_3$) δ 1.58 (d, J=5.6 Hz, 3H), 3.07 (d, J=8.0 Hz, 2H), 4.03 (s, 1H), 4.39 (t, J=4.4 Hz, 1H), 5.20 (q, J=5.6 Hz, 1H), 6.78 (m, 4H), 7.50 (m, 8H); MS m/z=451.19; and spectral data of the slower eluting diastereomer are as follows: $^1$H NMR (400 MHz, CDCl$_3$) 81.62 (d, J=5.6 Hz, 3H), 2.99 (m, 1H), 3.34 (d, J=8 Hz, 1H), 4.16 (s, 1H), 4.56 (s, 1H), 5.11 (q, J=5.6 Hz, 1H), 6.78 (m, 4H), 7.2 (m, 2H), 7.48 (m, 6H); MS m/z=451.19.

Example 12

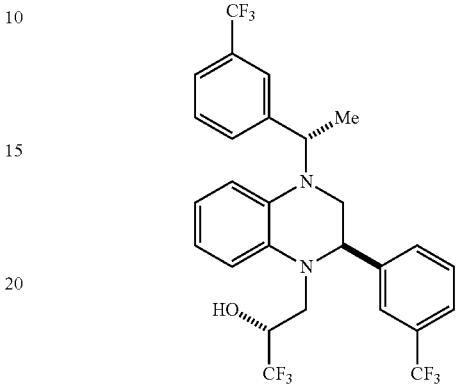

(R)-1,1,1-trifluoro-3-((R)-2-(3-(trifluoromethyl)phenyl-4-(S)-1-(3-trifluoromethyl)phenyl)ethyl)-3,4-dihydroquinoxalin-1(2H)-yl)propan-2-ol SPA: 28 nM Examples 12 and 13 were prepared from 3-(3-(trifluoromethyl)phenyl-1-(1-(3-trifluoromethyl)phenyl)ethyl-1,2,3,4-tetrahydroquinoxaline using general procedure A2. The crude mixture was purified by Isco normal phase chromatography, followed by separation of diastereomers achieved by SFC chromatography (IB column, 5% MeOH). The spectral data of the fastest eluting diastereomer, example 12, (R)-1,1,1-trifluoro-3-((R)-2-(3-(trifluoromethyl)phenyl-4-((S)-(1-(3-trifluoromethyl)phenyl)ethyl)-3,4-dihydroquinoxalin-1 (2H)-yl)propan-2-ol are as follows: $^1$H NMR (400 MHz, DMSO) δ 1.02 (d, J=5.6 Hz, 3H), 3.10 (dd, J=12.4, 8.0 Hz, 1H), 3.29 (m, 1H), 3.59 (d, J=9.6 Hz, 1H), 3.78 (d, J=12.4 Hz, 1H), 4.28 (m, 1H), 4.93 (q, J=5.6 Hz, 1H), 5.07 (s, 1H), 6.58 (m, 5H), 7.44 (d, J=6.0 Hz, 1H), 7.58 (m, 6H); MS m/z=563.19.

Example 13

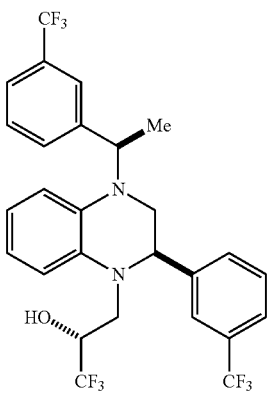 [SMILES: C[C@H](c1cccc(C(F)(F)F)c1)N1C[C@@H](c2cccc(C(F)(F)F)c2)N(C[C@@H](O)C(F)(F)F)c2ccccc21]

(R)-1,1,1-trifluoro-3-((R)-2-(3-(trifluoromethyl)phenyl-4-((R)-1-(3-trifluoromethyl)phenyl)ethyl)-3,4-dihydroquinoxalin-1(2H)-yl)propan-2-ol SPA: 10 nM Spectral data of the second slowest diastereomer, Example 13, (R)-1,1,1-trifluoro-3-((R)-2-(3-(trifluoromethyl)phenyl-4-((R)-(1-(3-trifluoromethyl)phenyl)ethyl)-3,4-dihydroquinoxalin-1(2H)-yl)propan-2-ol are as follows: $^1$H NMR (400 MHz, DMSO) δ 1.41 (d, J=5.6 Hz, 3H), 2.90 (d, J=9.2 Hz, 1H), 3.00 (dd, J=12.4, 7.6 Hz, 1H), 3.32 (d, J=7.6 Hz, 1H), 3.78 (d, J=12.4 Hz, 1H), 4.28 (t, J=6.0 Hz, 1H), 4.98 (s, 1H), 5.06 (q, J=5.6 Hz, 1H), 6.60 (m, 2H), 6.72 (t, J=6.0 Hz, 1H), 6.84 (d, J=6.0 Hz, 1H), 7.02 (d, J=6.0 Hz, 1H), 7.15 (m, 2H), 7.22 (m, 2H), 7.83 (m, 2H), 7.50 (d, J=6 Hz, 1H); MS m/z=563.19.

Example 14

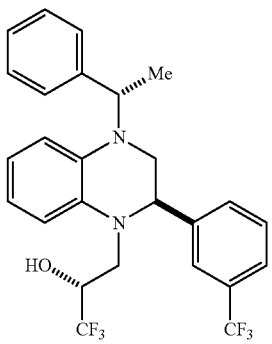 [SMILES: C[C@@H](c1ccccc1)N1C[C@@H](c2cccc(C(F)(F)F)c2)N(C[C@@H](O)C(F)(F)F)c2ccccc21]

(R)-1,1,1-trifluoro-3-((R)-4-((S)-1-phenylethyl)-2-(3-trifluoromethyl)phenyl)-3,4-dihydroquinoxalin-1(2H)-yl)propan-2-ol SPA: 1455 nM Example 14 was prepared in two steps from racemic 2-(3-trifluoromethylphenyl)-1,2,3,4-tetrahydroquinoxaline using procedures outlined in general Schemes A5 and A2 by replacing 1-bromo-1-(3-trifluoromethyl)phenyl)ethane with 1-bromo-1-phenylethane. Separation of diastereomers was achieved through further reverse phase Gilson purification. Spectral data for Example 14, (R)-1,1,1-trifluoro-3-((R)-4-((S)-1-phenylethyl)-2-(3-trifluoromethyl)phenyl)-3,4-dihydroquinoxalin-1(2H)-yl)propan-2-ol, correspond to: $^1$H NMR (400 MHz, DMSO) δ 0.96 (d, J=5.6 Hz, 3H), 3.09 (dd, J=12.4, 8.0 Hz, 1H), 3.28 (m, 1H), 3.52 (d, J=9.6 Hz, 1H), 3.78 (m, 1H), 4.29 (m, 1H), 4.84 (m, 1H), 5.05 (s, 1H), 6.65 (m, 4H), 7.34 (m, 8H), 7.60 (d, J=6 Hz, 1H); MS m/z=495.20.

Example 15

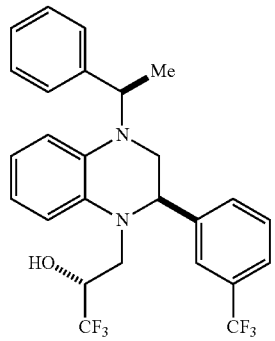 [SMILES: C[C@H](c1ccccc1)N1C[C@@H](c2cccc(C(F)(F)F)c2)N(C[C@@H](O)C(F)(F)F)c2ccccc21]

(R)-1,1,1-trifluoro-3-((R)-4-((R)-1-phenylethyl)-2-(3-trifluoromethyl)phenyl)-3,4-dihydroquinoxalin-1(2H)-yl)propan-2-ol SPA: 14 nM Spectral data of Example 15 (R)-1,1,1-trifluoro-3-((R)-4-(R)-1-phenylethyl)-2-(3-trifluoromethyl)phenyl)-3,4-dihydroquinoxalin-1(2H)-yl)propan-2-ol are as follows: $^1$H NMR (400 MHz, DMSO) δ 1.35 (d, J=5.6 Hz, 3H), 2.83 (d, J=9.2 Hz, 1H), 3.00 (dd, J=12.4, 7.6 Hz, 1H), 3.17 (d, J=7.6 Hz, 1H), 3.75 (d, J=12.4 Hz, 1H), 4.94 (m, 2H), 6.59 (m, 2H), 6.70 (m, 3H), 6.82 (d, J=6.0 Hz, 1H), 6.88 (t, J=6.0 Hz, 2H), 7.00 (t, J=6.0 Hz, 1H), 7.22 (m, 2H), 7.41 (t, J=6.0 Hz, 1H), 7.56 (d, J=6.0 Hz, 1H); MS m/z=495.20.

Scheme A6

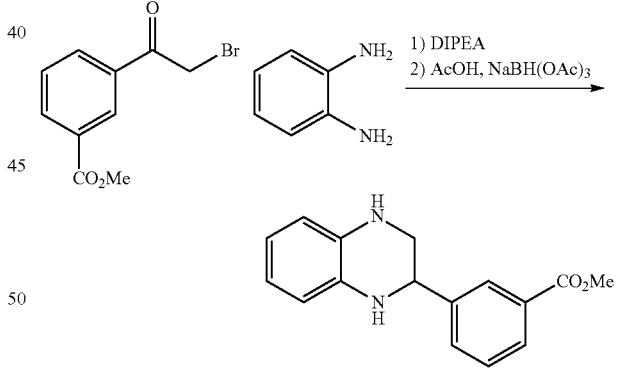

1,2-phenylenediamine (300 mg, 2.77 mmol) was dissolved in 2.7 mL MeCN. Hunig's Base (485 μl, 2.77 mmol) was added, followed by methyl 3-(2-bromoacetyl)benzoate (713 mg, 2.77 mmol). The resulting reaction mixture was stirred at room temperature for 30 minutes. Acetic acid (476 μl, 8.32 mmol) and sodium triacetoxyborohydride (1176 mg, 5.55 mmol) were added. The mixture was stirred at r.t. overnight. TLC indicated that the starting material was consumed, and the reaction was quenched with saturated ammonium chloride and extracted into DCM. The organic phase was dried with MgSO$_4$, filtered, concentrated, and purified on a 100 g silica column with 0-30% EtOAc/hexanes gradient to give methyl 3-(1,2,3,4-tetrahydroquinoxalin-2-yl)benzoate.

Example 16

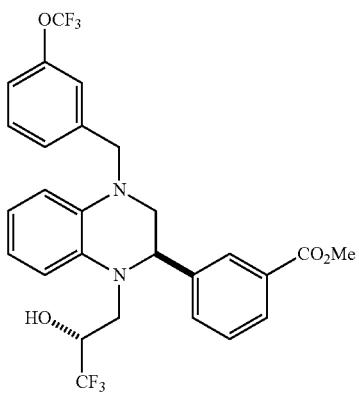 [SMILES: COC(=O)c1cccc([C@@H]2CN(Cc3cccc(OC(F)(F)F)c3)c3ccccc3N2C[C@@H](O)C(F)(F)F)c1]

Methyl-3-((R)-1-(R-3,3,3-trifluoro-2-hydroxypropyl)-4-(3-trifluoromethoxy)benzyl)-1,2,3,4-tetrahydroquinoxalin-2-yl)benzoate SPA: 27 nM Example 16 was prepared in three steps from commercially available methyl 3-(bromoacetyl)benzoate using procedures outlined in general Schemes A6, A1, and A2. Spectral data are as follows: $^1$H NMR (400 MHz, CDCl$_3$) δ 3.25 (dd, J=11.4, 3.6 Hz, 1H), 3.32 (dd, J=15.5, 9.6 Hz, 1H), 3.58 (dd, J=11.4, 3.4 Hz, 1H), 3.85 (d, J=15.4 Hz, 1H), 3.92 (s, 3H) 4.19 (d, J=15.8 Hz, 1H), 4.39 (d, J=15.8 Hz, 1H), 4.45 (m, 1H), 4.99 (t, J=3.3 Hz, 1H), 6.58 (d, J=7.9 Hz, 1H), 6.70 (m, 2H), 6.80 (s, 1H), 6.84 (t, J=7.7 Hz, 1H), 6.93 (d, J=7.7 Hz, 1H), 7.03 (d, J=8.3 Hz, 1H), 7.19 (t, J=7.9 Hz, 1H), 7.41 (m, 2H), 7.90 (s, 1H), 7.99 (t, J=4.4 Hz, 1H), MS m/z=555.01.

Scheme A7

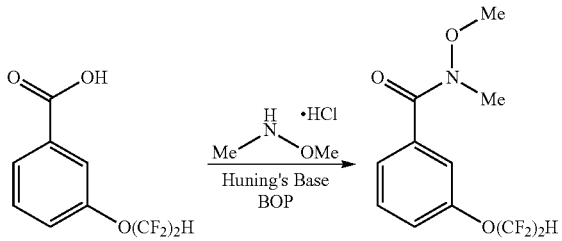

3-(1,1,2,2-tetrafluoroethoxy)benzoic acid (10 g, 42.0 mmol) was dissolved in DMF (200 mL) and Hunig's Base (20.54 mL, 118 mmol). Benzotriazol-1-yl-oxy-tris-(dimethylamino)phosphonium hexafluorophosphate (BOP, 27.9 g, 63.0 mmol) and N-methoxy-N-methylamine hydrochloride (4.51 g, 46.2 mmol) were added to the reaction flask, and the resulting reaction mixture was stirred at 25° C. overnight. Crude reaction mixture was concentrated and purified on a silica gel column (340 g cartridge 0-10% EtOAc/Hexanes gradient) to afford N-methoxy-N-methyl-3-(1,1,2,2-tetrafluoroethoxy)benzamide. $^1$H NMR (400 MHz, CDCl$_3$) δ 3.38 (s, 3H), 3.57 (s, 3H), 5.95 (t, J=52.9, 2.9 Hz, 1H), 7.33 (d, J=8.1 Hz, 1H), 7.45 (t, J=7.9 Hz, 1H), 7.58 (s, 1H), 7.63 (d, J=7.7 Hz, 1H).

Scheme A8

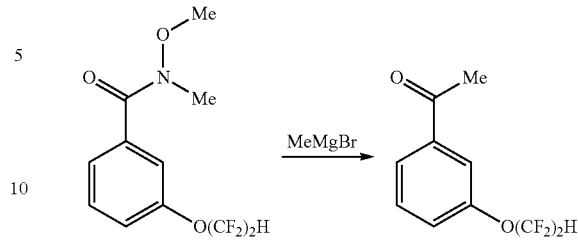

N-methoxy-N-methyl-3-(1,1,2,2-tetrafluoroethoxy)benzamide (7.5 g, 25.2 mmol) was dissolved in THF (84 mL) and cooled to −78° C. Methyl magnesium bromide (3N in diethyl ether, 21.03 mL, 63.1 mmol) was added dropwise and the resulting reaction mixture was stirred for 30 min. The reaction was warmed to 25° C. over 30 minutes and then was quenched by addition to an Erlenmeyer flask containing ice and saturated ammonium chloride solution. This mixture was extracted with EtOAc, the organic layers were collected and dried with anhydrous magnesium sulfate, then filtered and concentrated. Crude material obtained corresponds to 1-[3-(1,1,2,2-tetrafluoroethoxy)phenyl]ethanone. 1H NMR (400 MHz, CDCl3) δ 2.62 (s, 3H), 5.96 (t, t, J=53, 2.7 Hz, 1H), 7.43 (d, J=8.1 Hz, 1H), 7.51 (t, J=8.0 Hz, 1H), 7.80 (s, 1H), 7.88 (d, J=7.8 Hz, 1H).

Scheme A9

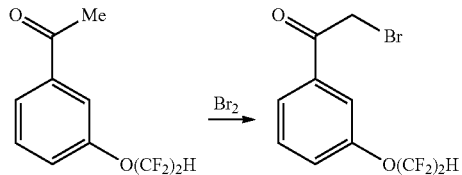

1-[3-(1,1,2,2-tetrafluoroethoxy)phenyl]ethanone (6.1 g, 25.8 mmol) was dissolved in diethyl ether (36.9 mL), and acetic acid (44.4 mL, 775 mmol) was added, followed by bromine (1.397 mL, 27.1 mmol). The reaction was stirred at 25° C. for 3 hours, then was diluted with DCM and extracted with saturated sodium bicarbonate solution. The combined organic layers were dried with anhydrous MgSO$_4$, filtered, and concentrated. The crude product was purified on a silica gel column with a 340 g cartridge, using a 10% EtOAc/Hexanes isocratic mobile phase. 2-Bromo-1-[3-(1,1,2,2-tetrafluoroethoxy)phenyl]ethanone (5 g, 15.87 mmol) was obtained. $^1$H NMR (400 MHz, CDCl$_3$) 84.45 (s, 2H), 5.96 (t, J=53, 2.7 Hz, 1H), 7.47 (d, J=8.2 Hz, 1H), 7.55 (t, J=7.9 Hz, 1H), 7.83 (s, 1H), 7.91 (d, J=7.7 Hz, 1H).

Scheme A10

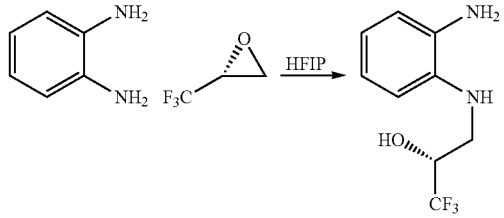

Benzene-1,2-diamine (4.83 g, 44.6 mmol) was dissolved in hexafluoroisopropanol (9.37 mL, 89 mmol), (R)-trifluoromethylepoxide (0.769 mL, 8.92 mmol) was added, and the resulting reaction mixture was stirred at room temperature for 4 hours. The solution was concentrated and purified on a silica gel column with a 0-100% EtOAc/Hexanes gradient in a 100 g cartridge. (R)-3-[(2-aminophenyl)amino]-1,1,1-trifluoropropan-2-ol (1.30 g, 5.90 mmol) was obtained in 66.2% yield. $^{1}$H NMR (400 MHz, CDCl$_3$) 83.32 (dd, J=13.4, 8.3 Hz, 1H), 3.55 (dd, J=13.5, 3.3 Hz, 1H), 3.55 (bs, 3H), 4.22 (m, 1H), 6.71 (d, J=7.7 Hz, 1H), 6.79 (m, 2H), 6.87 (d, d, J=7.7, 2.2 Hz, 1H). MS m/z=221.00

Example 17

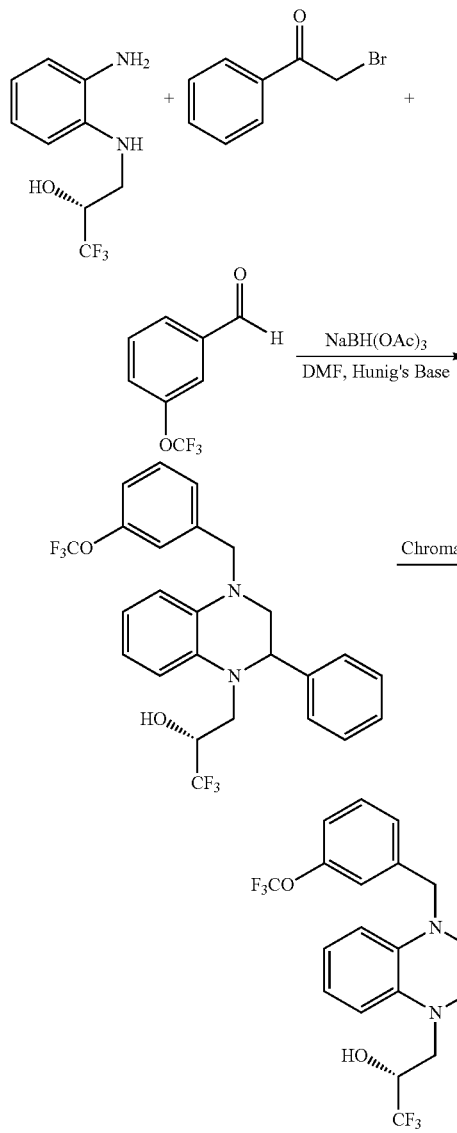

RTA: 34 nM (R)-3-[(2-aminophenyl)amino]-1,1,1-trifluoropropan-2-ol (133 mg, 0.603 mmol) was dissolved in DMF (5024 µl). 2-Bromo-1-phenylethanone (100 mg, 0.502 mmol) and Hunig's Base (88 µl, 0.502 mmol) were added and the mixture was stirred at 25° C. for 4 hours. Sodium triacetoxyborohydride was added (639 mg, 3.01 mmol), and the reaction mixture was stirred at 25° C. for 12 hours. The reaction was heated to 80° C. for 2 hours, then was cooled to 25° C., and 3-(trifluoromethoxy)benzaldehyde (144 µl, 1.005 mmol) was added. The reaction mixture was stirred at 25° C. for 2 hours, and then was heated to 50° C. for 10 hours. The reaction mixture was quenched with saturated ammonium chloride solution and then was extracted into EtOAc. The organic phase was washed four times with water, then once with brine, then was dried with MgSO$_4$, filtered, concentrated, and purified on a 40 g silica gel column with a 0-100% DCM/Hexanes gradient. (R)-1,1,1-trifluoro-3-{2-phenyl-4-[3-(trifluoromethoxy)benzyl]-3,4-dihydroquinoxalin-1(2H)-yl}propan-2-ol was isolated as a 10:3 (R:S) mixture of diastereomers. This mixture was purified with reverse phase C18 chromatography with a 50-100% MeCN/H$_2$O gradient with 0.1% TFA modifier. Diastereomerically pure (R)-3-((R)-4-(3-trifluoromethoxy)-2-phenyl-3,4-dihydroquinoxalin-1(2H)-yl)-1,1,1-trifluoro-propan-2-ol was isolated. $^{1}$H NMR (400 MHz, CDCl$_3$) δ 3.28 (dd, J=9.2, 2.8 Hz, 1H), 3.39 (dd, J=12.4, 8.0 Hz, 1H), 3.63 (dd, J=8.8, 2.8 Hz, 1H), 3.83 (d, J=12.4 Hz, 1H), 4.24 (d, J=8.8 Hz, 1H), 4.37 (d, J=8.8 Hz, 1H), 4.42 (m, 1H), 4.87 (s, 1H), 6.56 (d, J=6.4 Hz, 1H), 6.70 (m, 2H), 6.82 (m, 2H), 6.93 (d, J=6 Hz, 1H), 7.04 (d, J=6.4 Hz, 2H), 7.22 (m, 3H), 7.33 (m, 3H), MS m/z=497.28.

Example 18

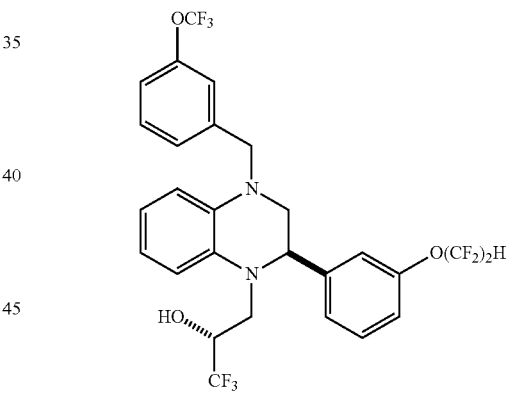

(R)-1,1,1-trifluoro-3-((R)-4-(3-trifluoromethoxy) benzyl)-2-(3-(1,1,2,2,-tetrafluoroethoxy)phenyl)-3,4-dihydroquinoxalin-1(2H)-yl)propan-2-ol SPA: 15 nM Example 18 was prepared from 2-bromo-1-(3-(1,1,2,2,-tetrafluoroethoxy)phenyl)ethanone in three steps, using the reactions detailed in Schemes A6, A2 and A1. Spectral data are as follows: $^{1}$H NMR (400 MHz, CDCl$_3$) δ 2.70 (bd, J=4.1 Hz, 1H), 3.24 (dd, J=11.3, 3.4 Hz, 1H), 3.34 (dd, J=15.5, 9.7 Hz, 1H), 3.58 (dd, J=11.3, 3.3 Hz, 1H), 3.86 (d, J=15.4 Hz, 1H), 4.20 (d, J=15.7 Hz, 1H), 4.40 (d, J=15.8 Hz, 1H), 4.46 (m, 1H), 4.927 (t, J=3.3 Hz, 1H), 5.90 (tt, J=53.1, 2.7 Hz, 1H), 6.59 (d, J=7.9 Hz, 1H), 6.72 (m, 2H), 6.84 (m, 2H), 6.92 (d, J=7.6 Hz, 1H), 7.20 (m, 1H), 7.35 (t, J=7.9 Hz, 1H), MS m/z=613.03.

Scheme A12

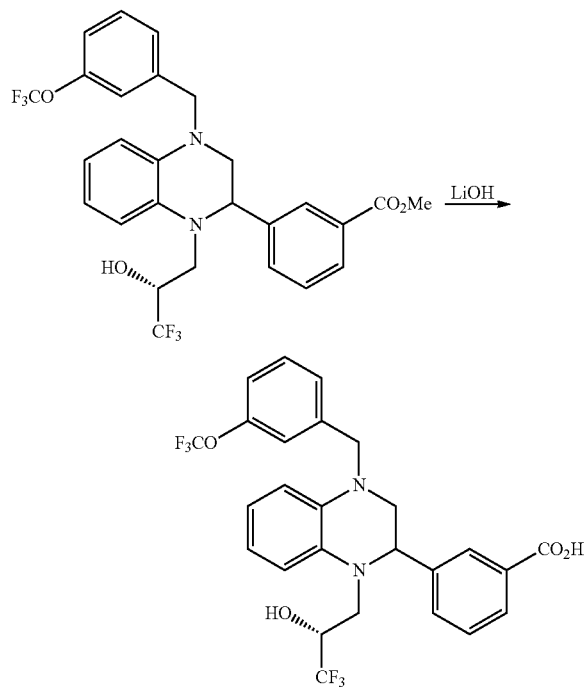

Methyl 3-{1-[(R)-3,3,3-trifluoro-2-hydroxypropyl]-4-[3-(trifluoromethoxy)benzyl]-1,2,3,4-tetrahydroquinoxalin-2-yl}benzoate (700 mg, 1.262 mmol) is made as described in Example 16 but with one stereochemical center unresolved. The compound was dissolved in MeOH (12.6 mL), lithium hydroxide monohydrate (530 mg, 12.62 mmol) was added, and the reaction mixture was heated to 60° C. for 4 hours. The crude mixture was dissolved in saturated ammonium chloride solution and extracted into EtOAc, the organic phase was dried with anhydrous magnesium sulfate, filtered, concentrated, and purified on a silica gel column with a 0-100% Hex/EtOAc gradient. The major peak was concentrated to afford 3-{1-[(R)-3,3,3-trifluoro-2-hydroxypropyl]-4-[3-(trifluoromethoxy)benzyl]-1,2,3,4-tetra-hydroquinoxalin-2-yl}benzoic acid. MS m/z=541.09.

Example 19

Scheme A13

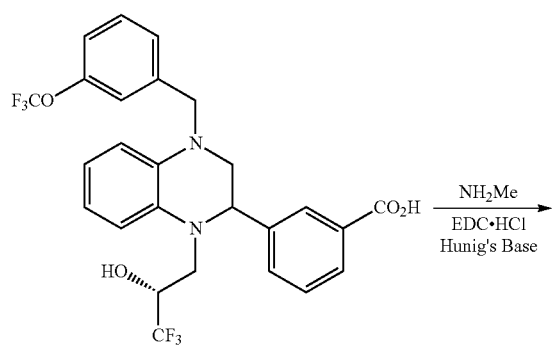

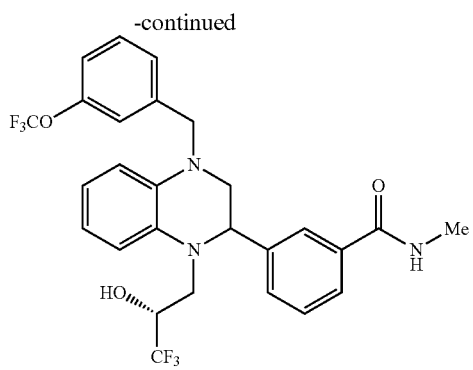

SPA: 90 nM

3-{1-[(R)-3,3,3-trifluoro-2-hydroxypropyl]-4-[3-(trifluoromethoxy)benzyl]-1,2,3,4-tetrahydroquinoxalin-2-yl}benzoic acid (100 mg, 0.185 mmol) (from Scheme A12) was dissolved in MeOH (925 µl), Hunig's Base (97 µl, 0.555 mmol), methylamine (93 µl, 0.185 mmol), and 3-(ethyliminomethyleneamino)-N,N-dimethyl-propan-1-amine (106 mg, 0.555 mmol) were added, and the mixture was stirred at 25° C. overnight. The product was purified on a reverse phase column, 10-90% MeCN/H₂O gradient, 0.1% TFA modifier, yielding Example 19, N-methyl-3-{1-[(R)-3,3,3-trifluoro-2-hydroxypropyl]-4-[3-(trifluoro-methoxy)benzyl]-1,2,3,4-tetrahydro quinoxalin-2-yl}benzamide. MS m/z=554.04.

Example 20

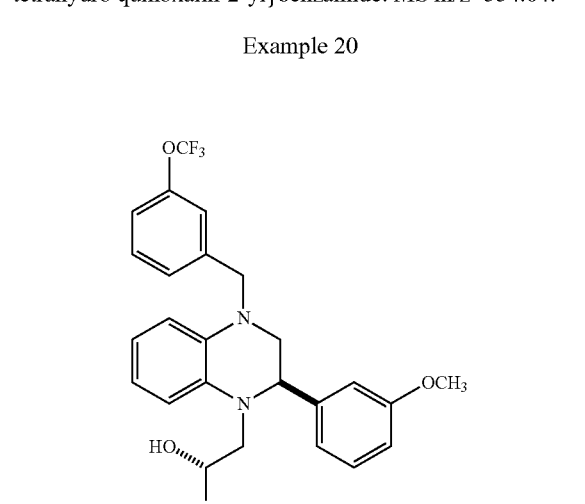

(R)-1,1,1-trifluoro-3-((R)-4-(3-trifluoromethoxy)benzyl)-2-(3-methoxyphenyl)-3,4-dihydroquinoxalin-1(2H)-yl)propan-2-ol SPA: 78 nM Example 20 was prepared from 2-bromo-1-(3-methoxyphenyl)ethanone using the reaction conditions detailed in scheme A11. Spectral data are as follows: ¹H NMR (400 MHz, CDCl₃) δ 2.65 (bs, 1H) 3.29 (dd, J=11.4, 3.8 Hz, 1H), 3.39 (dd, J=15.4, 9.6 Hz, 1H), 3.61 (dd, J=11.3, 3.2 Hz, 1H), 3.77 (s, 3H), 3.83 (d, J=15.7 Hz, 1H), 4.24 (d, J=15.8 Hz, 1H), 4.38 (d, J=15.8 Hz, 1H), 4.42 (m, 1H), 4.84 (t, J=3 Hz, 1H), 6.55 (d, J=7.9 Hz, 1H), 6.70 (m, 2H), 6.76 (s, 1H), 6.81 (m, 2H), 6.86 (m, 2H), 6.98 (d, J=7.5 Hz, 1H), 7.05 (d, J=8 Hz, 1H), 7.23 (t, J=7.9 Hz, 1H), 7.26 (t, J=7.98.1 Hz, 1H), MS m/z=526.14.

Example 21

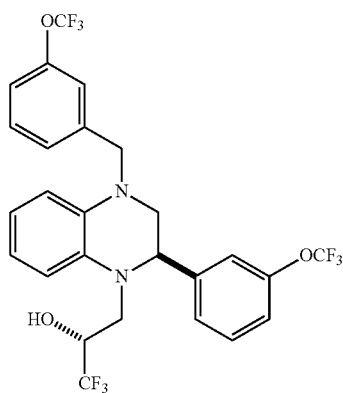 [SMILES: O[C@H](CN1c2ccccc2N(Cc2cccc(OC(F)(F)F)c2)C[C@H]1c1cccc(OC(F)(F)F)c1)C(F)(F)F]

(R)-1,1,1-trifluoro-3-((R)-4-(3-trifluoromethoxy)benzyl)-2-(3-trifluoromethoxyphenyl)-3,4-dihydroquinoxalin-1(2H)-yl)propan-2-ol SPA: 19 nM Example 21 was prepared from 2-bromo-1-(3-trifluoromethoxyphenyl)ethanone using reaction conditions detailed in Scheme A11. Spectral data are as follows: $^1$H NMR (400 MHz, CDCl$_3$) δ 2.57 (d, J=5.8 Hz, 1H) 3.24 (dd, J=11.5, 3.2 Hz, 1H), 3.34 (dd, J=15.6, 9.6 Hz, 1H), 3.60 (dd, J=11.4, 3.3 Hz, 1H), 3.87 (d, J=15.5 Hz, 1H), 4.20 (d, J=15.7 Hz, 1H), 4.42 (d, J=15.7 Hz, 1H), 4.48 (m, 1H), 4.95 (t, J=3.2 Hz, 1H), 6.61 (d, J=7.9 Hz, 1H), 6.72 (m, 2H), 6.83 (s, 1H), 6.85 (t, J=7.8 Hz, 1H), 6.92 (d, J=7.6 Hz, 1H), 7.08 (m, 2H), 7.16 (d, J=7.6 Hz, 1H), 7.21 (m, 3H), 7.37 (t, J=8.1 Hz, 1H), MS m/z=581.1.

Example 22

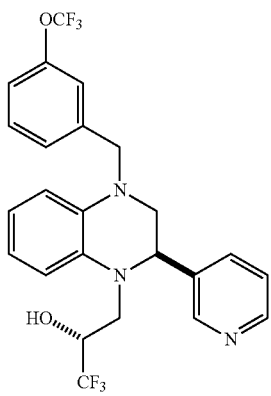

(R)-1,1,1-trifluoro-3-((R)-2-(pyridine-3-yl)-4-(3-trifluoromethoxy)benzyl)-3,4-dihydroquinoxalin-1(2H)-yl)propan-2-ol SPA: 258 nM Example 22 was prepared from 2-bromo-1-(pyridine-3-yl)ethanone using reaction conditions detailed in scheme A11. Spectral data are as follows: $^1$H NMR (400 MHz, CDCl$_3$) δ 3.20 (dd, J=11.4, 3.2 Hz, 1H), 3.31 (dd, J=15.6, 9.7 Hz, 1H), 3.62 (dd, J=11.6, 3.3 Hz, 1H), 3.86 (d, J=15.5 Hz, 1H), 4.22 (d, J=15.7 Hz, 1H), 4.41 (d, J=15.7 Hz, 1H), 4.48 (m, 1H), 4.94 (m, 1H), 6.62 (d, J=7.8 Hz, 1H), 6.70 (m, 2H), 6.84 (m, 2H), 6.91 (d, J=7.9 Hz, 1H), 7.05 (d, J=8.5 Hz, 1H), 7.22 (t, J=8.0 Hz, 1H), 7.26 (m, 1H), 7.52 (d, J=7.8 Hz, 1H), 8.47 (s, 1H), 8.56 (d, J=4.7 Hz, 1H), MS m/z=498.06

Example 23

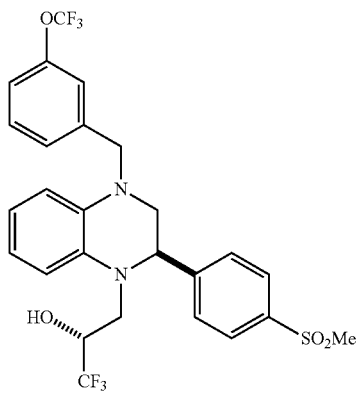 [SMILES: CS(=O)(=O)c1ccc([C@@H]2CN(Cc3cccc(OC(F)(F)F)c3)c3ccccc3N2C[C@@H](O)C(F)(F)F)cc1]

(R)-1,1,1-trifluoro-3-((R)-2-(4-methylsulfonyl)phenyl)-4-(3-trifluoromethoxy)benzyl)-3,4-dihydroquinoxalin-1(2H)-yl)propan-2-ol SPA: 96 nM Example 23 was prepared from 2-bromo-1-(4-methylsulfonyl)phenyl)ethanone using the reaction conditions from Scheme A11. Spectral data are as follows: $^1$H NMR (400 MHz, CDCl$_3$) δ 2.57 (bs, 1H) 3.08 (s, 3H) 3.25 (m, 2H), 3.62 (dd, J=11.6, 3.4 Hz, 1H), 3.89 (d, J=15.5 Hz, 1H), 4.21 (d, J=15.8 Hz, 1H), 4.39 (d, J=15.6 Hz, 1H), 4.51 (m, 1H), 5.02 (t, J=3.1 Hz, 1H), 6.62 (d, J=7.9 Hz, 1H), 6.70 (d, J=8 Hz, 1H), 6.73 (t, J=7.8, 1H), 6.86 (t, J=8.2 Hz, 1H), 6.89 (s, 1H), 7.06 (d, J=7.9 Hz, 1H), 7.21 (t, J=7.8 Hz, 1H), 7.41 (d, J=8.3 Hz, 1H), 7.90 (d, J=7.8 Hz, 1H), MS m/z=575.05.

Example 24

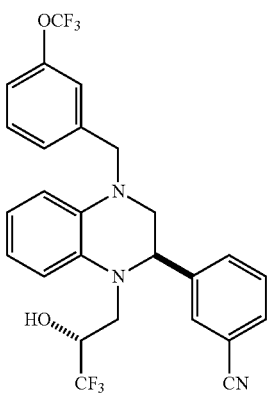

(R)-1,1,1-trifluoro-3-((R)-2-(3-cyanophenyl)4-(3-trifluoromethoxy)benzyl)-3,4-dihydroquinoxalin-1(2H)-yl)propan-2-ol SPA: 98 nM Example 24 was prepared from 2-bromo-1-(3-cyanophenyl)ethanone using the reaction conditions detailed in Scheme A11. Spectral data are as follows: $^1$H NMR (400 MHz, CDCl$_3$) δ 2.65 (bs, 1H) 3.18 (dd, J=11.4, 3.0 Hz, 1H), 3.27 (dd, J=15.5, 9.6 Hz, 1H), 3.56 (dd, J=11.3, 3.2 Hz, 1H), 3.90 (d, J=15.6 Hz, 1H) 4.15 (d, J=15.5 Hz, 1H), 4.43 (d, J=15.5 Hz, 1H), 4.53 (m, 1H), 4.99 (t, J=2.8 Hz, 1H), 6.63 (d, J=7.9 Hz, 1H), 6.70 (d, J=8.0 Hz, 1H), 6.74 (m, 2H), 6.86 (t, J=7.7 Hz, 1H), 6.91 (d, J=7.7 Hz, 1H), 7.06 (d, J=8.1 Hz, 1H), 7.22 (t, J=7.9 Hz, 1H), 7.44 (m, 2H), 7.49 (s, 1H), 7.61 (m, 1H), MS m/z=522.10.

Example 25

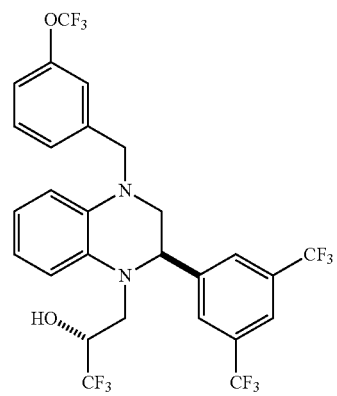 [SMILES: O[C@H](CN1c2ccccc2N(Cc2cccc(OC(F)(F)F)c2)C[C@H]1c1cc(C(F)(F)F)cc(C(F)(F)F)c1)C(F)(F)F]

(R)-1,1,1-trifluoro-3-((R)-2-(3,5-bis-trifluoromethylphenyl)-4-(3-trifluoromethoxy)benzyl)-3,4-dihydroquinoxalin-1(2H)-yl)propan-2-ol SPA: 770 nM Example 25 was prepared from 2-bromo-1-(3,5-bis-trifluoromethylphenyl) ethanone in three steps, using the reactions detailed in Scheme A6, A1 and A2. Spectral data are as follows: $^1$H NMR (400 MHz, CDCl$_3$) δ 3.14 (dd, J=11.5, 3 Hz, 1H), 3.24 (dd, J=11.5, 3.3 Hz, 1H), 3.93 (d, J=15.6 Hz, 1H), 4.09 (d, J=15.2 Hz, 1H), 4.47 (d, J=15.2 Hz, 1H), 4.56 (m, 1H), 5.12 (t, J=3 Hz, 1H), 6.68 (d, J=7.8 Hz, 1H), 6.71 (d, J=8 Hz, 1H), 6.76 (m, 2H), 6.89 (m, 2H), 7.04 (d, J=8.1 Hz, 1H), 7.18 (t, J=7.9 Hz, 1H), 7.64 (s, 2H), 7.84 (s, 1H) MS m/z=633.11.

Example 26

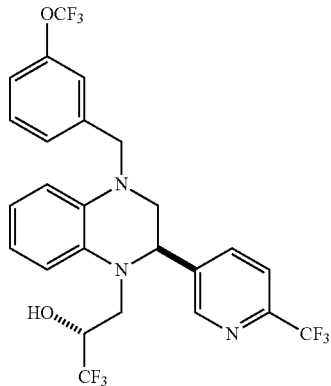 [SMILES: O[C@H](CN1c2ccccc2N(Cc2cccc(OC(F)(F)F)c2)C[C@H]1c1ccc(C(F)(F)F)nc1)C(F)(F)F]

(R)-1,1,1-trifluoro-3-((R)-4-(3-trifluoromethoxy)benzyl)-2-(6-trifluoromethyl)pyridin-3-yl)-3,4-dihydroquinoxalin-1(2H)-yl)propan-2-ol SPA: 24 nM Example 26 was prepared from [6-(trifluoromethyl)pyridin-3-yl]boronic acid in three steps, using reactions detailed in Scheme A3, A1 and A2. Spectral data are as follows: $^1$H NMR (400 MHz, CDCl$_3$) δ 3.19 (dd, J=9.1, 2.8 Hz, 1H), 3.26 (dd, J=15.5, 9.6 Hz, 1H), 3.62 (dd, J=11.7, 8.3 Hz, 1H) 3.90 (d, J=14.6 Hz, 1H), 4.18 (d, J=15.5 Hz, 1H), 4.44 (d, J=15.2 Hz, 1H), 4.52 (m, 1H), 5.05 (bs, 1H), 6.66 (d, J=8.0 Hz, 1H), 6.70 (d, J=8.1 Hz, 1H), 6.75 (t, J=7.4 Hz, 1H), 6.82 (s, 1H), 6.86 (m, 2H), 7.06 (d, J=8.1 Hz, 1H) 7.20 (t, J=7.8 Hz, 1H), 7.64 (d, J=8.1 Hz, 1H), 7.68 (d, J=8.0 Hz, 1H) 8.58 (s, 1H) MS m/z=566.11.

Example 27

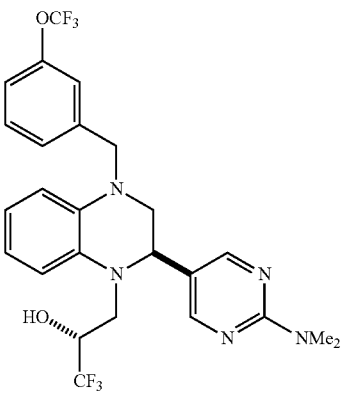 [SMILES: CN(C)c1ncc([C@@H]2CN(Cc3cccc(OC(F)(F)F)c3)c3ccccc3N2C[C@@H](O)C(F)(F)F)cn1]

(R)-3-((R)-2(2-dimethylamino)pyrimidin-5-yl)-4-(3-trifluoromethoxy)benzyl)-3,4-dihydroquinoxalin-1(2H)-yl)-1,1,1-trifluoropropan-2-ol SPA: 30 nM Example 27 was prepared from N,N-dimethyl-5-(4,4,5,5-tetramethyl-1,3,2-dioxaborolan-2-yl)pyrimidin-2-amine in three steps, using reactions detailed in Scheme A3, A1 and A2. Spectral data are as follows: $^1$H NMR (400 MHz, CDCl$_3$) 82.72 (d, J=4.6 Hz, 1H) 3.12 (dd, J=11.3, 7.8 Hz, 1H) 3.20 (s, 6H), 3.32 (dd, J=15.6, 6.0 Hz, 1H), 3.58 (dd, J=11.3, 8.2 Hz, 1H) 3.75 (d, J=15.6 Hz, 1H), 4.32 (d, J=15.8 Hz, 1H), 4.43 (m, 3H), 4.65 (t, J=3.3 Hz, 1H), 6.63 (t, J=8.8 Hz, 2H), 6.70 (t, J=7.4 Hz, 1H), 6.79 (t, J=7.9 Hz, 1H), 6.95 (s, 1H), 7.09 (d, J=7.9 Hz, 1H), 7.29 (t, J=4.4 Hz, 2H) 8.16 (s, 1H), MS m/z=542.3.

Scheme A14

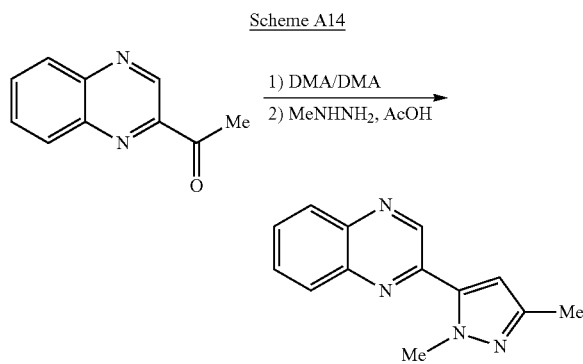

1-(quinoxalin-2-yl)ethanone (1.13 g, 6.56 mmol) and N,N-dimethylacetamide dimethylacetal (1.173 ml, 7.22 mmol) were combined and heated to 100° C. for 3 h. The mixture was cooled to r.t. $^1$H NMR indicated that the material was sufficiently pure to carry onto the next step without further purification (1.49 g, 94% yield). 3-(dimethylamino)-1-(quinoxalin-2-yl)but-2-en-1-one (791 mg, 3.28 mmol) and methylhydrazine (0.174 ml, 3.28 mmol) were combined in acetic acid (6 ml) and stirred at 55° C. until the reaction was judged to be complete by LCMS. The acetic acid was removed and the material was taken up in DCM and washed with saturated NaHCO$_3$ solution. The organic extracts were dried over Na$_2$SO$_4$, filtered, and concentrated. $^1$H NMR (500 MHz, CDCl$_3$) δ 9.14 (1H, s), 8.13-8.11 (2H, m), 7.83-7.77 (2H, m), 6.72 (1H, s), 4.37 (3H, s), 2.39 (3H, s). MS m/z=225.3.

Scheme A15

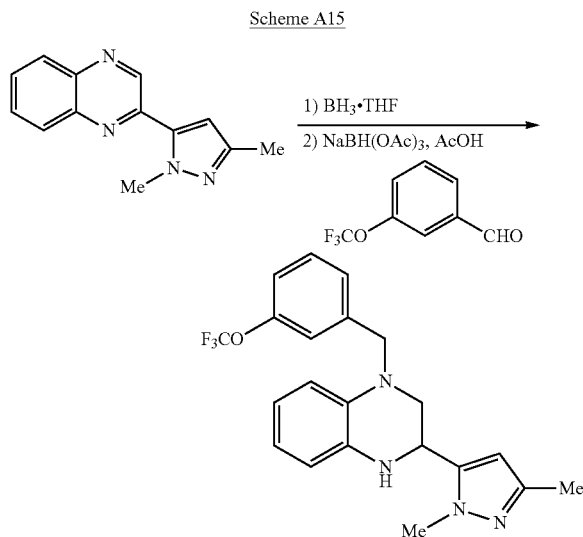

Borane-tetrahydrofuran complex (7.92 ml, 7.92 mmol) is added to a stirring solution of 2-(1,3-dimethyl-1H-pyrazol-5-yl)quinoxaline (740 mg, 3.30 mmol) in THF (10 ml) cooled to 0° C. The reaction is stirred at 0° C. until judged to be complete by LCMS (~1 h). The reaction is then quenched with saturated NH$_4$Cl solution and stirred until the bubbling ceases. The layers are separated, and the aqueous layer is extracted with ethyl acetate (2 times more). The combined extracts are dried over Na$_2$SO$_4$, filtered, and concentrated. The crude quinoxaline is used in the next step (0.760 g, 101% yield). Sodium triacetoxyborohydride (1412 mg, 6.66 mmol) is added to a stirring solution of crude 2-(1,3-dimethyl-1H-pyrazol-5-yl)-1,2,3,4-tetrahydroquinoxaline (760 mg, 3.33 mmol), 3-trifluoromethoxybenzaldehyde (0.524 ml, 3.66 mmol) and acetic acid (0.572 ml, 9.99 mmol) in methylene chloride (15 ml). The reaction is quenched with saturated NaHCO$_3$ solution and the mixture is stirred until the bubbling ceases. The layers are separated and the aqueous layer is extracted with methylene chloride (1×). The combined extracts are dried over Na$_2$SO$_4$, filtered, and concentrated. Purification by reverse phase chromatography (Biotage C-18 30 g SNAP cartridge; 5-60% acetonitrile in water+0.05% TFA). $^1$H NMR (500 MHz, CDCl$_3$) 87.37 (1H, t, J=3.2 Hz), 7.21 (1H, d, J=3.2 Hz), 7.17 (1H, s), 7.14 (1H, d, J=3.2 Hz), 6.74-6.69 (2H, m), 6.65-6.61 (2H, m), 6.04 (1H, s), 4.68 (1H, m), 4.49 (2H, m), 3.81 (3H, s), 3.42-3.40 (2H, m), 2.25 (3H, s). MS m/z=403.3.

Example 28

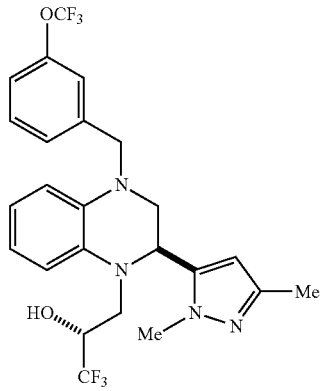 [SMILES: Cc1cc([C@@H]2CN(Cc3cccc(OC(F)(F)F)c3)c3ccccc3N2C[C@@H](O)C(F)(F)F)n(C)n1]

(R)-3-((R)-2(1,3-dimethyl-1H-pyrazol-5-yl)-4-(3-trifluoromethoxy)benzyl)-3,4-dihydroquinoxalin-1(2H)-yl)-1,1,1-trifluoropropan-2-ol SPA: 390 nM Example 28 was prepared from 3-(1,3-dimethyl-1H-pyrazol-5-yl)-1-[3-(trifluoromethoxy)benzyl]-1,2,3,4-tetrahydroquinoxaline in one step according to scheme A2. The compound was isolated as a mixture of diastereomers. Spectral data are as follows: $^1$H NMR (500 MHz, CDCl$_3$) δ 7.33-7.29 (1H, m), 7.11, 6.96 (3H, m), 6.74-6.69 (1.5H, m), 6.62-6.57 (1.5H, m), 6.52-6.47 (1H, m), 5.79 (0.5H, s), 5.70 (0.5H, s), 5.05 (0.5H, m), 4.77 (0.5H, m), 4.48 (0.5H, m), 4.45 (0.5H, m), 4.34-4.19 (2H, m), 3.79-3.72 (1H, m), 3.69 (1.5H, s), 3.67 (1.5H, s), 3.65-3.57 (1H, m), 3.55-3.42 (1H, m), 3.37-3.34 (0.5H, m), 3.20-3.15 (0.5H, m), 2.16 (1.5H, s), 2.14 (1.5H, s). MS m/z=515.3.

Table of Additional Examples

Examples 29-57 in Table 1 were synthesized by the methods summarized below, and by methods provided earlier in this document. The structures of Examples 29-57 are listed in the following Table. All of the entries in the Table were evaluated using the SPA assay. The assay results are provided in the table.

Examples 29-31 were prepared from (R)-2-phenyl-1,2,3,4-tetrahydroquinoxaline, which was obtained using the chiral separation procedure summarized in Scheme A14 below.

Scheme A14

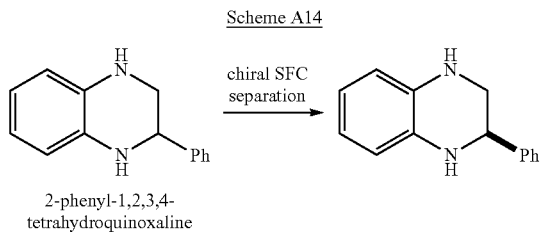 [SMILES: c1ccc(C2CNc3ccccc3N2)cc1 ; c1ccc([C@@H]2CNc3ccccc3N2)cc1]

2-phenyl-1,2,3,4-tetrahydroquinoxaline

Racemic 2-phenyl 1,2,3,4-tetrahydroquinoxaline was separated into its enantiomers in Scheme A14 by 4.6×250 mm ChiralCel OJ at 2.1 mL/min flow rate and 100 bar pressure with 15% methanol (0.2% DEA) in $CO_2$ at 35° C. to give (R)-2-phenyl 1,2,3,4-tetrahydroquinoxaline as the slower eluting enantiomer. $^1$H NMR (400 MHz, $CDCl_3$) 83.36 (t, J=6.4 Hz, 1H), 3.51 (t, J=8.8 Hz, 1H), 3.84 (bs, 1H), 3.94 (bs, 1H), 4.52 (dd, J=6.4, 2.4 Hz, 1H), 6.62 (m, 2H), 6.68 (m, 2H), 7.39 (m, 5H).

(R)-2-phenyl-1,2,3,4-tetrahydroquinoxaline was then used to make Examples 29-31 using the procedures outlined in Schemes A1 and A2.

Examples 32-48 were prepared from racemic 2-(3-trifluoromethylphenyl)-1,2,3,4-tetrahydroquinoxaline using procedures outlined in Schemes A1 and A2. Examples 49-55 were prepared according to the procedure outlined in scheme A11.

TABLE 1

| Example | Compound | Structure | $IC_{50}$ | LCMS |
|---|---|---|---|---|
| 29 | (R)-3-((R)-4-(3-fluoro-5-(trifluoromethyl)benzyl)-2-phenyl-3,4-dihydroquinoxalin-1(2H)-yl)-1,1,1-trifluoropropan-2-ol | 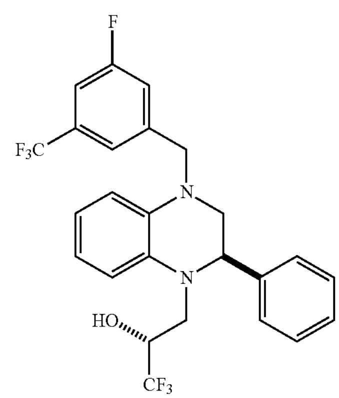 [SMILES: O[C@H](CN1c2ccccc2N(Cc2cc(F)cc(C(F)(F)F)c2)C[C@H]1c1ccccc1)C(F)(F)F] | 105 nM | 499.1 |
| 30 | (R)-3-((R)-4-(3-chlorobenzyl)-2-phenyl-3,4-dihydroquinoxalin-1(2H)-yl)-1,1,1-trifluoropropan-2-ol | 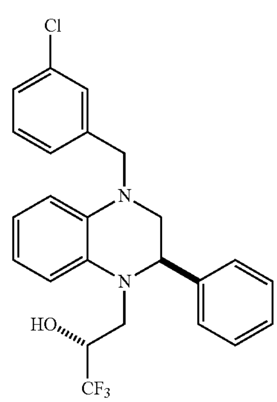 [SMILES: O[C@H](CN1c2ccccc2N(Cc2cccc(Cl)c2)C[C@H]1c1ccccc1)C(F)(F)F] | 1396 | 447.1 |

TABLE 1-continued

| Example | Compound | Structure | IC$_{50}$ | LCMS |
|---------|----------|-----------|-----------|------|
| 31 | (R)-3-((R)-4-(3,5-dichlorobenzyl)-2-phenyl-3,4-dihydroquinoxalin-1(2H)-yl)-1,1,1-trifluoropropan-2-ol | 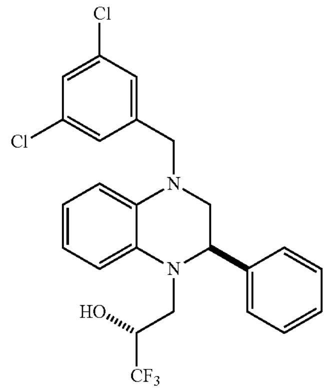 [SMILES: O[C@H](CN1c2ccccc2N(Cc2cc(Cl)cc(Cl)c2)C[C@H]1c1ccccc1)C(F)(F)F] | 2760 | 482.2 |
| 32 | (R)-3-((R)-4-(3,5-dichlorobenzyl)-2-(3-(trifluoromethyl)phenyl)-3,4-dihydroquinoxalin-1(2H)-yl)-1,1,1-trifluoro propan-2-ol | 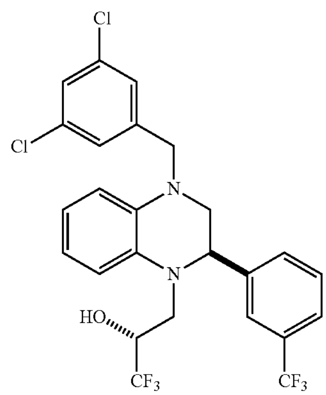 [SMILES: O[C@H](CN1c2ccccc2N(Cc2cc(Cl)cc(Cl)c2)C[C@H]1c1cccc(C(F)(F)F)c1)C(F)(F)F] | 12 | 482.2 |
| 33 | (R)-3-((R)-4-(2-methylbenzyl)-2-(3-(trifluoromethyl)phenyl)-3,4-dihydroquinoxalin-1(2H)-yl)-1,1,1-trifluoro propan-2-ol | 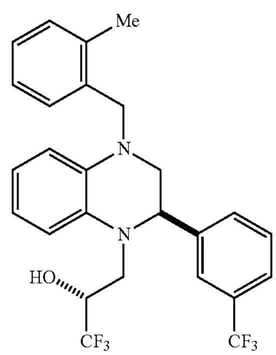 [SMILES: Cc1ccccc1CN1C[C@@H](c2cccc(C(F)(F)F)c2)N(C[C@@H](O)C(F)(F)F)c2ccccc21] | 428 | 495.1 |
| 34 | (R)-3-((R)-4-(2,3-dichlorobenzyl)-2-(3-(trifluoromethyl)phenyl)-3,4-dihydroquinoxalin-1(2H)-yl)-1,1,1-trifluoro propan-2-ol | 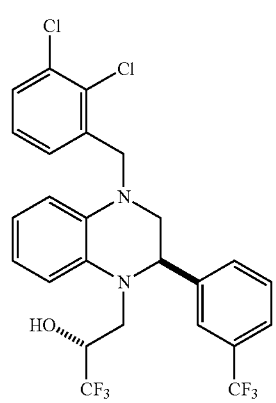 [SMILES: O[C@H](CN1c2ccccc2N(Cc2cccc(Cl)c2Cl)C[C@H]1c1cccc(C(F)(F)F)c1)C(F)(F)F] | 169 | 482.2 |

TABLE 1-continued

| Example | Compound | Structure | IC$_{50}$ | LCMS |
|---|---|---|---|---|
| 35 | (R)-3-((R)-4-(2,6-dichlorobenzyl)-2-(3-(trifluoromethyl)phenyl)-3,4-dihydroquinoxalin-1(2H)-yl)-1,1,1-trifluoropropan-2-ol | 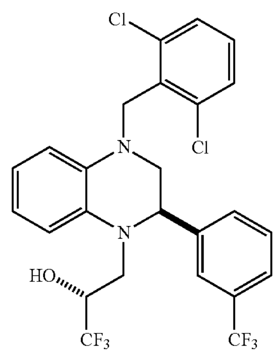 [SMILES: O[C@H](CN1c2ccccc2N(Cc2c(Cl)cccc2Cl)C[C@H]1c1cccc(C(F)(F)F)c1)C(F)(F)F] | 1161 | 482.2 |
| 36 | (R)-3-((R)-4-(3-chloro-6-methylpyridin-4-yl)-2-(3-(trifluoromethyl)phenyl)-3,4-dihydroquinoxalin-1(2H)-yl)-1,1,1-trifluoropropan-2-ol | 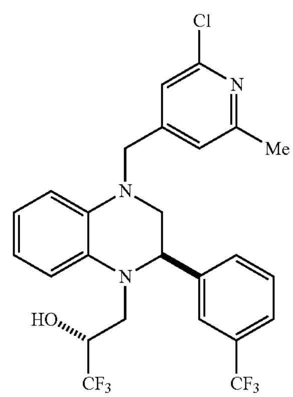 [SMILES: Cc1cc(CN2C[C@@H](c3cccc(C(F)(F)F)c3)N(C[C@@H](O)C(F)(F)F)c3ccccc32)cc(Cl)n1] | 67 | 530.1 |
| 37 | (R)-3-((R)-4-(cyclohexylmethyl)-2-(3-(trifluoromethyl)phenyl)-3,4-dihydroquinoxalin-1(2H)-yl)-1,1,1-trifluoropropan-2-ol | 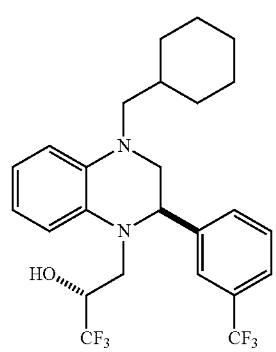 [SMILES: O[C@H](CN1c2ccccc2N(CC2CCCCC2)C[C@H]1c1cccc(C(F)(F)F)c1)C(F)(F)F] | 1270 | 487.1 |
| 38 | (R)-3-((R)-4-(thiophenyl-3-ylmethyl)-2-(3-(trifluoromethyl)phenyl)3,4-dihydroquinoxalin-1(2H)-yl)-1,1,1-trifluoropropan-2-ol | 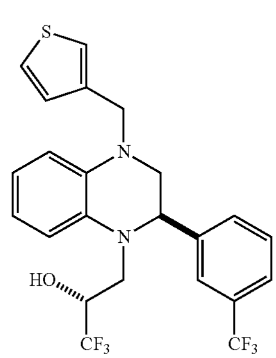 [SMILES: O[C@H](CN1c2ccccc2N(Cc2ccsc2)C[C@H]1c1cccc(C(F)(F)F)c1)C(F)(F)F] | 461 | 487.1 |

TABLE 1-continued

| Example | Compound | Structure | IC$_{50}$ | LCMS |
|---------|----------|-----------|-----------|------|
| 39 | (2R)-3-(4-(4-chlorobenzyl)-2-(3-(trifluoromethyl)phenyl)-3,4-dihydroquinoxalin-1(2H)-yl)-1,1,1-trifluoropropan-2-ol | 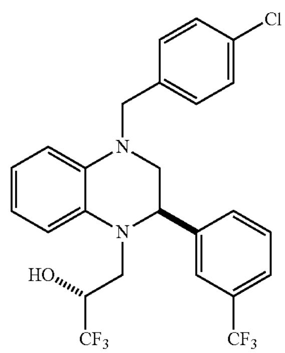 [SMILES: O[C@H](CN1c2ccccc2N(Cc2ccc(Cl)cc2)C[C@H]1c1cccc(C(F)(F)F)c1)C(F)(F)F] | 548.4 | 447.1 |
| 40 | (2R)-1,1,1-trifluoro-3-(4-(3-(trifluoromethyl)benzyl)-2-(3-(trifluoromethyl)phenyl)-3,4-dihydroquinoxalin-1(2H)-yl)propan-2-ol | 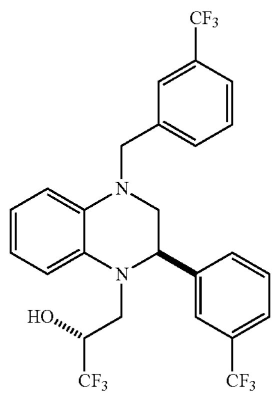 [SMILES: O[C@H](CN1c2ccccc2N(Cc2cccc(C(F)(F)F)c2)C[C@H]1c1cccc(C(F)(F)F)c1)C(F)(F)F] | 57.1 | 549.1 |
| 41 | (2R)-1,1,1-trifluoro-3-(4-(3-fluoro-5-(trifluoromethyl)benzyl)-2-(3-(trifluoromethyl)phenyl)-3,4-dihydroquinoxalin-1(2H)-yl)propan-2-ol | 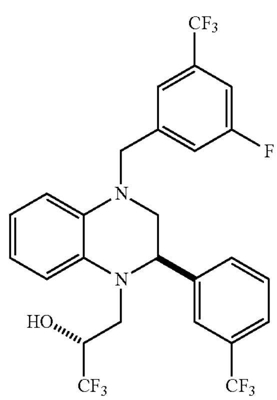 [SMILES: O[C@H](CN1c2ccccc2N(Cc2cc(F)cc(C(F)(F)F)c2)C[C@H]1c1cccc(C(F)(F)F)c1)C(F)(F)F] | 45.2 | 567.1 |
| 42 | (2R)-3-(4-(4-chloro-3-ethylbenzyl)-2-(3-(trifluoromethyl)phenyl)-3,4-dihydroquinoxalin-1(2H)-yl)-1,1,1-trifluoropropan-2-ol | 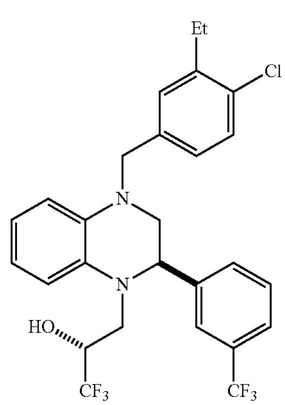 [SMILES: CCc1cc(CN2C[C@@H](c3cccc(C(F)(F)F)c3)N(C[C@@H](O)C(F)(F)F)c3ccccc32)ccc1Cl] | 45.1 | 542.1 |

TABLE 1-continued

| Example | Compound | Structure | IC$_{50}$ | LCMS |
|---|---|---|---|---|
| 43 | (2R)-1,1,1-trifluoro-3-(4-(2-methyl-5-(trifluoromethyl)benzyl)-2-(3-(trifluoromethyl)phenyl)-3,4-dihydroquinoxalin-1(2H)-yl)propan-2-ol | 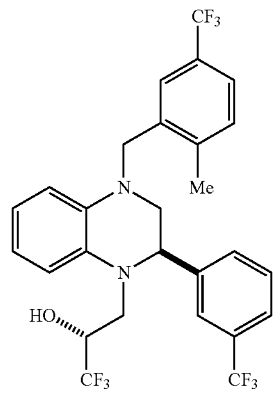 [SMILES: Cc1ccc(C(F)(F)F)cc1CN1C[C@@H](c2cccc(C(F)(F)F)c2)N(C[C@@H](O)C(F)(F)F)c2ccccc21] | 270 | 563.1 |
| 44 | (R)-3-((R)-4-(3-methylpyridin-2-yl)-2-(3-(trifluoromethyl)phenyl)-3,4-dihydroquinoxalin-1(2H)-yl)-1,1,1-trifluoro propan-2-ol | 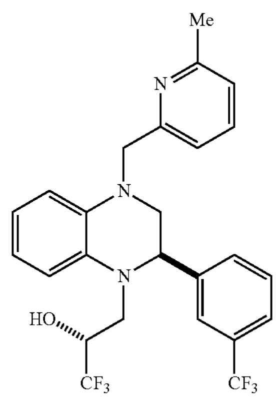 [SMILES: Cc1cccc(CN2C[C@@H](c3cccc(C(F)(F)F)c3)N(C[C@@H](O)C(F)(F)F)c3ccccc32)n1] | 460 | 496.1 |
| 45 | (R)-3-((R)-4-(6-isopropoxypyridin-2-yl)-2-(3-(trifluoromethyl)phenyl)-3,4-dihydroquinoxalin-1(2H)-yl)-1,1,1-trifluoro propan-2-ol | 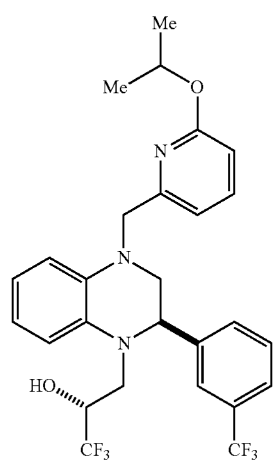 [SMILES: CC(C)Oc1cccc(CN2C[C@@H](c3cccc(C(F)(F)F)c3)N(C[C@@H](O)C(F)(F)F)c3ccccc32)n1] | 750 | 540.1 |
| 46 | (R)-3-((R)-4-(3-methoxypyridin-2-yl)-2-(3-(trifluoromethyl)phenyl)-3,4-dihydroquinoxalin-1(2H)-yl)-1,1,1-trifluoro propan-2-ol | 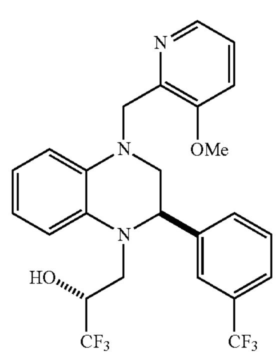 [SMILES: COc1cccnc1CN1C[C@@H](c2cccc(C(F)(F)F)c2)N(C[C@@H](O)C(F)(F)F)c2ccccc21] | 210 | 512.1 |

TABLE 1-continued

| Example | Compound | Structure | IC$_{50}$ | LCMS |
|---|---|---|---|---|
| 47 | (R)-3-((R)-4-(6-methoxypyridin-2-yl)-2-(3-(trifluoromethyl)phenyl)-3,4-dihydroquinoxalin-1(2H)-yl)-1,1,1-trifluoro propan-2-ol | 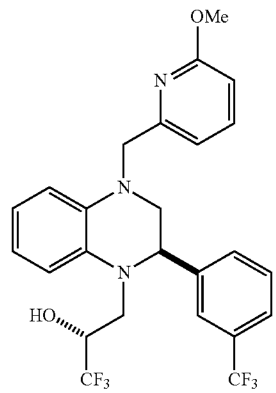 [SMILES: COc1cccc(CN2C[C@@H](c3cccc(C(F)(F)F)c3)N(C[C@@H](O)C(F)(F)F)c3ccccc32)n1] | 630 | 512.1 |
| 48 | (R)-3-((R)-4-(6-ethoxypyridin-2-yl)-2-(3-(trifluoromethyl)phenyl)-3,4-dihydroquinoxalin-1(2H)-yl)-1,1,1-trifluoro propan-2-ol | 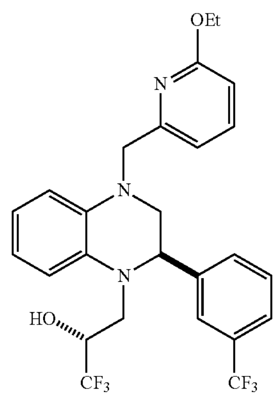 [SMILES: CCOc1cccc(CN2C[C@@H](c3cccc(C(F)(F)F)c3)N(C[C@@H](O)C(F)(F)F)c3ccccc32)n1] | 310 | 526.1 |
| 49 | (R)-1,1,1-trifluoro-3-((R)-4-(3-trifluoromethoxy)benzyl)-2-(4-chlorophenyl)-3,4-dihydroquinoxalin-1(2H)-yl)propan-2-ol | 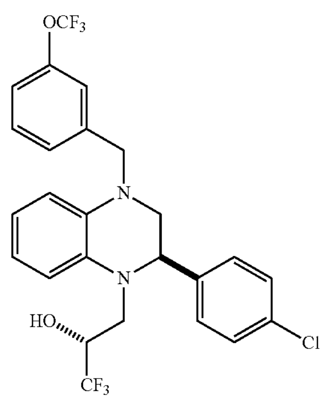 [SMILES: O[C@H](CN1c2ccccc2N(Cc2cccc(OC(F)(F)F)c2)C[C@H]1c1ccc(Cl)cc1)C(F)(F)F] | 20 | 515.1 |
| 50 | (R)-3-((R)-2-(6,7-dimethoxynaphthalen-2-yl)-4-(3-trifluoromethoxy)benzyl)-3,4-dihydroquinoxalin-1(2H)-yl)-1,1,1-trifluoropropan-2-ol | 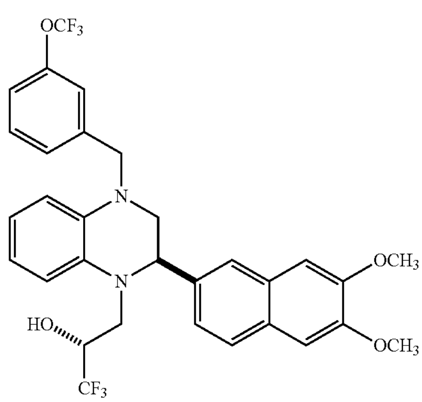 [SMILES: COc1cc2ccc([C@@H]3CN(Cc4cccc(OC(F)(F)F)c4)c4ccccc4N3C[C@@H](O)C(F)(F)F)cc2cc1OC] | 193 | 607.1 |

TABLE 1-continued

| Example | Compound | Structure | IC$_{50}$ | LCMS |
|---------|----------|-----------|-----------|------|
| 51 | (R)-3-((R)-2-(2,3-dihydrobenzo[b][1,4]dioxin-6-yl)-4-(3-trifluoromethoxy)benzyl)-3,4-dihydroquinoxalin-1(2H)-yl)-1,1,1-trifluoropropan-2-ol | 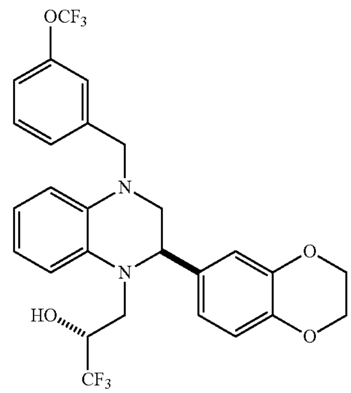 [SMILES: O[C@H](CN1c2ccccc2N(Cc2cccc(OC(F)(F)F)c2)C[C@H]1c1ccc2c(c1)OCCO2)C(F)(F)F] | 209 | 555.2 |
| 52 | (R)-1,1,1-trifluoro-3-((R)-4-(3-trifluoromethoxy)benzyl)-2-(4-fluorophenyl)-3,4-dihydroquinoxalin-1(2H)-yl)propan-2-ol | 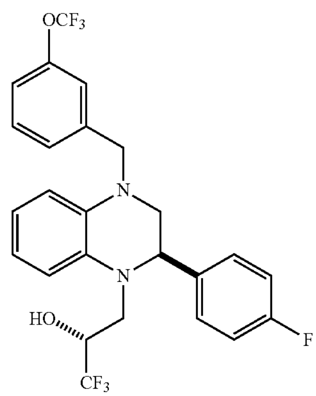 [SMILES: O[C@H](CN1c2ccccc2N(Cc2cccc(OC(F)(F)F)c2)C[C@H]1c1ccc(F)cc1)C(F)(F)F] | 682 | 515.1 |
| 53 | (R)-1,1,1-trifluoro-3-((R)-4-(3-trifluoromethoxy)benzyl)-2-(4-methylphenyl)-3,4-dihydroquinoxalin-1(2H)-yl)propan-2-ol | 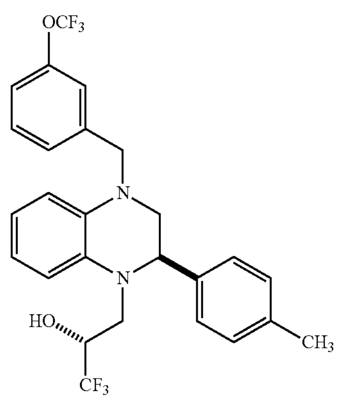 [SMILES: Cc1ccc([C@@H]2CN(Cc3cccc(OC(F)(F)F)c3)c3ccccc3N2C[C@@H](O)C(F)(F)F)cc1] | 56 | 511.1 |
| 54 | (R)-1,1,1-trifluoro-3-((R)-4-(3-trifluoromethoxy)benzyl)-2-(4-methoxyphenyl)-3,4-dihydroquinoxalin-1(2H)-yl)propan-2-ol | 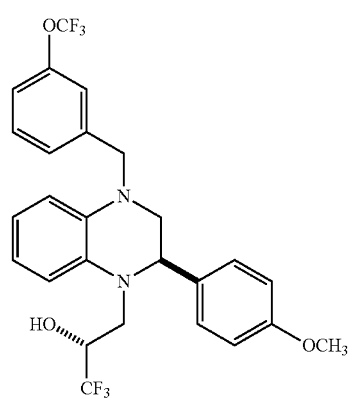 [SMILES: COc1ccc([C@@H]2CN(Cc3cccc(OC(F)(F)F)c3)c3ccccc3N2C[C@@H](O)C(F)(F)F)cc1] | 69 | 527.1 |

TABLE 1-continued

| Example | Compound | Structure | IC$_{50}$ | LCMS |
|---|---|---|---|---|
| 55 | (R)-1,1,1-trifluoro-3-((R)-2-(naphthalen-1-yl)-4-(trifluoromethoxyphenyl)-3,4-dihydroquinoxalin-1(2H)-yl)propan-2-ol | 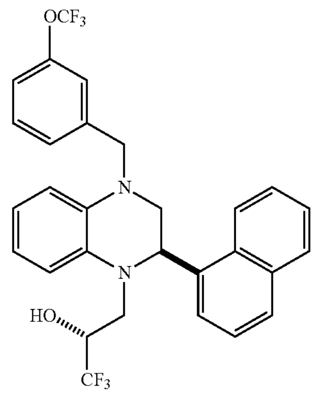 [SMILES: O[C@H](CN1c2ccccc2N(Cc2cccc(OC(F)(F)F)c2)C[C@H]1c1cccc2ccccc12)C(F)(F)F] | 1426 | 547.1 |
| 56 | (2R)-3(4-(1H-inden-1-yl))-2-(3-(1,1,2,2,-tetrafluoroethoxy)phenyl)-3,4-dihydroquinoxalin-1(2H)-yl-1,1,1-trifluoropropan-2-ol | 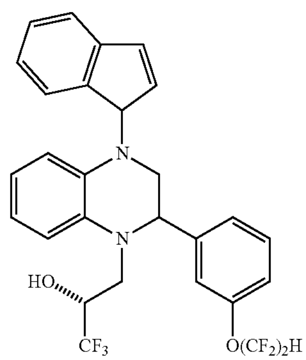 | 11 (Mix of diastereomers) | 439.26 |
| 57 | (2R)-1,1,1-trifluoro-3(4-(1,2,3,4-tetrahydronaphthalen-1-yl)-2-(3-trifluoromethyl)phenyl)-3,4-dihydroquinoxalin-1(2H)-yl-propan-2-ol | 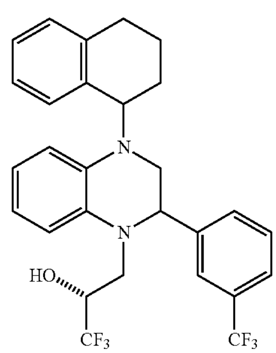 [SMILES: O[C@H](CN1c2ccccc2N(C2CCCc3ccccc32)CC1c1cccc(C(F)(F)F)c1)C(F)(F)F] | 12 (Mix of diastereomers) | 391.29 |

Additional examples were made using the methods, schemes, and intermediates described above. The structures are all shown in Table 2, along with 1050 assay data obtained using either the SPA method or the RTA method previously described carried out in 95% human serum.

TABLE 2

| Example | Structure | IC50 | Synthetic schemes |
| --- | --- | --- | --- |
| 58 | 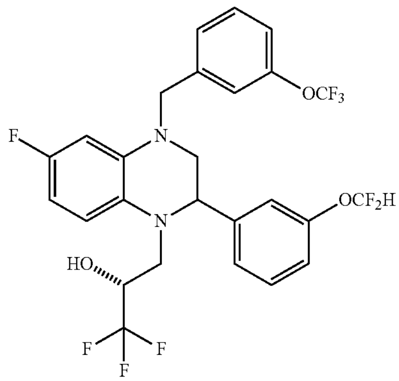 | RTA: 16 nM | A1, A2, A4 |
| 59 | 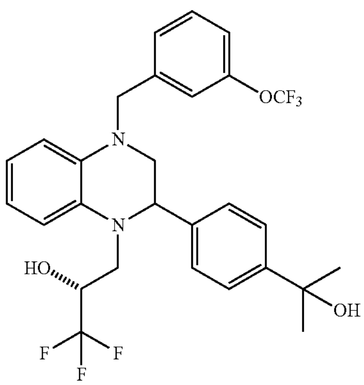 [SMILES: CC(C)(O)c1ccc(C2CN(Cc3cccc(OC(F)(F)F)c3)c3ccccc3N2C[C@@H](O)C(F)(F)F)cc1] | RTA: 24 nM | A1, A2, A4 |
| 60 | 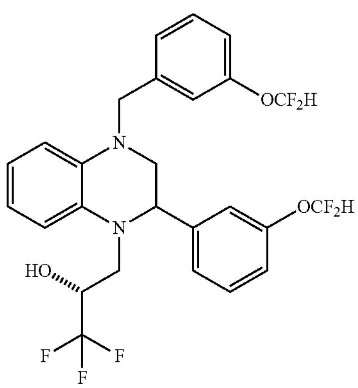 | RTA: 14 nM | A1, A2, A4 |
| 61 | 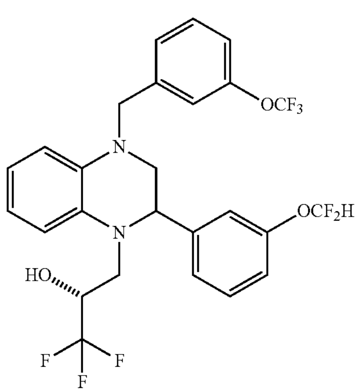 | RTA: 7.5 nM | A1, A2, A4 |

TABLE 2-continued
| Example | Structure | IC50 | Synthetic schemes |
|---|---|---|---|
| 62 | 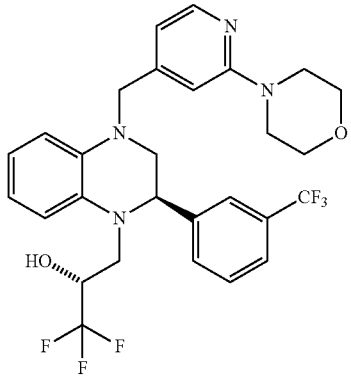 [SMILES: O[C@H](CN1c2ccccc2N(Cc2ccnc(N3CCOCC3)c2)C[C@H]1c1cccc(C(F)(F)F)c1)C(F)(F)F] | SPA: 326 nM | A1, A2, A4 |
| 63 | 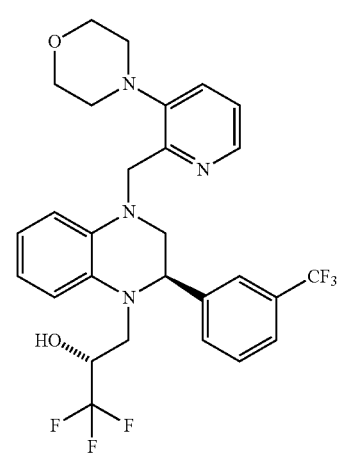 [SMILES: O[C@H](CN1c2ccccc2N(Cc2ncccc2N2CCOCC2)C[C@H]1c1cccc(C(F)(F)F)c1)C(F)(F)F] | SPA: 1569 nM | A1, A2, A4 |
| 64 | 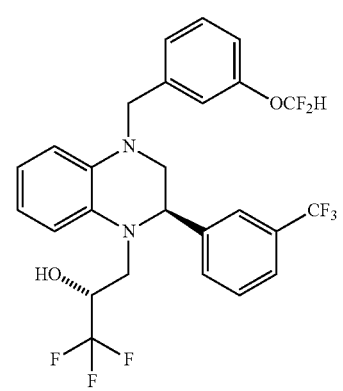 | SPA: 16 nM | A1, A2, A4 |
| 65 | 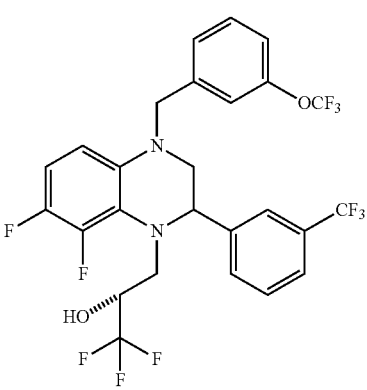 [SMILES: O[C@H](CN1c2c(ccc(F)c2F)N(Cc2cccc(OC(F)(F)F)c2)CC1c1cccc(C(F)(F)F)c1)C(F)(F)F] | SPA: 157 nM | A1, A2, A4 |

TABLE 2-continued
| Example | Structure | IC50 | Synthetic schemes |
|---|---|---|---|
| 66 | 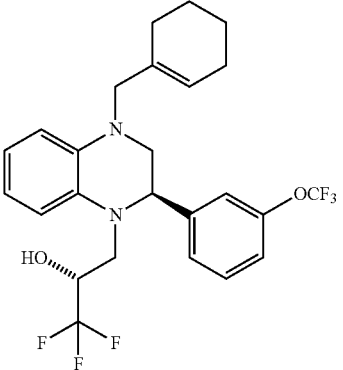 [SMILES: O[C@H](CN1c2ccccc2N(CC2=CCCCC2)C[C@H]1c1cccc(OC(F)(F)F)c1)C(F)(F)F] | SPA: 8 nM | A11 |
| 67 | 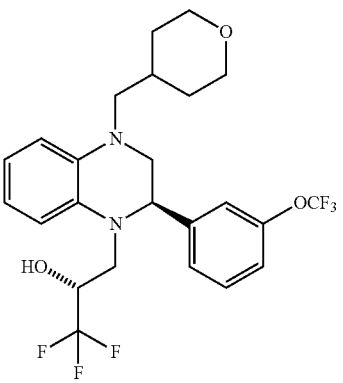 [SMILES: O[C@H](CN1c2ccccc2N(CC2CCOCC2)C[C@H]1c1cccc(OC(F)(F)F)c1)C(F)(F)F] | SPA: 29 nM | A11 |
| 68 | 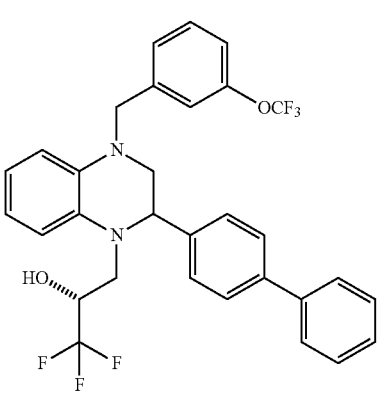 [SMILES: O[C@H](CN1c2ccccc2N(Cc2cccc(OC(F)(F)F)c2)CC1c1ccc(-c2ccccc2)cc1)C(F)(F)F] | SPA: 25 nM | A1, A2, A4 |
| 69 | 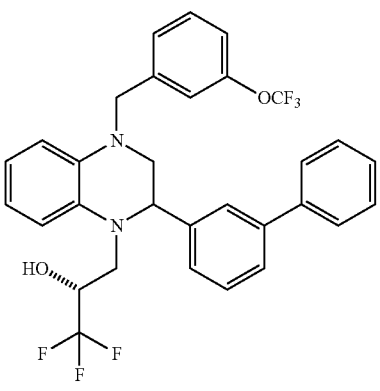 [SMILES: O[C@H](CN1c2ccccc2N(Cc2cccc(OC(F)(F)F)c2)CC1c1cccc(-c2ccccc2)c1)C(F)(F)F] | SPA: 163 nM | A1, A2, A4 |

The preceding examples are illustrative of the invention and are not to be construed as limiting the invention in any way. The claims appended hereto define the invention.

What is claimed is:

1. A compound of formula Ia, or a pharmaceutically acceptable salt thereof:

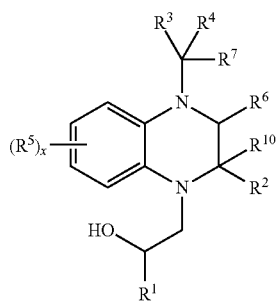

wherein $R^1$ is $CF_3$ or $CH_3$;

$R^2$ is phenyl; naphthyl; a 5-6 membered heteroaromatic ring having 1-2 heteroatoms independently selected from N and —($NR^8$)—, or phenyl to which is fused a 5-6-membered heterocyclic ring having 1-2 heteroatoms independently selected from O, S, and —($NR^8$)—, wherein $R^2$ is optionally substituted with 1-2 substituent groups independently selected from $C_1$-$C_3$alkyl, —$OC_1$-$C_3$alkyl, —$NR^8R^9$, —C(=O)$NR^8R^9$, —C(=O)$OC_1$-$C_3$alkyl, —S(O)$_2C_1$-$C_3$ alkyl, Cl, F, —CN, and phenyl, wherein phenyl is optionally substituted with 1-3 substituents independently selected from $CF_3$, $CH_3$, —$OCF_3$, —$OCH_3$, and halogen, wherein $C_1$-$C_3$ alkyl in all instances is optionally substituted with one —OH and optionally 1-5 F;

$R^6$ and $R^5$ are each independently H, $CF_3$, $CH_3$ or halogen;

$R^7$ and $R^{10}$ are H;

$R^8$ and $R^9$ are each independently H or $C_1$-$C_2$ alkyl;

$R^3$ is phenyl, naphthyl, a 6-membered heteroaromatic ring having 1-2 heteroatoms independently selected from N and —($NR^8$)—, thienyl, $C_5$-$C_6$cycloalkyl optionally having one double bond, or a 6-membered saturated heterocycle having 1-2 heteroatoms independently selected from O, S, N, and $NR^8$, wherein $R^3$ is optionally substituted with $C_1$-$C_3$alkyl, —$OC_1$-$C_3$alkyl, F, Cl, and a 6-membered saturated heterocycle having 1-2 heteroatoms independently selected from O, S, N, and $NR^8$, wherein $C_1$-$C_3$ alkyl and $OC_1$-$C_3$ alkyl are optionally substituted with 1-5 F, and the 6-membered saturated heterocycle having 1-2 heteroatoms independently selected from O, S, N, and $NR^8$ is optionally substituted with 1-3 substituents independently selected from $CF_3$, $CH_3$, —$OCF_3$, —$OCH_3$, Br, Cl, and F;

$R^4$ is H or $C_1$-$C_2$ alkyl;

or alternatively, $R^3$ is phenyl and $R^4$ has the formula (—$CH_2$—)$_y$, wherein y is an integer from 2-4 and (—$CH_2$—)$_y$ optionally comprises one double bond, wherein $R^4$ is connected to the phenyl group $R^3$ at the position ortho to the carbon atom which is connected to the carbon atom to which $R^3$, $R^4$, and $R^7$ are attached, thereby yielding a 4-7 membered cycloalkyl or cycloalkenyl ring fused to the phenyl group $R^3$, wherein the phenyl ring $R^3$ and the fused cycloalkyl or cycloalkenyl ring together are optionally substituted with 1-4 groups independently selected from $CF_3$, $CH_3$, —$OCF_3$, —$OCH_3$, and halogen; and x is 1 or 2.

2. The compound of claim 1, or a pharmaceutically acceptable salt thereof, wherein:

$R^1$ is $CF_3$; and $R^2$ is phenyl, naphthyl, pyrazolyl, pyridinyl, pyrimidinyl, or 2,3-dihydrobenzodioxinyl, wherein $R^2$ is optionally substituted with 1-2 substituents independently selected from $CH_3$, —$OCH_3$, $CF_3$, —$OCF_3$, —$OC_2H_5$, —$OCF_2H$, —$OCF_2CF_2H$, —$C(CH_3)_2OH$, —C(=O)$NHCH_3$, —C(=O)$OCH_3$, —$SO_2CH_3$, —$N(CH_3)_2$, F, Cl, —CN, and phenyl.

3. The compound of claim 2, or a pharmaceutically acceptable salt thereof, wherein:

$R^3$ is phenyl, pyridinyl, thienyl, cyclohexyl, cyclohexenyl, or tetrahydropyranyl optionally substituted with 1-2 substituent groups independently selected from $CH_3$, —$OCH_3$, $CF_3$, —$OCF_2H$, —$OCF_3$, $C_2H_5$, —$OC_2H_5$, —$OCH(CH_3)_2$, —$OCF_2CF_2H$, F, Cl, and morpholinyl;

$R^4$ is H or $CH_3$;

or alternatively, when $R^3$ is phenyl, $R^4$ optionally is (—$CH_2$—)$_3$ or —HC=CH—, wherein $R^4$ is attached to the phenyl group $R^3$ at the position that is ortho to the carbon atom that is attached to the carbon atom to which $R^3$, $R^4$, and $R^7$ are attached, thereby yielding a tetrahydronaphthalenyl or indenyl ring connected to the N of the benzopiperazine;

$R^5$ is H or F; and $R^6$, $R^7$ and $R^{10}$ are H.

4. The compound of claim 1, or a pharmaceutically acceptable salt thereof, having formula Ib:

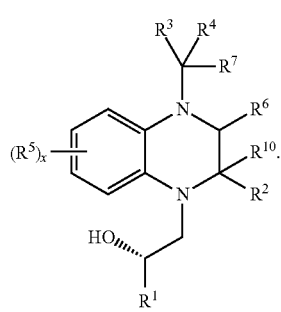

5. The compound of claim 1, or a pharmaceutically acceptable salt thereof, having formula Ic:

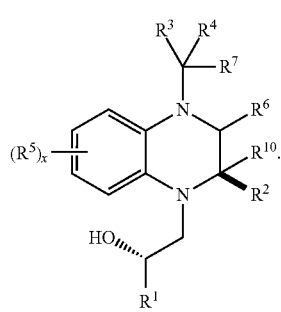

6. The compound of claim 1, or a pharmaceutically acceptable salt thereof, having formula Id:

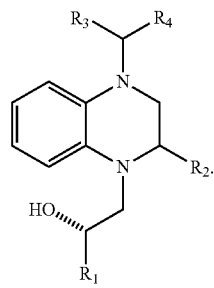

Id

7. The compound of claim 1, or a pharmaceutically acceptable salt thereof, having formula Ie:

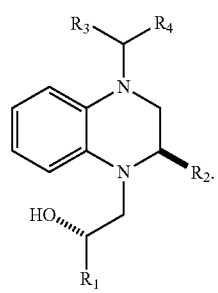

Ie

8. The compound of claim 1, having the structure below:

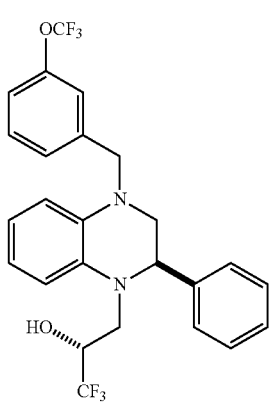 [SMILES: O[C@H](CN1c2ccccc2N(Cc2cccc(OC(F)(F)F)c2)C[C@H]1c1ccccc1)C(F)(F)F]

or a pharmaceutically acceptable salt thereof.

9. The compound of claim 1, having the structure below:

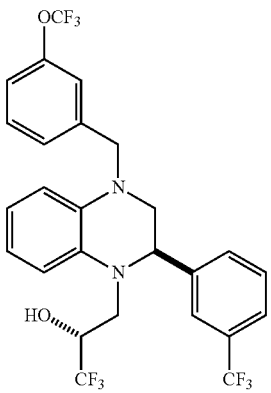 [SMILES: O[C@H](CN1c2ccccc2N(Cc2cccc(OC(F)(F)F)c2)C[C@H]1c1cccc(C(F)(F)F)c1)C(F)(F)F]

or a pharmaceutically acceptable salt thereof.

10. The compound of claim 1, having the structure below:

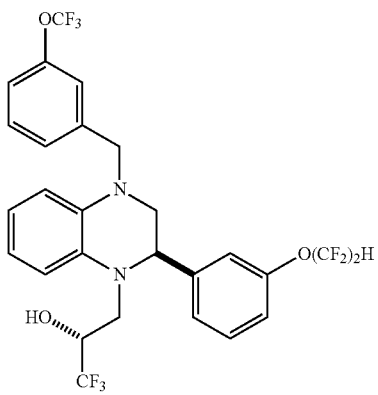

or a pharmaceutically acceptable salt thereof.

11. The compound of claim 3, or a pharmaceutically acceptable salt thereof, having the structure below:

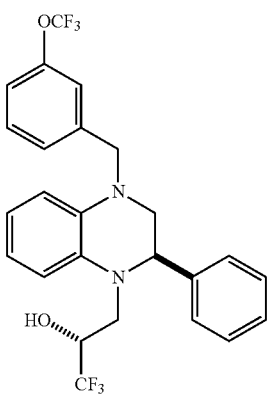

-continued
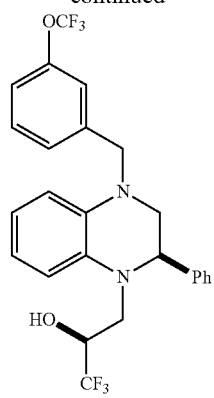
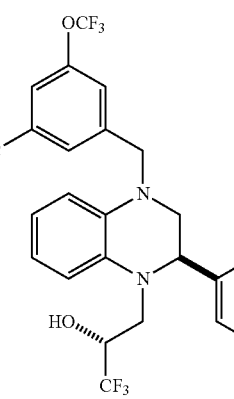
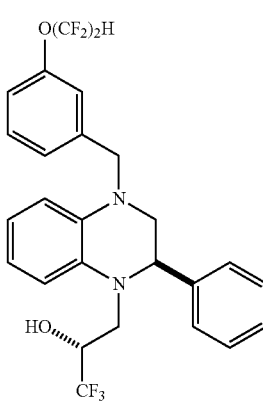
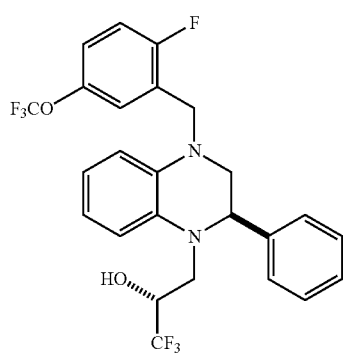
-continued
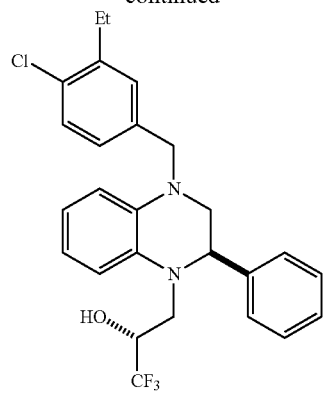
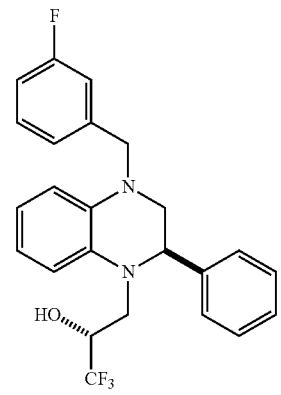
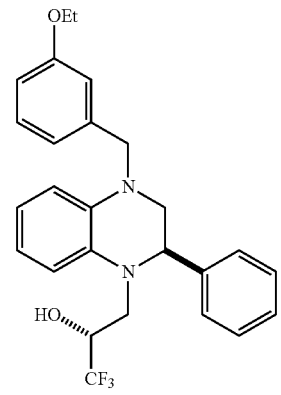
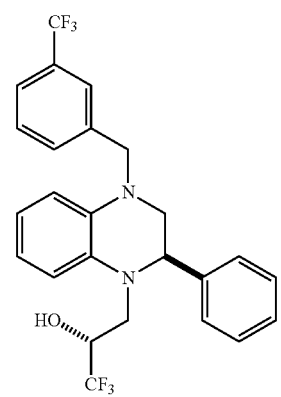

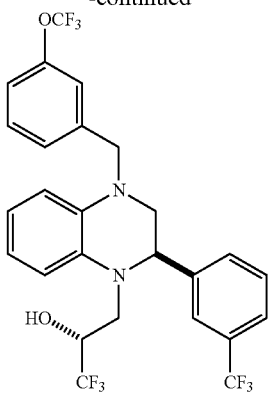
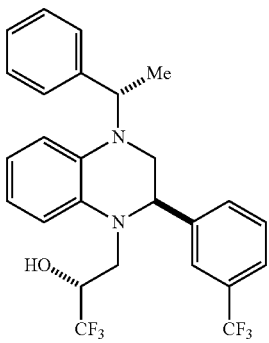
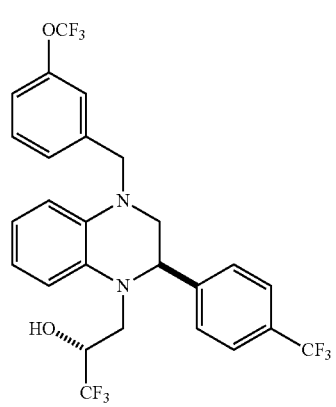
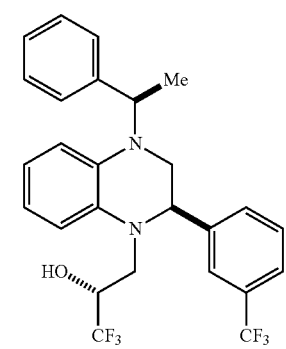
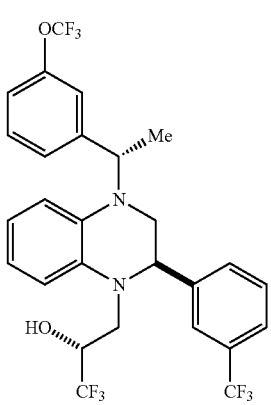
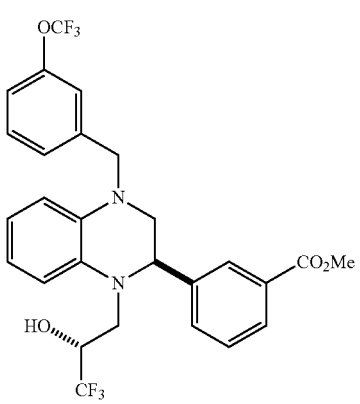
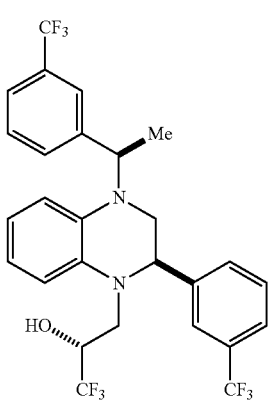
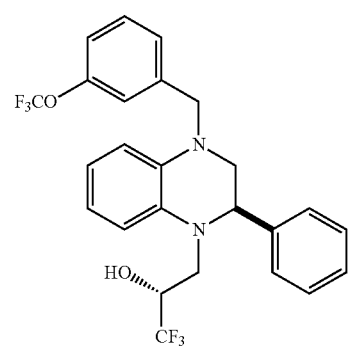

77
-continued
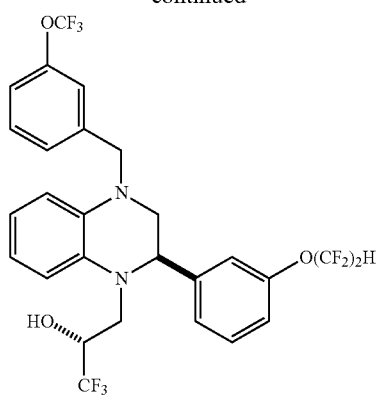
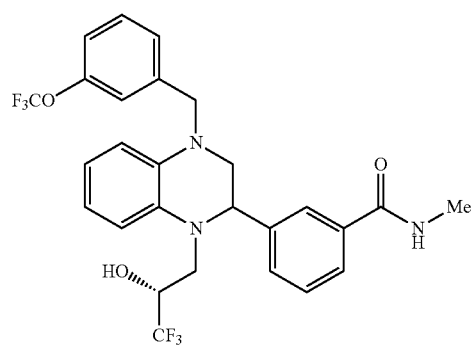
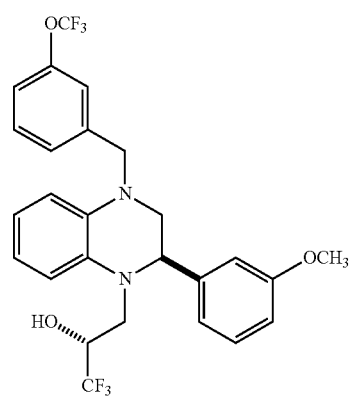
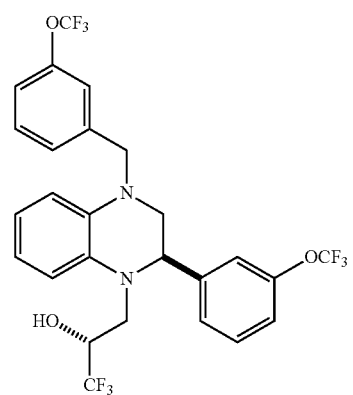
78
-continued
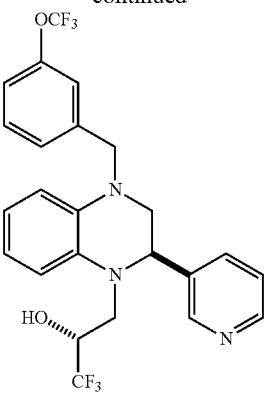
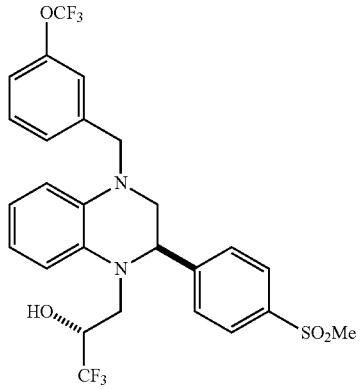
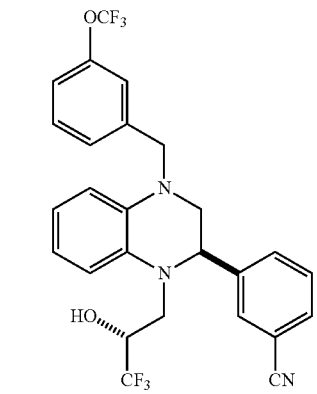
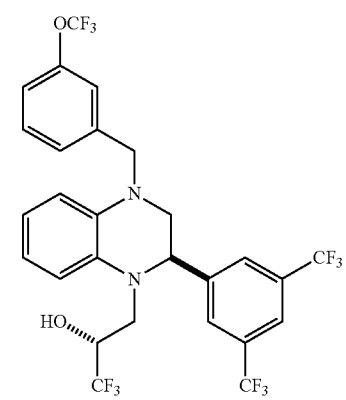

-continued
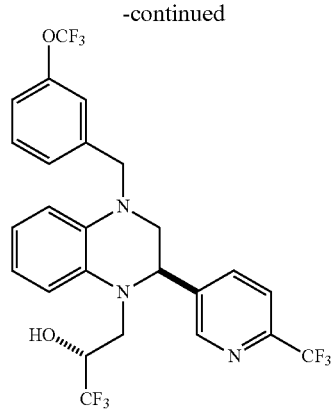
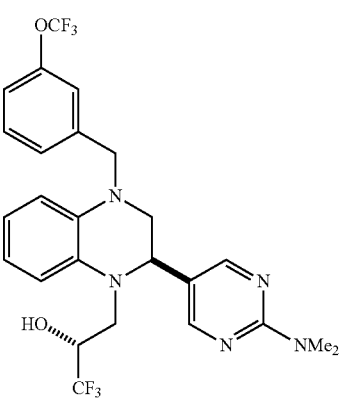
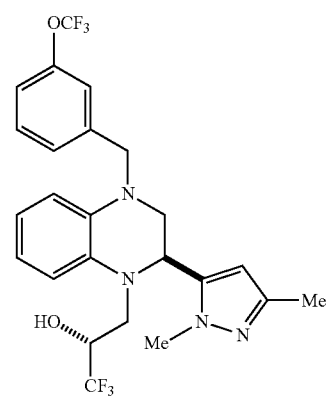
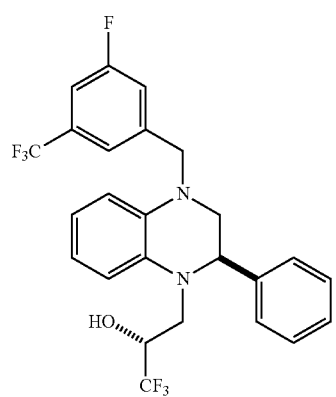
-continued
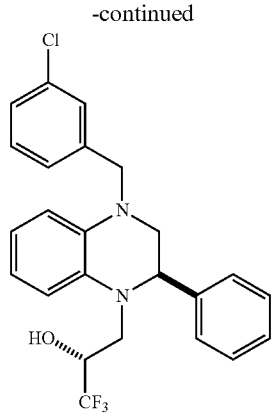
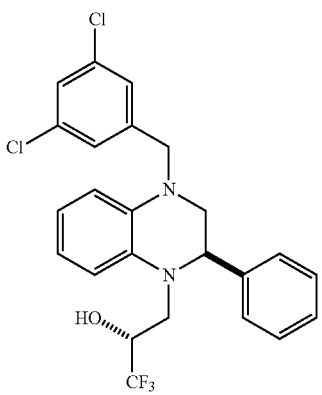
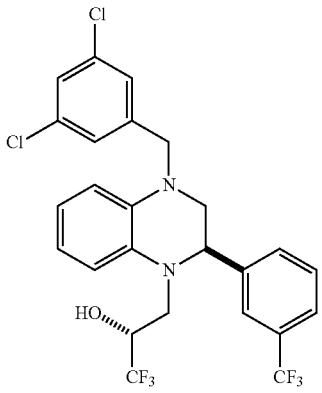
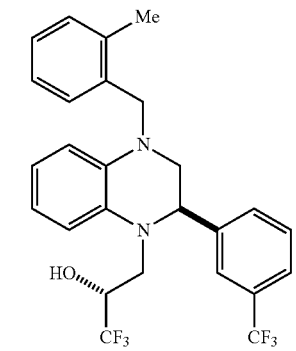

81
-continued
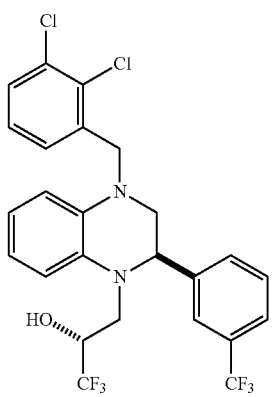
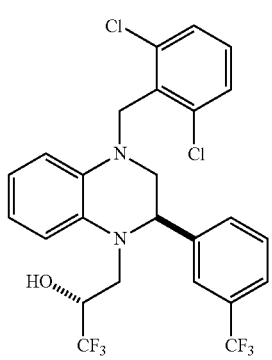
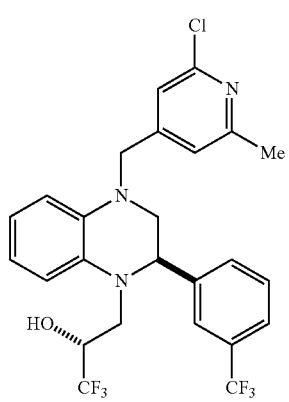
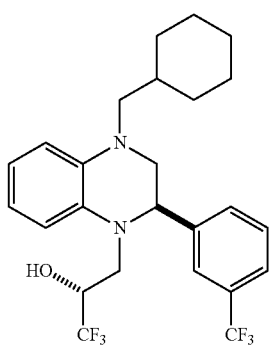
82
-continued
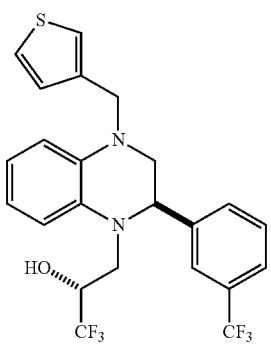
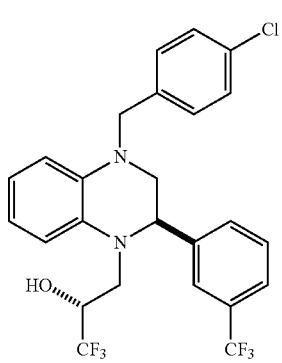
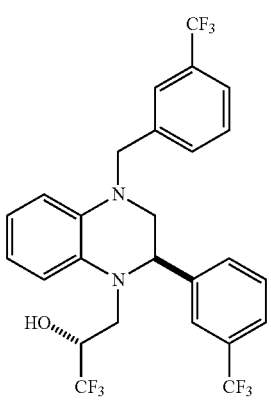
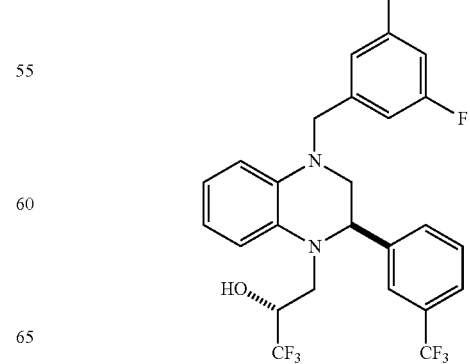

-continued
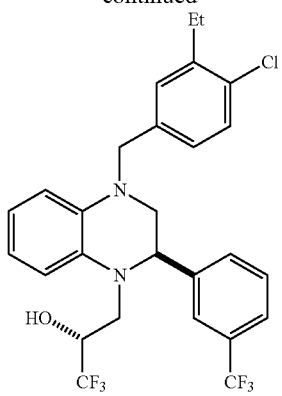
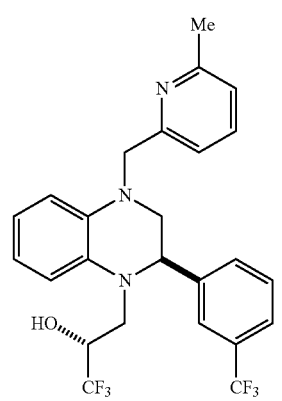
-continued
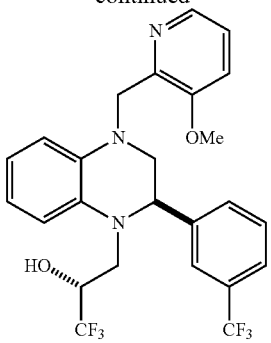
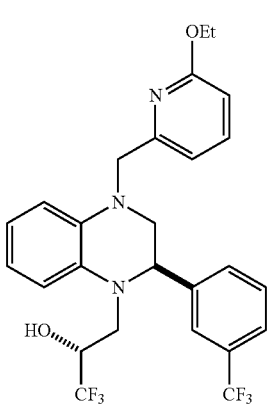
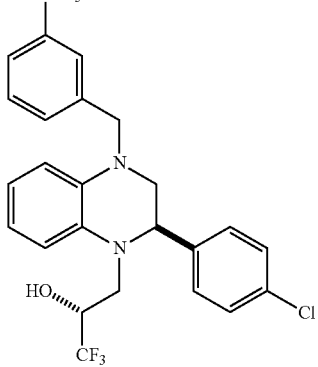

85
-continued
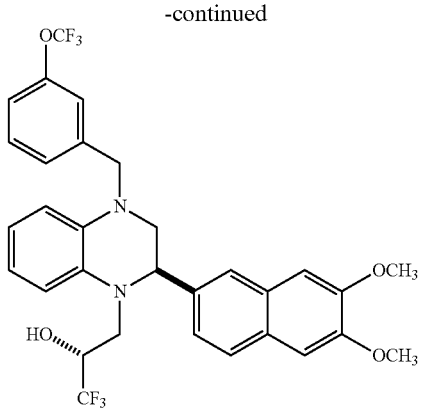
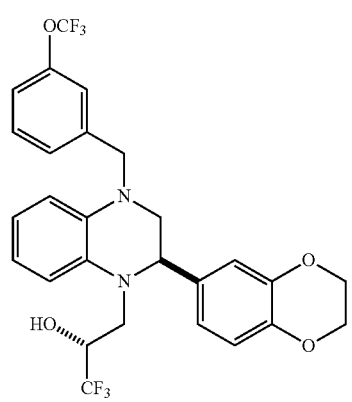
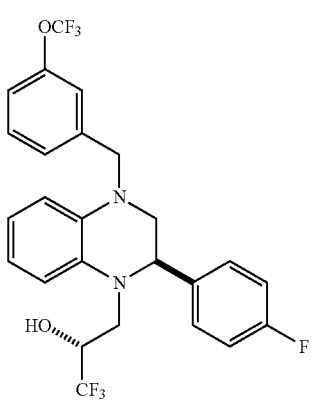
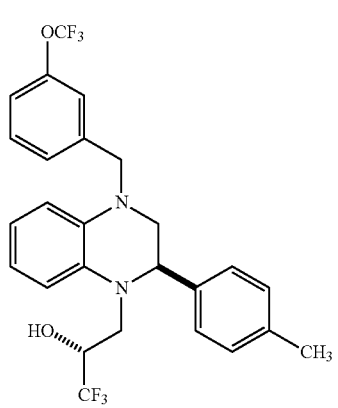
86
-continued
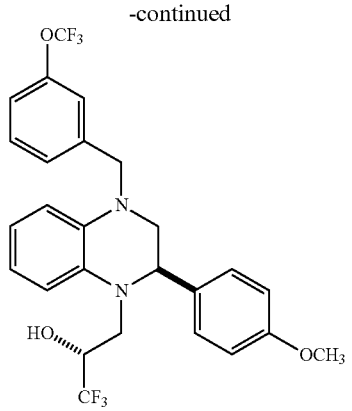
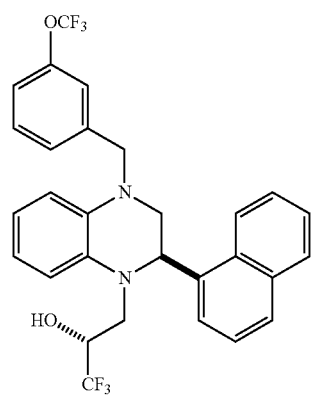
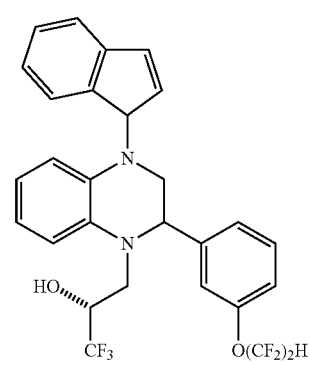
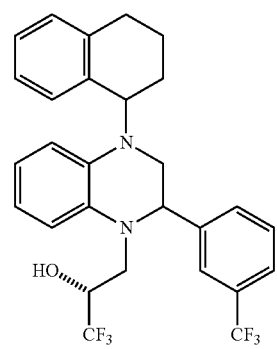

87
-continued
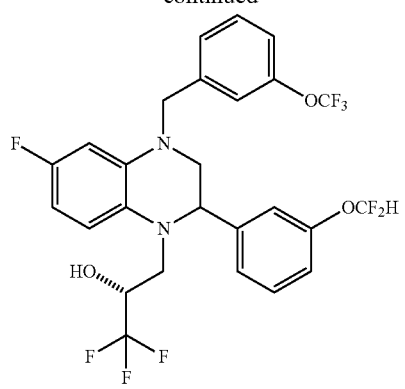
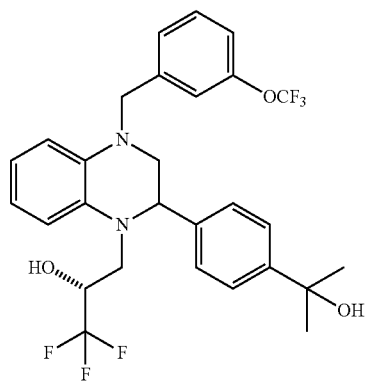
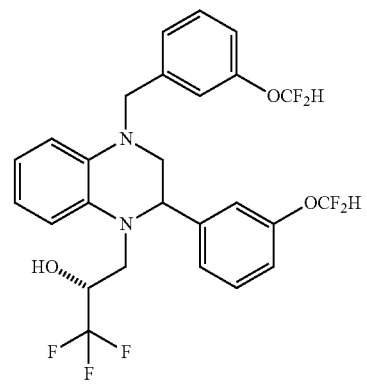
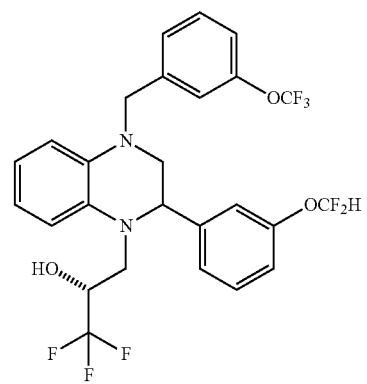
88
-continued
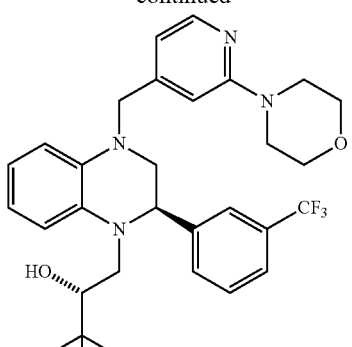
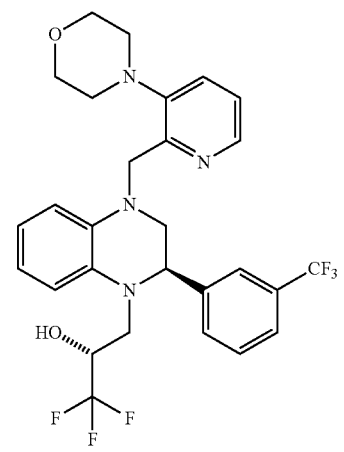
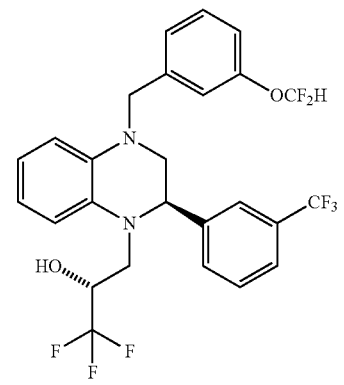
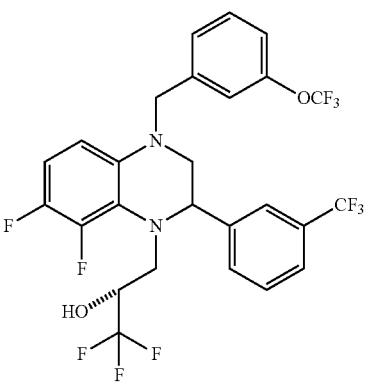

-continued

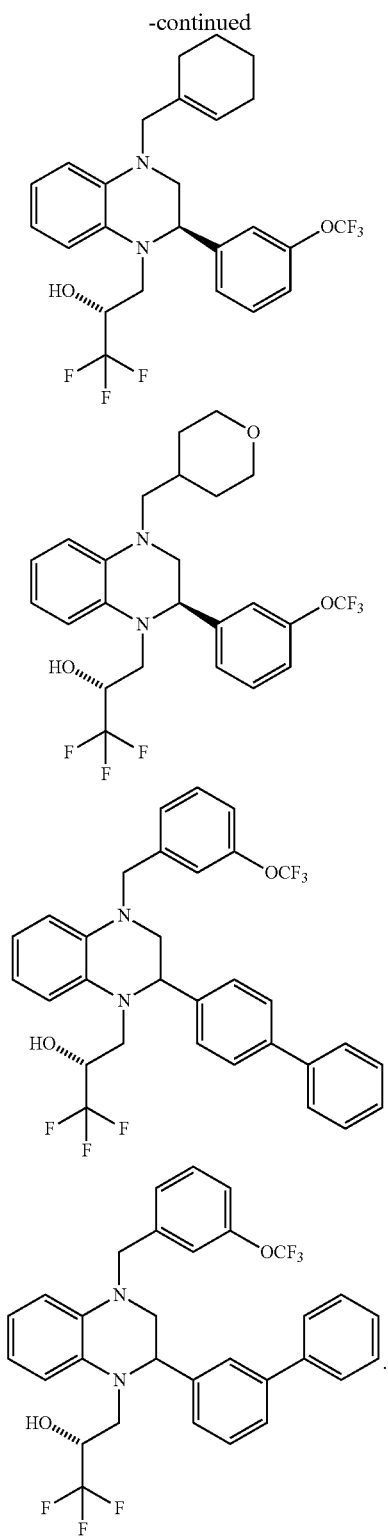

12. A pharmaceutical composition comprising the compound of claim 1 or a pharmaceutically acceptable salt thereof, and a pharmaceutically acceptable carrier.

13. A pharmaceutical composition comprising the compound of claim 1 or a pharmaceutically acceptable salt thereof, a pharmaceutically acceptable carrier, and one or more active ingredients selected from the group consisting of:

(i) 3-hydroxy-3-methylglutaryl-CoA reductase inhibitors;

(ii) bile acid sequestrants;

(iii) niacin and related compounds;

(iv) peroxisome proliferator-activated receptor α agonists;

(v) cholesterol absorption inhibitors;

(vi) acyl CoA:cholesterol acyltransferase inhibitors;

(vii) phenolic anti-oxidants;

(viii) microsomal triglyceride transfer protein/apolipoprotein B secretion inhibitors;

(ix) anti-oxidant vitamins;

(x) thyromimetics;

(xi) low density lipoprotein receptor inducers;

(xii) platelet aggregation inhibitors;

(xiii) vitamin B12;

(xiv) folic acid or a pharmaceutically acceptable salt or ester thereof;

(xv) farnesoid X and liver X ligands;

(xvi) agents that enhance ATP-binding cassette, sub-family A, member 1 gene expression; and (xvii) ileal bile acid transporters.

14. A method of treating atherosclerosis in a patient in need of treatment comprising the administration of a therapeutically effective amount of the compound of claim 1 to said patient, or a pharmaceutically acceptable salt thereof.

15. A method of raising high-density lipoprotein cholesterol in a patient in need of treatment comprising the administration of a therapeutically effective amount of the compound of claim 1 to said patient, or a pharmaceutically acceptable salt thereof.

16. A method of lowering low-density lipoprotein cholesterol in a patient in need of treatment comprising the administration of a therapeutically effective amount of the compound of claim 1 to said patient, or a pharmaceutically acceptable salt thereof.

17. A method of treating dyslipidemia in a patient in need of treatment comprising the administration of a therapeutically effective amount of the compound of claim 1 to said patient, or a pharmaceutically acceptable salt thereof.

* * * * *